(12) United States Patent
Lamichhane et al.

(10) Patent No.: US 10,695,322 B2
(45) Date of Patent: Jun. 30, 2020

(54) INHIBITORS OF BACTERIAL GROWTH

(71) Applicant: THE JOHNS HOPKINS UNIVERSITY, Baltimore, MD (US)

(72) Inventors: Gyanu Lamichhane, Towson, MD (US); Craig A. Townsend, Baltimore, MD (US); Evan Lloyd, Bunker Hill, WV (US); Amit Kaushik, Baltimore, MD (US); Pankaj Kumar, Baltimore, MD (US); Joel Freundlich, Princeton, NJ (US); Shaogang Li, Newark, NJ (US); Sean Ekins, Fuquay Varina, NC (US); Nicole Parrish, Bunker Hilol, WV (US)

(73) Assignees: The Johns Hopkins University, Baltimore, MD (US); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/073,759

(22) PCT Filed: Jan. 26, 2017

(86) PCT No.: PCT/US2017/015046
§ 371 (c)(1),
(2) Date: Jul. 27, 2018

(87) PCT Pub. No.: WO2017/132321
PCT Pub. Date: Aug. 3, 2017

(65) Prior Publication Data
US 2019/0167637 A1     Jun. 6, 2019

Related U.S. Application Data

(60) Provisional application No. 62/288,532, filed on Jan. 29, 2016.

(51) Int. Cl.
| | | |
|---|---|---|
| A61K 31/407 | (2006.01) |
| A61P 31/04 | (2006.01) |
| A61K 31/431 | (2006.01) |
| A61K 45/06 | (2006.01) |
| C07D 477/00 | (2006.01) |
| C07D 499/897 | (2006.01) |
| C07D 477/20 | (2006.01) |
| C07D 499/893 | (2006.01) |
| A61K 31/427 | (2006.01) |
| A61K 31/496 | (2006.01) |
| A61K 31/546 | (2006.01) |
| A61K 31/43 | (2006.01) |
| A61K 31/4196 | (2006.01) |

(52) U.S. Cl.
CPC ........ *A61K 31/407* (2013.01); *A61K 31/4196* (2013.01); *A61K 31/427* (2013.01); *A61K 31/43* (2013.01); *A61K 31/431* (2013.01); *A61K 31/496* (2013.01); *A61K 31/546* (2013.01); *A61K 45/06* (2013.01); *A61P 31/04* (2018.01); *C07D 477/00* (2013.01); *C07D 477/20* (2013.01); *C07D 499/893* (2013.01); *C07D 499/897* (2013.01)

(58) Field of Classification Search
CPC .... A61K 31/407; A61K 31/431; A61K 45/06; A61P 31/04; C07D 477/00; C07D 499/897
USPC ........................................................ 514/192
See application file for complete search history.

(56) References Cited

U.S. PATENT DOCUMENTS

| | | |
|---|---|---|
| 4,683,296 A | 7/1987 | Ueda et al. |
| 4,833,167 A | 5/1989 | Christensen et al. |
| 4,918,184 A | 4/1990 | Nagao et al. |
| 5,011,150 A | 4/1991 | Averill |
| 5,075,437 A | 12/1991 | Nakai et al. |
| 5,104,984 A | 4/1992 | Salzmann et al. |
| 5,231,179 A | 7/1993 | Terashima et al. |
| 5,260,438 A | 11/1993 | Tanabe Seiyaku |
| 5,399,363 A | 3/1995 | Liversidge et al. |
| 5,414,081 A | 5/1995 | Tanabe Seiyaku |
| 5,424,422 A | 6/1995 | Sunagawa et al. |
| 5,443,057 A | 8/1995 | Elmore |
| 5,463,046 A | 10/1995 | Cho et al. |
| 5,466,468 A | 11/1995 | Schneider et al. |
| 5,493,018 A | 2/1996 | Liu et al. |
| 5,543,158 A | 8/1996 | Gref et al. |
| 5,574,152 A | 11/1996 | Miura et al. |

(Continued)

FOREIGN PATENT DOCUMENTS

| | | |
|---|---|---|
| DE | 2652675 A1 | 6/1997 |
| DE | 2652678 A1 | 6/1997 |
| EP | 0528678 A1 | 2/1993 |

OTHER PUBLICATIONS

Mathiowitz et al. Biologically erodable microspheres as potential oral drug delivery systems. Nature 1997, 386:410-414.

(Continued)

*Primary Examiner* — Kristin A Vajda
(74) *Attorney, Agent, or Firm* — John Hopkins Technology Ventures

(57) ABSTRACT

New antimicrobials targeting L,D-transpeptidases, non-classical cysteine peptidases, have been developed and their unique chemical structures identified. Carbapenems and penems of the present invention are unique among β-lactams as they acylate and inhibit L,D-transpeptidases, which likely results in their superior antimicrobial potency. These new antimicrobial agents can be used alone, or in combination with other classic antimicrobial agents that target D,D transpeptidases, when treating bacterial infections.

15 Claims, 37 Drawing Sheets
Specification includes a Sequence Listing.

(56) References Cited

U.S. PATENT DOCUMENTS

| | | |
|---|---|---|
| 5,578,722 A | 11/1996 | Sunagawa et al. |
| 5,580,579 A | 12/1996 | Ruddy et al. |
| 5,580,976 A | 12/1996 | Kume et al. |
| 5,587,474 A | 12/1996 | Tanabe Seiyaku |
| 5,629,001 A | 5/1997 | Michael et al. |
| 5,641,515 A | 6/1997 | Ramtoola |
| 5,703,234 A | 12/1997 | Iwasaki et al. |
| 5,725,871 A | 3/1998 | Illum |
| 5,731,431 A | 3/1998 | Nakagawa et al. |
| 5,756,353 A | 5/1998 | Debs |
| 5,780,045 A | 7/1998 | McQuinn et al. |
| 5,792,451 A | 8/1998 | Sarubbi et al. |
| 5,792,861 A | 8/1998 | Hara et al. |
| 5,804,212 A | 9/1998 | Illum |
| 5,973,142 A | 10/1999 | Yasuda et al. |
| 6,080,854 A | 6/2000 | Chung et al. |
| 6,162,911 A | 12/2000 | Ball et al. |
| 6,340,751 B1 | 1/2002 | Saito et al. |
| 6,613,308 B2 | 9/2003 | Bartus et al. |
| 6,737,514 B1 | 5/2004 | Wang et al. |
| 6,858,727 B2 | 2/2005 | Lee et al. |
| 6,867,297 B1 | 3/2005 | Ishiguro et al. |

OTHER PUBLICATIONS

Takenaga et al. Microparticle resins as a potential nasal drug delivery system for insulin., Journal of Controlled Release 1998, 52:81-87.

Isabella et al. Toward the rational design of carbapenem uptake in pseudomonas aeruginosa. Chemistry & Biology, 2015, 22(4):535-47.

Bodner et al. Non-Heme iron oxygenases generate natural structural diversity in carbapenem antibiotics. Journal f the American Chemical Society, 2010, 132(1):12-13.

Brown et al. Structures of olivanic acid derivatives MM 22380, MM22381, MM22382 and MM22383; four new antibiotics isolated from Streptomyces olivaceus. Journal of Antibiotics, 1979, 32(9):961.

Sunagawa et al. Structure activity relationaship of 1beta-methylcarbapenem to its antibacterial activity: effect of the C-2 side chain and the 1-methyl group. Journal of Antibiotics, 1996, 49(11):1175.

Burton et al. Novel C-2 substituted carbapenem derivatives. Part I. Synthesis and biological activity of non-aromatic heterocyclic derivatives. Journal of Antibiotics, 1996, 49(12):1258.

Rotilie et al., Microdilution technique for antimicrobial susceptibility testing of anaerobic bacteria. Antimicrobial agents and chemotherapy. 1975; 7(3): 311-15.

Gavan TL, et al., "A microdilution method for antibiotic susceptibility testing: an evaluation" American journal of clinical athology. 1970; 53(6): 880-5.

FIGURE 1: TABLES 1 & 2

| Protein | Amoxicillin (MW=365.4) | Cephalothin (MW=396.4) | Doripenem (MW=420.1) | Faropenem (MW=285.3) | ACZF | DBFT | T205 (MW=337.3) | T206 (MW=365.4) | T208 (MW=405.4) | T210 (MW=279.3) |
|---|---|---|---|---|---|---|---|---|---|---|
| Ldt$_{Mt1}$ | No adduct | No adduct | +376, +421 | +86 | +86 | +86 | +316 | +344 | +385 | +258 |
| Ldt$_{Mt2}$ | No adduct | +335 | +123 | +86 | +86 | +86 | +337 | +343 | +383 | +257 |
| Ldt$_{Mab1}$ | +366 | +337, +355 | +376, +421 | +86 | +86 | +86 | +337 | +344 | +383 | +258 |
| Ldt$_{Mab2}$ | No adduct | No adduct | +68 | +86 | +86 | +86 | No adduct | No adduct | No adduct | No adduct |
| Ldt$_{Kp}$ | No adduct | No adduct | +376, +421 | +86, +288 | +86 | +86 | +317 | +344 | No adduct | +258 |
| Ldt$_{Cl}$ | No adduct | +337 | +376, +421 | +86, +172 | +86 | +86 | +316 | +344 | +383 | +258 |
| Ldt$_{Pa}$ | No adduct | No adduct | No adduct | +86, +288 | +457 | n.d. | +317 | No adduct | +56 | +258 |

Table 1: Mass-spectrometric analysis of adducts formed between Ldt$_{Mt1}$, Ldt$_{Mt2}$, Ldt$_{Mab1}$, Ldt$_{Mab2}$, Ldt$_{Kp}$, Ldt$_{Cl}$, and Ldt$_{Pa}$ and a range of compounds. Molecular weights (MW) of detected adducts are shown (in daltons). A (Amoxicillin), C (Cephalothin), Z (Aztreonam, MW=435.4), D (Doripenem), F (Faropenem), B (Biapenem, MW=350.4) and T (Tebipenem, MW=383.5). Not determined (n.d.).

| Carbapenem | A. baumannii | K. pneumoniae | E. cloacae | P. aeruginosa | E. faecalis | MSSA | MRSA | M. tuberculosis | M. abscessus |
|---|---|---|---|---|---|---|---|---|---|
| Meropenem | 1-2 | <0.06 | 0.13-0.25 | 0.25-0.5 | 4-8 | 0.06-0.13 | 0.06-0.13 | 4-8 | >64 |
| T123 | 2-4 | 4-8 | >64 | 2-4 | >64 | 0.5-1 | 0.5-1 | >64 | >64 |
| T202 | 4-8 | 1-2 | >64 | >64 | 16-32 | 1-2 | 0.5-1 | 2-4 | >64 |
| T203 | 4-8 | 0.5-1 | >64 | >64 | 8-16 | 0.5-1 | 0.25-0.5 | 2-4 | >64 |
| T205 | 4-8 | 0.25-0.5 | >64 | >64 | 8-16 | 0.5-1 | 0.5-1 | 1-2 | >64 |
| T206 | 8-16 | 4-8 | >64 | >64 | 16-32 | 1-2 | 1-2 | 1-2 | >64 |
| T207 | 4-8 | 2-4 | >64 | >64 | 16-32 | 1-2 | 0.5-1 | 2-4 | >64 |
| T208 | 2-4 | 8-16 | >64 | >64 | 8-16 | 0.5-1 | 0.5-1 | 1-2 | >64 |
| T209 | >64 | >64 | >64 | >64 | >64 | >64 | >64 | 2-4 | >64 |
| T210 | 16-32 | 0.5-1 | >64 | >64 | 16-32 | 2-4 | 2-4 | 0.25-0.5 | >64 |
| T221 | 2-4 | 0.5-1 | 4-8 | >64 | 8-16 | 0.25-0.5 | 0.25-0.5 | 4-8 | >64 |
| T222 | 0.5-1 | 4-8 | 8-16 | >64 | 1-2 | 0.06-0.12 | 0.12-0.25 | 1-2 | >64 |
| T223 | 0.5-1 | 4-8 | 32-64 | >64 | 2-4 | 0.12-0.25 | 0.12-0.25 | 2-4 | >64 |
| T224 | 0.25-0.5 | 32-64 | >64 | 64 | 8-16 | 0.25-0.5 | 0.25-0.5 | 2-4 | >64 |

Table 2: Minimum inhibitory concentrations (MIC) of experimental carbapenems in μg/ml. The data shown in this table was verified with two repeats of MIC determination. MSSA and MRSA refer to Methicillin sensitive and resistant *Staphylococcus aureus*, respectively. Meropenem was used as a control.

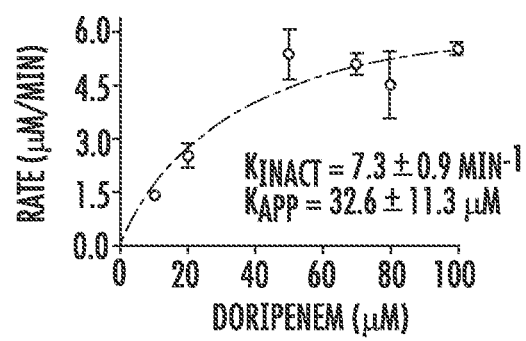
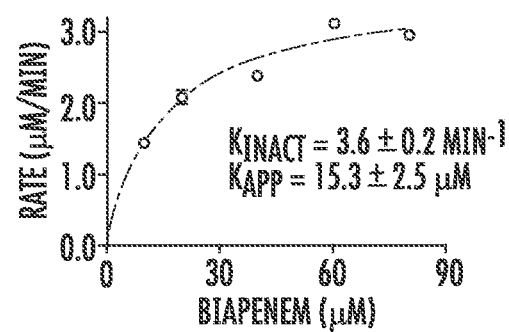
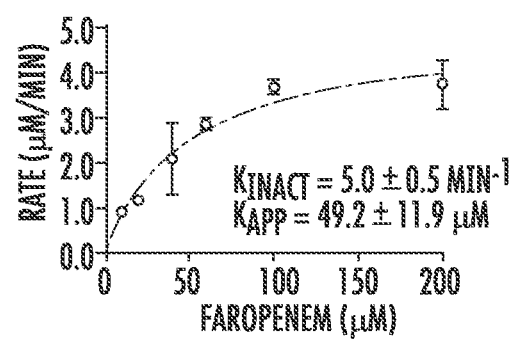
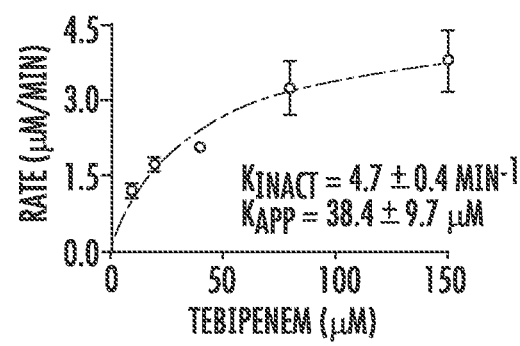
FIG. 2B

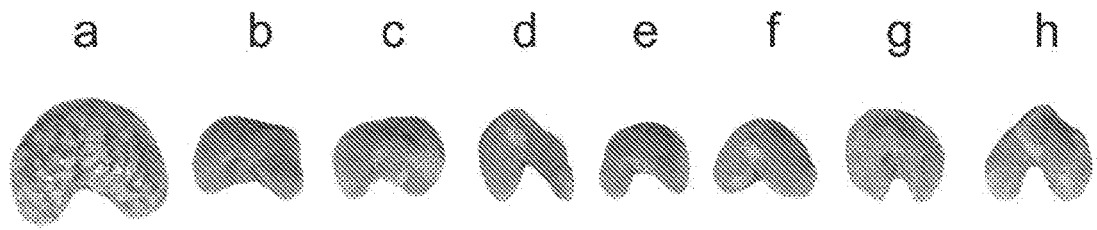

Figure 3: a. Gross pathology of lungs of mice infected with *M. tuberculosis*. Mice received the following treatments: (a) no treatment, (b) isoniazid, (c) rifampicin, (d) isoniazid + rifampicin, (e) biapenem, (f) biapenem + rifampicin, (g) faropenem, (h) faropenem + rifampicin. Each lung shown here is representative of lungs of mice in the corresponding treatment group.

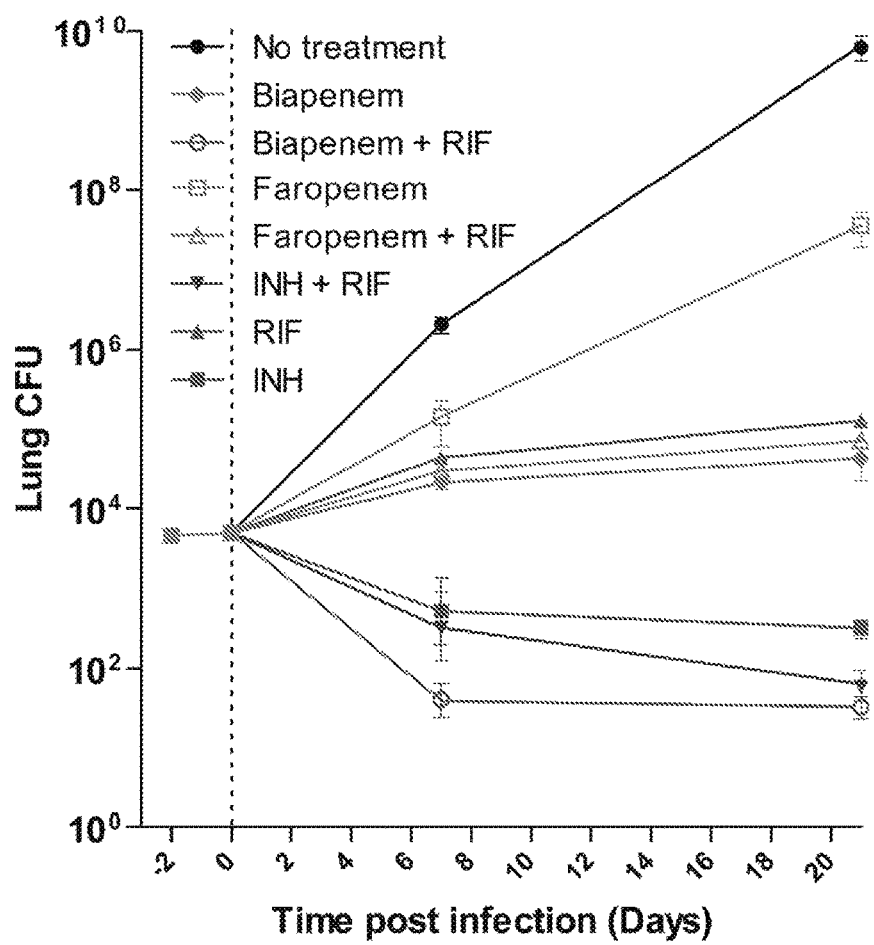

Figure 3: b. *M. tuberculosis* burden in the lungs of mice. Total number of *M. tuberculosis* bacilli that could be recovered from lungs of mice at various stages of infection and treatment. Isoniazid (INH) and rifampicin (RIF).

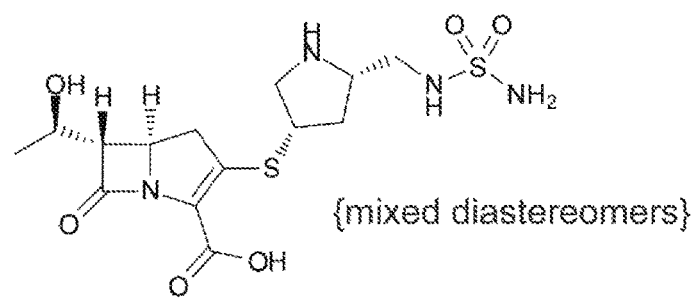
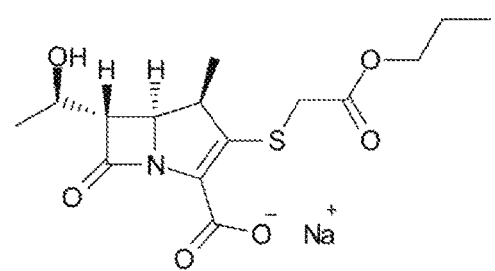
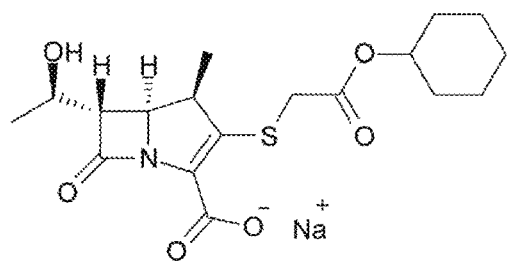
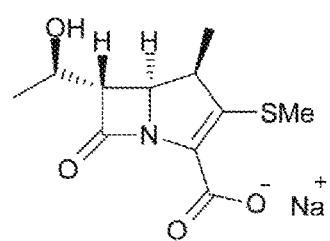
Figure 4a: Chemical structures of some of the evolved carbapenems. From top to bottom, T123, T206, T208 and T210.

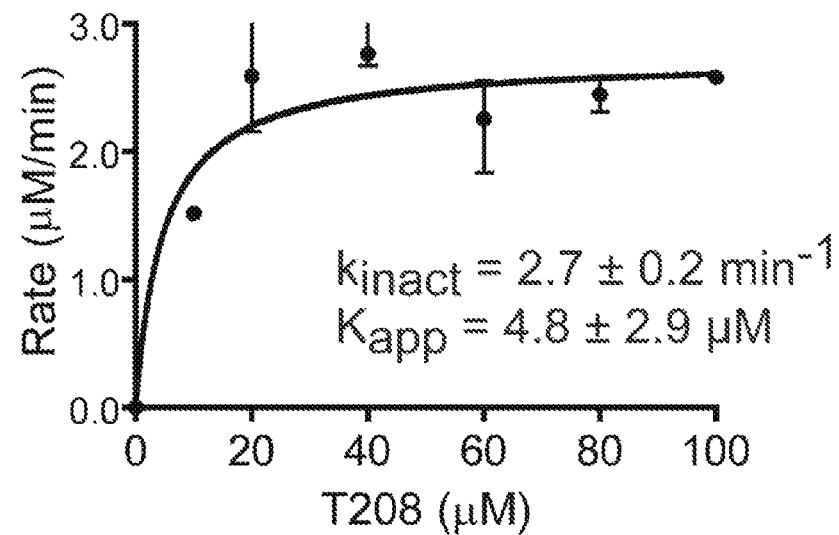
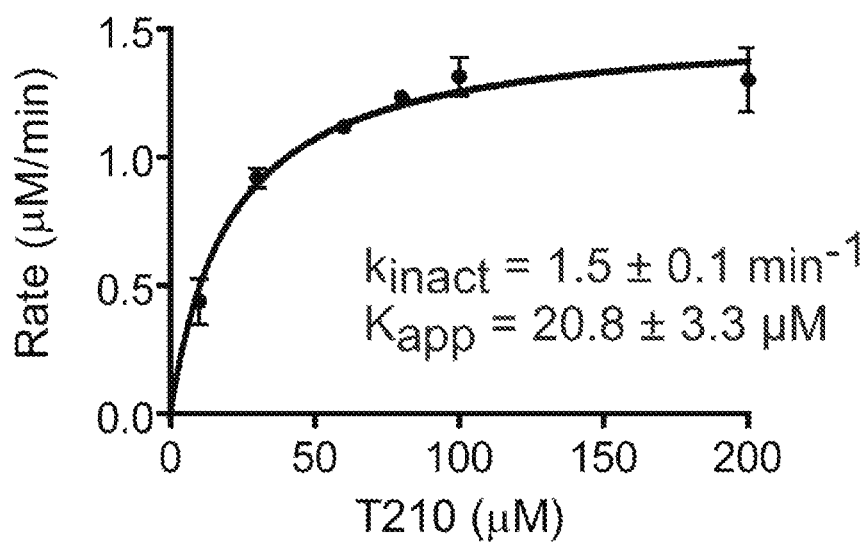
Figure 4: b, Kinetics of acylation of Ldt$_{Mt2}$ by evolved carbapenems T208 and T210. Kinetic constansts k$_{inact}$ and K$_{app}$ were determined spectrophotometrically.

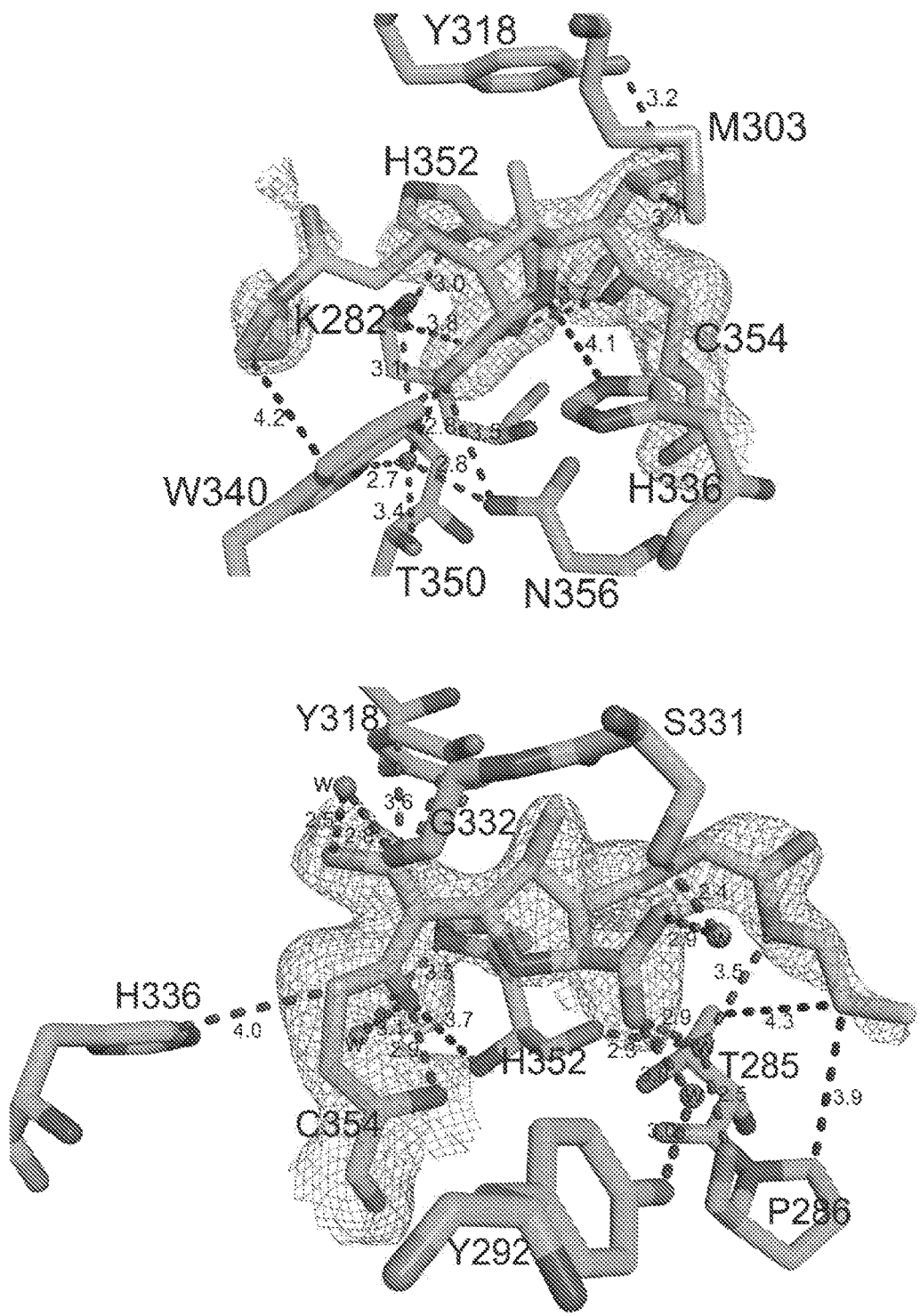
Figure 4: c, Crystal structure of T206 at the catalytic site of Ldt$_{Mt2}$. Conformation A (top panel) and conformation B (bottom panel) showing interaction of T206 adduct (cyan) with residues at the catalytic site of Ldt$_{Mt2}$ (green) and water (w). The 2Fo-Fc difference fourier map (gray) is contoured at 1.0σ. Distances are in Å.

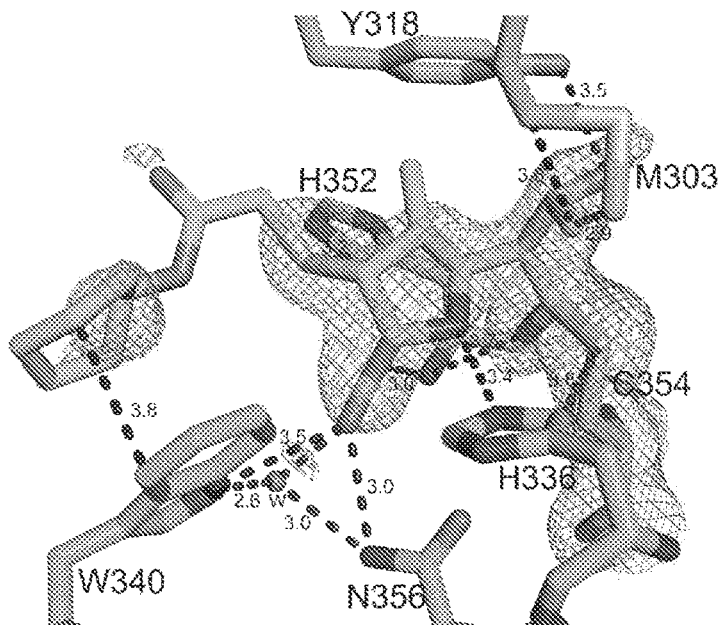

Figure 4: d, Crystal structure of T208 at the catalytic site of Ldt$_{Mt2}$. Interaction of T206 adduct (cyan) with residues at the catalytic site of Ldt$_{Mt2}$ (green) and water(w). The 2Fo-Fc difference fourier map (gray) is contoured at 1.0σ. Distances are in Å.

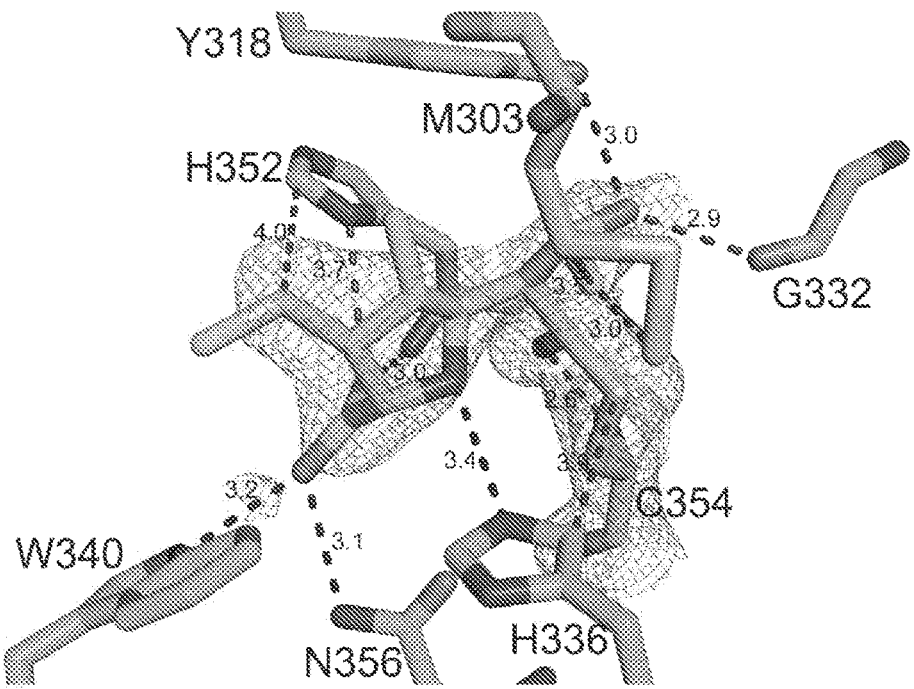

Figure 4: e, Crystal structure of T210 at the catalytic site of Ldt$_{Mt2}$. Interaction of T210 adduct (cyan) with resides at the catalytic site of Ldt$_{Mt2}$ (green). The 2Fo-Fc difference fourier map (gray) is contoured at 1.0σ. Distances are in Å.

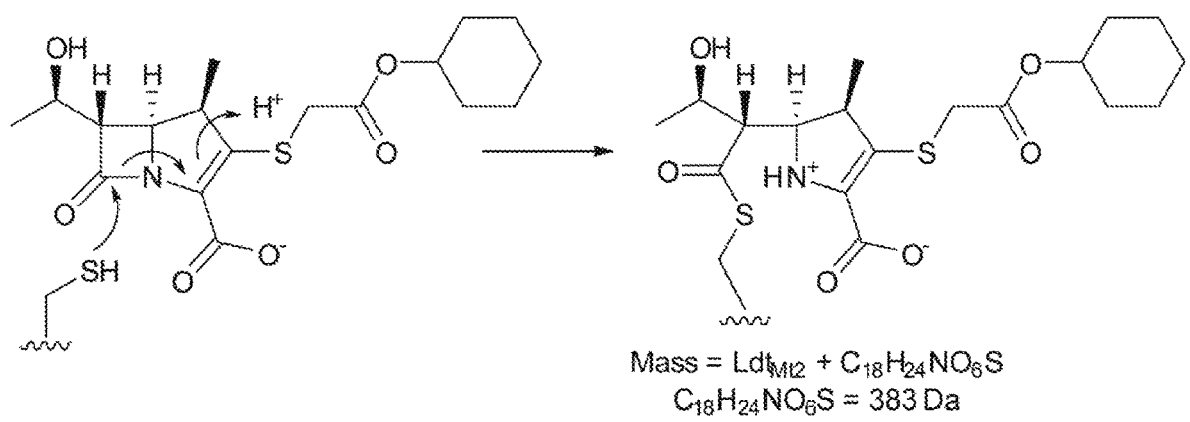
Figure 4f: Proposed mechanism of acylation of Ldt$_{Mt2}$ by T208. This mechanism is based on data on adduct from x-ray crystallography and mass-spectrometry. Carbapenems T206 and T210 react with a similar mechanism.

Figure 5

| Protein | Fragment | Primers | Plasmid | Expression Strain |
|---|---|---|---|---|
| Ldt$_{M t 2}$ | 56-408 aa | F: ATTGCCATATGGATCTGCTGGTGCCCAAGC<br>R: CAATACTCGAGTTACGCCTTGGCGTTACCG | p154KA | 161KA |
| Ldt$_{M t 2}$ Y318A | 56-408 aa | F: CAACTCGCCCAACGGA*GCA*CGCACCGATGTCGAC<br>R: GTCGACATCGGTGCG*TGC*TCCGTTGGGCGAGTTG | p1510KA | 1516KA |
| Ldt$_{M t 2}$ Y318F | 56-408 aa | F: CAACTCGCCCAACGGA*TTT*CGCACCGATGTCGAC<br>R: GTCGACATCGGTGCG*AAA*TCCGTTGGGCGAGTTG | p1512KA | 1518KA |
| Ldt$_{M t 2}$ H336A | 56-408 aa | F: CAGCGGTGTCTTCGTGGCCTCAGCGCCGTGGTCG<br>R: CGACCACGGCGCTGAGGCCACGAAGACACCGCTG | p1501KA | 1507KA |
| Ldt$_{M t 2}$ H336R | 56-408 aa | F: CGGTGTCTTCGTGC*GTT*CAGCGCCGTGGTCG<br>R: CGACCACGGCGCTGA*ACG*CACGAAGACACCG | p1526KA | 1534KA |
| Ldt$_{M t 2}$ H336N | 56-408 aa | F: CAGCGGTGTCTTCGTG*AAC*TCAGCGCCGTGGTC<br>R: GACCACGGCGCTGAG*TT*CACGAAGACACCGCTG | p1528KA | 1536KA |
| Ldt$_{M t 2}$ H352A | 56-408 aa | F: CCACACCAACACCAGCGCTGGCTGCCTGAACGTC<br>R: GACGTTCAGGCAGCCAGCGCTGGTGTTGGTGTGG | p1503KA | 1508KA |
| Ldt$_{M t 2}$ H352R | 56-408 aa | F: CACACCAACACCAGCC*GT*GGCTGCCTGAACGTC<br>R: GACGTTCAGGCAGCC*AC*GGCTGGTGTTGGTGTG | p1514KA | 1520KA |
| Ldt$_{M t 2}$ H352N | 56-408 aa | F: CCACACCAACACCAGC*AAT*GGCTGCCTGAACG<br>R: CGTTCAGGCAGCC*ATT*GCTGGTGTTGGTGTGG | p1522KA | 1530KA |
| Ldt$_{M t 2}$ C354A | 56-408 aa | F: CAACACCAGCCATGGCGCGCTGAACGTCAGCCCGAG<br>R: CTCGGGCTGACGTTCAGCGCGCCATGGCTGGTGTT | p208KA | 1505KA |
| Ldt$_{M t 2}$ C354S | 56-408 aa | F: CAACACCAGCCATGGC*AGC*CTGAACGTCAGCCC<br>R: GGGCTGACGTTCAG*GCT*GCCATGGCTGGTGTTG | p1524KA | 1532KA |
| Ldt$_{M t 1}$ | 32-251 aa | F: ATTGCCATATGCCACTCCAACCGATCCCA<br>R: CAATACTCGAGCTAGCCGACCACCTCAATGGG | p148KA | 169KA |
| Ldt$_{M a b 1}$ | 23-248 | F: ATTGCCATATGGGCCACGCATTGGCCGCAAGTCC<br>R: CAATACTCGAGTTACGCGTTGATGATGATCGG | p205KA | 213KA |
| Ldt$_{M a b 2}$ | 61-406 | F: ATTGCCATATGTCGGTTAAGGATGGAGCCGTA<br>R: CAATACTCGAGTTATTGCTGGCGGGCGTTTC | p191KA | 200KA |
| Ldt$_{K p}$ | 22-328 | F: ATTGCCATATGTGGGCCGTTGATTATCCGCTTCC<br>R: CAATACTCGAGCTATTGGGTAAGCAGACCGTTG | p1550KA | 1552KA |
| Ldt$_{C l}$ | 24-337 | F: ATTGCCATATGGATTATCCGTTACCGCCCG<br>R: CAATACTCGAGCTACTGCGTCACCTTCTCGCCATC | p1572AK | 1576KA |
| Ldt$_{P a}$ | 22-323 | F: ATTGCCATATGTCGGCCCTGGAACTGCAGCTCCCG<br>R: CAATACTCGAGTCAGGGCGTAAGCTGGGTAGGATCG | p1556KA | 1560KA |

FIGURE 5: Extended Data Table 1: Summary of materials associated with proteins described in this study. Primers are DNA oligos used for PCR amplification of fragments from genomic DNA of *M. tuberculosis, M. abscessus, K. pneumoniae, E. cloacae* and *P. aeruginosa.* Plasmid refers to the pET28a+TEV derived vector carrying desired gene. Expression strains are *E. coli* BL21DE3 clones harboring corresponding plasmid used for overexpression of proteins.

Figure 6

| Protein | Ligand | Binding model | $K_d$ (μM) | ΔH (cal/mol) | ΔS (cal/mol/deg) |
|---|---|---|---|---|---|
| Ldt$_{Mt2}$ wt | faropenem | One-site | 0.245 | -1.76E4 | -27.0 |
| Ldt$_{Mt2}$ Y318F | faropenem | One-site | 89.28 | -5.24E3 | 0.94 |
| Ldt$_{Mt2}$ H336A | faropenem | One-site | 45.45 | -6.65E2 | 17.6 |
| Ldt$_{Mt2}$ H336N | faropenem | One-site | 29.76 | -5.73E2 | 18.8 |
| Ldt$_{Mt2}$ H352N | faropenem | One-site | 39.53 | -9.37E3 | -11.3 |
| Ldt$_{Mt2}$ C354S | faropenem | One-site | 27.62 | -3.50E2 | 19.7 |
| Ldt$_{Mt2}$ wt | tebipenem | One-site | 0.517 | -3.23E3 | 16.5 |
| Ldt$_{Mt2}$ Y318F | tebipenem | One-site | 72.99 | -2.01E3 | 12.2 |
| Ldt$_{Mt2}$ H336N | tebipenem | One-site | 10.67 | -1.63E3 | 17.3 |
| Ldt$_{Mt2}$ H352N | tebipenem | One-site | 4.48 | -2.47E3 | 16.2 |
| Ldt$_{Mt2}$ C354S | tebipenem | One-site | 3.34 | -2.05E3 | 18.2 |
| Ldt$_{Mt2}$ wt | T210 | One-site | 1.24 | 6.94E3 | 46.9 |
| Ldt$_{Mt2}$ Y318F | T210 | One-site | 88.49 | 2.86E3 | 28.2 |
| Ldt$_{Mt2}$ H336N | T210 | One-site | 31.74 | -2.95E3 | 24.75 |
| Ldt$_{Mt2}$ H352N | T210 | One-site | 97.08 | -2.38E3 | 10.4 |
| Ldt$_{Mt2}$ C354S | T210 | One-site | 238.0 | -9.9E2 | 13.2 |
| Ldt$_{Mt2}$ wt | T205 | One-site | 154.7 | -6.48E2 | 15.3 |
| Ldt$_{Mt2}$ wt | T206 | One-site | 2.80 | 7.71E3 | 51.3 |
| Ldt$_{Mt2}$ wt | T208 | One-site | 5.65 | 6.49E3 | 46.9 |
| Ldt$_{Mt1}$ wt | Faropenem | One-site | 3.98 | -5.70E3 | 5.6 |
| Ldt$_{Mab2}$ wt | Faropenem | One-site | 6.25 | -2.97E4 | -75.9 |
| Ldt$_{Mab2}$ wt | Tabipenem | One-site | 6.10 | -3.60e3 | 11.9 |
| Ldt$_{Mab1}$ wt | Faropenem | One-site | 0.16 | 1.68E4 | -25.3 |
| Ldt$_{Mab1}$ wt | Tabipenem | One-site | 0.82 | -5.39E3 | 9.79 |
| Ldt$_{Mt1}$ | Cephalothin | One-site | nd | nd | nd |
| Ldt$_{Mt1}$ | Aztreonam | One-site | nd | nd | nd |
| Ldt$_{Mt2}$ | Amoxicillin | One-site | nd | nd | nd |
| Ldt$_{Mt2}$ | Cephalothin | One-site | 200 | -2.33e6 | -7.8e3 |
| Ldt$_{Mt2}$ | Aztreonam | One-site | nd | nd | nd |
| Ldt$_{Mab1}$ | Amoxicillin | One-site | 1287 | -8.28e4 | -266 |
| Ldt$_{Mab1}$ | Cephalothin | One-site | 30.3 | -3293 | 9.59 |
| Ldt$_{Mab1}$ | Aztreonam | One-site | nd | nd | nd |
| Ldt$_{Mab2}$ | Amoxicillin | One-site | nd | nd | nd |
| Ldt$_{Mab2}$ | Cephalothin | One-site | nd | nd | nd |
| Ldt$_{Mab2}$ | Aztreonam | One-site | nd | nd | nd |

| Enzyme | Ligand | Binding model | $K_{d1}$ | $ΔH_1$ | $ΔS_1$ | $K_{d2}$ | $ΔH_2$ | $ΔS_2$ |
|---|---|---|---|---|---|---|---|---|
| Ldt$_{Mab2}$ | T206 | Two-site | 18.9 | 8.44E2 | 24.4 | 234.19 | -8.0E3 | -25.6 |
| Ldt$_{Mab2}$ | T208 | Two-site | 0.02 | 1.97E3 | 42 | 0.19 | -2.30E3 | 23.1 |
| Ldt$_{Mab2}$ | T210 | Two-site | 228.8 | -7.13E3 | -7.29 | 1666 | -1.06E5 | -3.42 |

FIGURE 6: Extended Data Table 2: Binding characterization using Isothermal Titration Calorimetry. In all assessments the protein and ligand concentrations were 150 μM and 2 mM, respectively.

Figure 7

| Protein | Biapenem (MW = 350.4) | Faropenem (MW = 285.3) | Tebipenem (MW = 383.5) |
|---|---|---|---|
| wild-type | +138 | +86 | +339, +383 |
| Y318A | No adduct | +86 | +339, +383 |
| Y318F | No adduct | +86 | +339, +383 |
| H336A | No adduct | No adduct | No adduct |
| H336N | No adduct | No adduct | No adduct |
| H352A | No adduct | +86 | +339, +383 |
| H352N | No adduct | +86 | n.d. |
| C354A | No adduct | No adduct | No adduct |
| C354S | No adduct | No adduct | No adduct |

FIGURE 7: Extended Data Table 3: Mass-spectrometric analysis of adducts formed from reaction between L,D-transpeptidase $Ldt_{Mt2}$ (wild-type), mutant $Ldt_{Mt2}$ with single amino acid substitutions and Biapenem, Faropenem and Tebipenem. Molecular weights (MW) of detected adducts are shown (in daltons). Not determined (n.d.).

Figure 8

| | Ldt$_{Mt2}$ | Ldt$_{Mt2}$-Faropenem | Ldt$_{Mt2}$-Doripenem | Ldt$_{Mt1}$-apo | Ldt$_{Mt1}$-Faropenem |
|---|---|---|---|---|---|
| Data Collection | | | | | |
| Beamline | APS/SBC-19ID | in-house CuKα Rigaku | in-house CuKα Rigaku | APS/SBC-19ID | APS/SBC-19ID |
| Space group | P1 | P 1 21 1 | P 1 21 1 | P31 | P31 |
| Cell Dimensions | | | | | |
| a, b, c (Å) | 61.64, 75.53, 94.14 | 61.05, 93.9, 75.2 | 60.87, 93.06, 75.21 | 57.73, 57.73, 256.6 | 58.38, 58.38, 257.4 |
| α, β, γ (°) | 89.04, 89.96, 92.76 | 90.0, 92.7, 90.0 | 90.0, 92.91, 90.0 | 90.0, 90.0, 120.0 | 90.0, 90.0, 120.0 |
| Resolution (Å) | 50.0-1.79 (1.83-1.79)* | 50.0-2.17 (2.21-2.17) | 41.3-2.18 (2.22-2.18) | 24.5-1.89 (1.92-1.89) | 19.88-2.25(2.29-2.25) |
| R$_{merge}$ (%) | 6.8 (43.7) | 6.4 (18.6) | 6.1 (21.8) | 11.9 (53.7) | 5.3 (26.5) |
| I/σ(I) | 14.9 (2.39) | 20.7 (4.22) | 15.84 (2.69) | 18.61(5.73) | 24.48 (4.0) |
| Completeness (%) | 97.3 (96.1) | 94.6 (59.7) | 99.7 (95.5) | 98.6 (100.0) | 93.8 (90.9) |
| Multiplicity | 3.7 (3.8) | 3.6 (3.0) | 3.7 (2.7) | 13.0 (12.5) | 6.6 (3.1) |
| Refinement | | | | | |
| Resolution (Å) | 50.0-1.79 (1.83-1.79)* | 50.0-2.17 (2.21-2.17) | 41.32-2.18 (2.22-2.18) | 24.5-1.89 (1.92-1.89) | 19.88-2.25(2.29-2.25) |
| No. reflections | 162100 | 40491 | 43902 | 71314 | 40802 |
| R$_{work}$ / R$_{free}$ | 0.18 / .22 | 0.18 / 0.23 | 0.19 / 0.22 | 0.21 / 0.26 | 0.24 / 0.28 |
| Total no. of atoms | 12407 | 5790 | 5545 | 6224 | 5886 |
| B-factor (Å$^2$) | | | | | |
| Protein | 18.0 | 26.82 | 24.0 | 17.0 | 27.0 |
| Active site ligand | | 35.8 | 31.4 | | 23.67 |
| R.m.s deviations | | | | | |
| Bonds lengths (Å) | 0.02 | 0.02 | 0.01 | .01 | .01 |
| Bond angles (°) | 1.99 | 1.94 | 1.22 | 1.42 | 1.09 |

* Values in the parentheses are for highest resolution

FIGURE 8: Extended Data Table 4: Data collection and refinement statistics.

Figure 9

| | Ldt$_{Mt2}$-T206_A | Ldt$_{Mt2}$-T206_B | Ldt$_{Mt2}$-T208 | Ldt$_{Mt2}$-T210 |
|---|---|---|---|---|
| Data Collection | | | | |
| Beamline | APS/SBC-19ID | APS/SBC-19ID | APS/SBC-19ID | APS/SBC-19ID |
| Space group | P2$_1$ | P2$_1$ | P2$_1$ | P2$_1$ |
| Cell Dimensions (Å) a, b, c (Å) α, β, γ (°) | 61.02, 93.95, 75.44 90.0, 93.0, 90.0 | 61.52, 93.88, 75.32 90.0, 92.78, 90.0 | 61.28, 93.87, 75.36 90.0, 93.07, 90.0 | 61.18, 93.96, 75.39 90.0, 93.04, 90.00 |
| Resolution (Å) | 50.0-2.10 (2.14-2.10) | 50.0-2.20 (2.24-2.20) | 50.0-1.85 (1.88-1.85) | 50.0-2.0 (2.03-2.00) |
| R$_{merge}$ (%) | 9.2 (51.6) | 12.0 (52.1) | 6.9 (45.8) | 9.0 (42.9) |
| I/σ(I) | 17.96 (3.72) | 15.80 (2.96) | 23.8 (4.92) | 19.95 (6.4) |
| Completeness (%) | 100 (100) | 99.6 (99.0) | 99.0 (97.8) | 98.6 (97.2) |
| Multiplicity | 6.3(6.2) | 6.9 (6.2) | 7.3(7.2) | 7.4 (7.4) |
| Refinement | | | | |
| Resolution (Å) | 50.0-2.10 (2.14-2.10) | 50.0-2.20 (2.24-2.20) | 37.24-1.85 (1.88-1.85) | 50.0-2.0 (2.03-2.00) |
| No. reflections | 49937 | 43816 | 71306 | 56418 |
| R$_{work}$ / R$_{free}$ | 0.19 / 0.24 | 0.18 / 0.23 | 0.19 / 0.23 | 0.20 / 0.25 |
| Total no. of atoms | 5950 | 5930 | 5722 | 5616 |
| B-factor (Å$^2$) | | | | |
| Protein | 31.38 | 31.41 | 28.19 | 26.06 |
| Active site ligand | 50.40 | 50.54 | 76.42 | 78.4 |
| R.m.s deviations | | | | |
| Bonds lengths (Å) | 0.02 | 0.02 | 0.02 | 0.02 |
| Bond angles (°) | 2.04 | 1.92 | 2.10 | 2.07 |

* Values in the parentheses are for highest resolution

FIGURE 9: Extended Data Table 5: Data collection and refinement statistics.

```
LdtMt2
LdtMt2    1  MPKVGIAAQAGRTRV....RRAWLTALMMTAVMIGAVA.CGSGRGPAPIKVIADKGTPFA
LdtMab1
LdtMab2   1  MTQ.......GRPRLHAGARRRWVATLALPVVAMAVLAGCAGATTQEPPKVI.DKATPYA
LdtKp
LdtCl
LdtPa
```

```
              β1          β2     β3        β4      β5
LdtMt2       ───▶  TT    TT  ───▶  ───▶  TT ───▶  TT ───▶

LdtMt2   56  DLLVPKLTASVTDGAVGVTVDAPVSVTAADGVLAAVTMVNDNGRPVAGRLSPDGLRWSTT
LdtMab1
LdtMab2  53  DLLVPKLAMSVKDGAVGVAVDAPVTVTAGEGVLGSVTMVNSDGKEIAGEIGPDGVTWTTT
LdtKp
LdtCl
LdtPa
```

```
                       β6       β7       β8  β9      β10
LdtMt2       TT  ───▶  TT  ───▶      ───▶ ───▶  TT ───▶  TT

LdtMt2   116 EQLGYNRRYTLNATALGLGGAATRQLTFQ...TSSPAHLTMPYVMPGDGE.VVGGVEPVA
LdtMab1    1 ......MLVVTGLVSLLMNAAVTAPATLGHALAASPSGVAS..VSPTPGQ.TVGVAMPVT
LdtMab2  113 EPLGYDKQYTINADARGLGGVARANATFR...TQSPDNMTMPYVMPGDGE.VVGVGQTVA
LdtKp      1 ................MKRKTNITLALLSALGASTAAWAVDYPLPPANSRLIGQNQYWT
LdtCl      1 ................MKRASLITLLLLGSLGALNSASAMDYPLPPAGSRLIGQNQTTI
LdtPa      1 ...............MLSRVPVVSLSFA.ALLSAGSASALELQLPPPGEDVVGQVQVIK
```

```
           β11      α1    β12     β13     β14       β15
LdtMt2    ───▶           ───▶   ───▶   ───▶   TT  ───▶

LdtMt2  172 IRFDEN....IADRGAAEKAIKITTNPPVEGAFYWLNNREVRWRPEHFWKPGTAVDVAVN
LdtMab1  52 IRFAAP....VADRIAAERSIEFSAPKVPAGAFSWVDNATVRFTPREYWPAHSSITVSVN
LdtMab2 169 IRFDEN....IPNRAAAEKAIKITTNPPVEGAFYWLNNREVRWRPESFWDSGTSVDVKVN
LdtKp    44 VQEGDRNLQAIARHFDTAAMLILEANDTIAPVQP..............KPGTQVLIPSQ
LdtCl    44 IQEGDTKLQTIARRFNTAAQLILETNNTIAPVNP..............APGTVITIPSQ
LdtPa    44 AKYEDT.FADLGEQYNLGYSEMVAANPGVDPWLPGV.............GTEVIIPTR
```

FIG. 10

```
LdtMt2             β16         β17        β18         β19       β20
                TT ──▶      ───▶        ───▶        ───▶TT ───▶             TT
LdtMt2  228  TYGVDLGEGMFGEDNVQTHFTIGDEVIATADDNTKILTVRVNGEVVKSMPTSMGKDSTPT
LdtMab1 108  ..........GVSGMKYKFQTGSEVLGIGSISGHTFTVKIDGTVMRTMPASMGKDKHPT
LdtMab2 225  TYGVNLGDGVFGQDNVASHFTIGDAVISRVDDTNKILNIERNGEIIKTMPTSMGKDKAPT
 LdtKp   89  MLLPD..............VPREGIVVNLAELRLYYFPPGENQVQVYPLGIGQLGLET
 LdtCl   89  MLLPD..............TPREGIVVNLAELRLYYYPPGGNIVQVFPLGIGQLGLET
 LdtPa   88  FVLPP..............GPREGVVINLAEYRLYYYPKGQNVVHTYPLGIGREGWGS

LdtMt2           β21          β22       η1                           β23
                ───▶         ───▶     ─▶ℓℓℓℓ    T........T   TT   ───▶       T.
LdtMt2  288  ANGIYIVGSRYKH........IIMDSSTYGVPV.......NSPNGYRTDVDWATQISY.
LdtMab1 157  PVGSFTALEKQSP........VVMDSRTIGIPL.......NDPEGYKLTVYYAVRVTW.
LdtMab2 285  NNGTYIIGERFKD........LIMDSSTYGVAV.......NSPDGYRTKVQYATQMSY.
 LdtKp  133  PEMTTRVGQKIPNPTWTPTAGIRARSLEKGVTLPAVVPAGPNNPLG....RYALRLAYG
 LdtCl  133  PVTTTRVSQKIPNPTWTPTGIRARSLEQGIKLPPVVPAGPNNPLG....RFALRLGVG
 LdtPa  132  PIANTRITAKTKDPAWYPPASIRAEHAADGDPLPTVVPPGDNPLG....PYKLTLGV.

LdtMt2          β24  η2       β25          α2             β26
              .T ──▶ ℓℓℓ    ───▶   ℓℓℓℓℓℓℓℓℓ    TT    ───▶         T
LdtMt2  331  .SGVFVHSAPWSVGAQGHTNTSHGCLNVSPSNAQWFYDHVKRGDIVEVYN..TVGGTLPG
LdtMab1 200  .GGYVVHSAPWSTGAQGNSNVSHGCINLSPDNASWYYNTVSIGDPIIINA........
LdtMab2 328  .SGIYVHAAPWSVGAQGRTNTSHGCLNVSTANAKWFYENTKRGSVVISN..TVGPVLPG
 LdtKp  188  NGETLIHGTNAPDS..VGLRVSSGCMRMNADDIKALFSQVKTGTPVRIINQPVKFAVEPD
 LdtCl  188  NGEYLIHGTSAPDS..VGLRVSSGCMRMNAPDIKALFEQVRVGTRVQIINEPVKFSVEPD
 LdtPa  186  .PGYLIHGSNKKFG..IGTRTSHGCFRMYNADVTHLFSMISVGTSVRIINEPYKFGVS.N

LdtMt2              η3    α3
                 T  ℓℓℓ  ℓℓℓℓℓ ℓ
LdtMt2  388  IDGLGDWNIPWDQWR.AGN....AKA......................
LdtMab1     ................................................
LdtMab2 385  TEGLGDWNIPWAQWK.AGN....ARQQ.....................
 LdtKp  246  GKRYVEVHRPLSQ..TEGE....NTRTIAYTLPAAFHAFAEDKAVDDLQLKKAMSRRAGY
 LdtCl  246  GKRYIEVHRPLAQ..VEGE....NPQITPITHSADFASFVSQAGSDKALIDKALSRRAGI
 LdtPa  242  GKVVYLEAHTPLND...HGDPSVVDKHTAVINTLLKRDDLAKRIQLNWDVVREVVASEDGV
```

FIG. 10 Continued

FIGURE 13: Extended Data Figure 4: Core structure common to carbapenems.

FIGURE 14: Extended Data Figure 5: X-ray crystal structures of Apo $Ldt_{Mt2}$ (5a) and $Ldt_{Mt1}$ (5b).

FIGURE 15: Extended Data Figure 6: Gross pathology of lungs of all mice infected with *M. tuberculosis* that received various treatments. (a) no treatment, (b) isoniazid, (c) rifampicin, (d) isoniazid + rifampicin, (e) biapenem, (f) biapenem + rifampicin, (g) faropenem, (h) faropenem + rifampicin.

Figure 18
Extended Data Figure 9

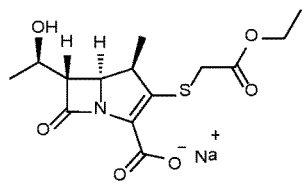

T201 sodium (4R,5S,6S)-3-((2-ethoxy-2-oxoethyl)thio)-6-((R)-1-hydroxyethyl)-4-methyl-7-oxo-1-azabicyclo[3.2.0]hept-2-ene-2-carboxylate was prepared as a white solid according to the general procedure A: $^1$H NMR (600 MHz, D$_2$O) δ 4.29 – 4.18 (m, 4), 3.79 (d, $J$ = 15.5 Hz, 1), 3.54 (d, $J$ = 15.6 Hz, 1), 3.52 – 3.47 (m, 1), 3.46 (dd, $J$ = 6.1, 2.4 Hz, 1), 1.31 (d, $J$ = 6.4 Hz, 3), 1.27 (t, $J$ = 7.1 Hz, 3), 1.20 (d, $J$ = 7.3 Hz, 3). An additional peak was noted at 2.24 (s).

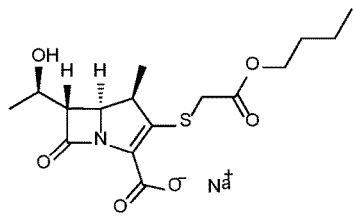

T202 sodium (4R,5S,6S)-3-((2-butoxy-2-oxoethyl)thio)-6-((R)-1-hydroxyethyl)-4-methyl-7-oxo-1-azabicyclo[3.2.0]hept-2-ene-2-carboxylate was prepared as a white solid according to the general procedure A: $^1$H NMR (600 MHz, D$_2$O) δ 4.12 – 4.07 (m, 1), 4.05 (t, $J$ = 6.3 Hz, 2), 4.03 (dd, $J$ = 9.1, 2.5 Hz, 1), 3.62 (d, $J$ = 15.5 Hz, 1), 3.37 – 3.34 (m, 1), 3.34 – 3.32 (m, 1), 3.28 (dd, $J$ = 6.2, 2.5 Hz, 1), 1.51 – 1.45 (m, 2), 1.24 – 1.17 (m, 2), 1.15 (d, $J$ = 6.4 Hz, 3), 1.03 (d, $J$ = 7.3 Hz, 3), 0.74 (t, $J$ = 7.4 Hz, 3).

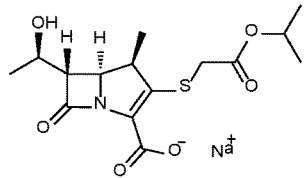

T203 sodium (4R,5S,6S)-6-((R)-1-hydroxyethyl)-3-((2-isopropoxy-2-oxoethyl)thio)-4-methyl-7-oxo-1-azabicyclo[3.2.0]hept-2-ene-2-carboxylate was prepared as a white solid according to the general procedure A: $^1$H NMR (600 MHz, D$_2$O) δ 4.87 (dt, $J$ = 12.6, 6.3 Hz, 1), 4.13 – 4.07 (m, 1), 4.05 (dd, $J$ = 9.2, 2.5 Hz, 1), 3.58 (d, $J$ = 15.2 Hz, 1), 3.39 – 3.32 (m, 1), 3.32 – 3.26 (m, 2), 1.15 (d, $J$ = 6.4 Hz, 3), 1.10 (t, $J$ = 5.7 Hz, 6), 1.03 (d, $J$ = 7.3 Hz, 3).

Figure 18 continued

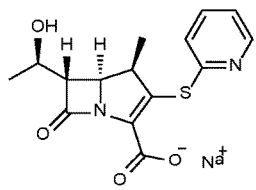

T204 sodium (4R,5S,6S)-6-((R)-1-hydroxyethyl)-4-methyl-7-oxo-3-(pyridin-2-ylthio)-1-azabicyclo[3.2.0]hept-2-ene-2-carboxylate was prepared as a white solid according to the general procedure A: $^1$H NMR (600 MHz, D$_2$O) δ 8.32 (d, $J$ = 4.8 Hz, 1), 7.69 (t, $J$ = 7.7 Hz, 1), 7.48 (d, $J$ = 7.8 Hz, 1), 7.26 – 7.20 (m, 1), 4.14 – 4.05 (m, 2), 3.30 (d, $J$ = 6.4 Hz, 1), 3.15 – 3.07 (m, 1), 1.12 (d, $J$ = 6.3 Hz, 3), 0.85 (d, $J$ = 7.2 Hz, 3).

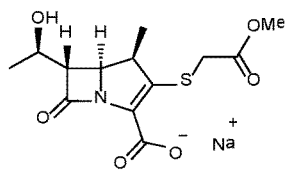

T205 sodium (4R,5S,6S)-6-((R)-1-hydroxyethyl)-3-((2-methoxy-2-oxoethyl)thio)-4-methyl-7-oxo-1-azabicyclo[3.2.0]hept-2-ene-2 carboxylate : $^1$H NMR (600 MHz, D$_2$O) δ 4.13 – 4.07 (m, 1), 4.05 (dd, $J$ = 9.1, 2.5 Hz, 1), 3.66 – 3.59 (m, 4), 3.43 (d, $J$ = 15.7 Hz, 1), 3.32 – 3.25 (m, 2), 1.15 (d, $J$ = 6.4 Hz, 3), 1.02 (d, $J$ = 7.3 Hz, 3).

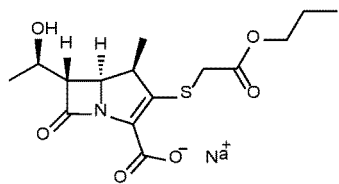

T206 sodium (4R,5S,6S)-6-((R)-1-hydroxyethyl)-4-methyl-7-oxo-3-((2-oxo-2-propoxyethyl)thio)-1-azabicyclo[3.2.0]hept-2-ene-2-carboxylate was prepared as a white solid according to the general procedure A: $^1$H NMR (600 MHz, D$_2$O) δ 4.12 – 4.07 (m, 1), 4.04 (dd, $J$ = 9.3, 2.2 Hz, 1), 4.00 (t, $J$ = 6.5 Hz, 2), 3.63 (d, $J$ = 15.5 Hz, 1), 3.36 (d, $J$ = 15.5 Hz, 1), 3.34 – 3.27 (m, 2), 1.55 – 1.48 (m, 2), 1.15 (d, $J$ = 6.4 Hz, 3), 1.04 (d, $J$ = 7.2 Hz, 3), 0.77 (t, $J$ = 7.4 Hz, 3).

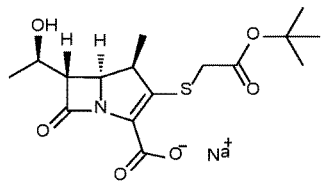

Figure 18 continued

T207 sodium (4R,5S,6S)-3-((2-(tert-butoxy)-2-oxoethyl)thio)-6-((R)-1-hydroxyethyl)-4-methyl-7-oxo-1-azabicyclo[3.2.0]hept-2-ene-2-carboxylate was prepared as a white solid according to the general procedure A: $^1$H NMR (600 MHz, D$_2$O) δ 4.10 (m, 1), 4.06 (dd, J = 9.3, 2.6 Hz, 1), 3.53 (d, J = 15.2 Hz, 1), 3.36 (m, 1), 3.31 (dd, J = 6.2, 2.6 Hz, 1), 3.18 (d, J = 15.2 Hz, 1), 1.31 (s, 9), 1.15 (d, J = 6.4 Hz, 3), 1.04 (d, J = 7.3 Hz, 3).

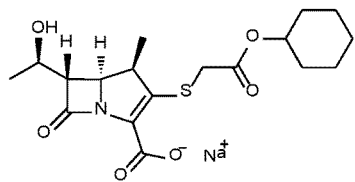

T208 sodium (4R,5S,6S)-3-((2-(cyclohexyloxy)-2-oxoethyl)thio)-6-((R)-1-hydroxyethyl)-4-methyl-7-oxo-1-azabicyclo[3.2.0]hept-2-ene-2-carboxylate was prepared as a white solid according to the general procedure A: $^1$H NMR (600 MHz, D$_2$O) δ 4.72 – 4.65 (m, 1), 4.14 – 4.07 (m, 1), 4.04 (d, J = 9.3 Hz, 1), 3.62 (d, J = 15.3 Hz, 1), 3.41 – 3.33 (m, 1), 3.32 – 3.25 (m, 2), 1.69 – 1.59 (m, 2), 1.57 – 1.46 (m, 2), 1.43 – 1.29 (m, 3), 1.28 – 1.17 (m, 3), 1.15 (d, J = 6.4 Hz, 3), 1.05 (d, J = 7.3 Hz, 3).

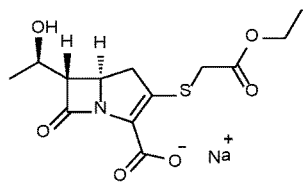

T209 sodium (5R,6S)-3-((2-ethoxy-2-oxoethyl)thio)-6-((R)-1-hydroxyethyl)-7-oxo-1-azabicyclo[3.2.0]hept-2-ene-2-carboxylate: $^1$H NMR (600 MHz, D$_2$O) δ 4.13 – 4.01 (m, 4), 3.59 (d, J = 16.3 Hz, 1), 3.50 (d, J = 16.4 Hz, 1), 3.25 (dd, J = 6.0, 2.6 Hz, 1), 3.10 (dd, J = 17.3, 9.7 Hz, 1), 2.95 (dd, J = 17.3, 8.6 Hz, 1), 1.17 – 1.05 (m, 6).

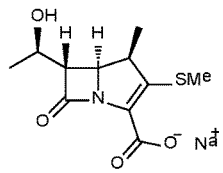

T210 sodium (5R,6S)-6-((R)-1-hydroxyethyl)-3-((2-methoxy-2-oxoethyl)thio)-7-oxo-1-azabicyclo[3.2.0]hept-2-ene-2-carboxylate was prepared as a white solid according to the general procedure A: $^1$H NMR (600 MHz, D$_2$O) δ 4.09 (p, J = 6.3 Hz, 1), 4.01 (dd, J = 8.8, 2.3 Hz, 1), 3.33 (dq, J = 14.6, 7.2 Hz, 1), 3.24 (dd, J = 6.4, 2.3 Hz, 1), 2.21 (s, 3), 1.16 (d, J = 6.4 Hz, 3), 1.04 (d, J = 7.3 Hz, 3).

Figure 18 continued

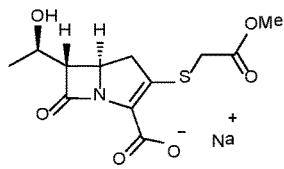

T211 sodium (5R,6S)-6-((R)-1-hydroxyethyl)-3-((2-methoxy-2-oxoethyl)thio)-7-oxo-1-azabicyclo[3.2.0]hept-2-ene-2-carboxylate was prepared as a white solid according to the general procedure B: $^1$H NMR (600 MHz, D$_2$O) δ 4.11 – 4.01 (m, 2), 3.63 (s, 3), 3.60 (d, $J$ = 16.6 Hz, 1), 3.54 (d, $J$ = 16.5 Hz, 1), 3.25 (dd, $J$ = 5.9, 2.6 Hz, 1), 3.08 (dd, $J$ = 17.3, 9.7 Hz, 1), 2.95 (dd, $J$ = 17.3, 8.5 Hz, 1), 1.13 (d, $J$ = 6.4 Hz, 3).

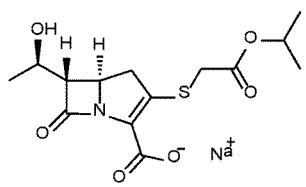

T212 sodium (5R,6S)-6-((R)-1-hydroxyethyl)-3-((2-isopropoxy-2-oxoethyl)thio)-7-oxo-1-azabicyclo[3.2.0]hept-2-ene-2-carboxylate was prepared as a white solid according to the general procedure B: $^1$H NMR (600 MHz, D$_2$O) δ 4.95 – 4.82 (m, 1), 4.11 – 3.99 (m, 2), 3.56 (d, $J$ = 16.1 Hz, 1), 3.44 (d, $J$ = 16.1 Hz, 1), 3.25 (dd, $J$ = 6.0, 2.5 Hz, 1), 3.12 (dd, $J$ = 17.4, 9.7 Hz, 1), 2.95 (dd, $J$ = 17.3, 8.5 Hz, 1), 1.14 (d, $J$ = 6.6 Hz, 3), 1.12 (d, $J$ = 6.3 Hz, 6).

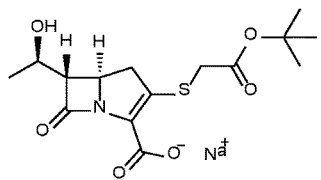

T213 sodium (5R,6S)-3-((2-(tert-butoxy)-2-oxoethyl)thio)-6-((R)-1-hydroxyethyl)-7-oxo-1-azabicyclo[3.2.0]hept-2-ene-2-carboxylate was prepared as a white solid according to the general procedure B: $^1$H NMR (600 MHz, D$_2$O) δ 4.12 – 3.97 (m, 2), 3.50 (d, $J$ = 16.0 Hz, 1), 3.36 (d, $J$ = 16.0 Hz, 1), 3.24 (dd, $J$ = 6.0, 2.6 Hz, 1), 3.12 (dd, $J$ = 17.3, 9.7 Hz, 1), 2.94 (dd, $J$ = 17.4, 8.6 Hz, 1), 1.32 (s, 9), 1.14 (d, $J$ = 6.4 Hz, 3). An additional peak was noted as 2.6 (s).

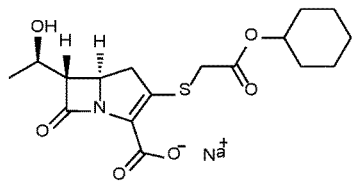

Figure 18 continued

T214 sodium (5R,6S)-3-((2-(cyclohexyloxy)-2-oxoethyl)thio)-6-((R)-1-hydroxyethyl)-7-oxo-1-azabicyclo[3.2.0]hept-2-ene-2-carboxylate was prepared as a white solid according to the general procedure B: $^1$H NMR (600 MHz, D$_2$O) δ 4.76 – 4.67 (m, 1), 4.13 – 4.00 (m, 2), 3.57 (d, J = 16.1 Hz, 1), 3.45 (d, J = 16.1 Hz, 1), 3.24 (dd, J = 6.0, 2.5 Hz, 1), 3.14 (dd, J = 17.4, 9.8 Hz, 1), 2.97 (dd, J = 17.3, 8.5 Hz, 1), 1.70 – 1.60 (m, 2), 1.57 – 1.46 (m, 2), 1.41 – 1.30 (m, 3), 1.30 – 1.17 (m, 3), 1.13 (d, J = 6.4 Hz, 3). 1 H was not accounted for in the spectrum.

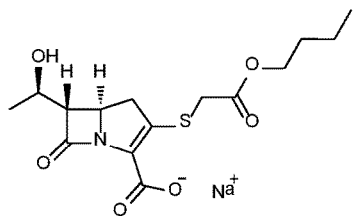

T215 sodium (5R,6S)-3-((2-butoxy-2-oxoethyl)thio)-6-((R)-1-hydroxyethyl)-7-oxo-1-azabicyclo[3.2.0]hept-2-ene-2-carboxylate was prepared as a white solid according to the general procedure B: $^1$H NMR (600 MHz, D$_2$O) δ 4.17 – 3.98 (m, 4), 3.58 (d, J = 16.3 Hz, 1), 3.49 (d, J = 16.2 Hz, 1), 3.27 – 3.19 (m, 1), 3.12 (dd, J = 17.4, 9.8 Hz, 1), 2.96 (dd, J = 17.3, 8.5 Hz, 1), 1.56 – 1.42 (m, 2), 1.22 (dd, J = 14.7, 7.3 Hz, 2), 1.13 (d, J = 6.3 Hz, 3), 0.75 (t, J = 7.4 Hz, 3). 1 H was not accounted for in spectrum. Also noted 7.3 (m), 7.1 (m), 2.6 (s), 2.2 (m), 1.1 (m).

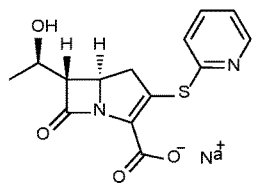

T216 sodium (5R,6S)-6-((R)-1-hydroxyethyl)-7-oxo-3-(pyridin-2-ylthio)-1-azabicyclo[3.2.0]hept-2-ene-2-carboxylate was prepared as a white solid according to the general procedure B: $^1$H NMR (600 MHz, D$_2$O) δ 8.38 – 8.32 (m, 1), 7.75 – 7.66 (m, 1), 7.51 (d, J = 7.9 Hz, 1), 7.27 (dd, J = 6.8, 5.7 Hz, 1), 4.12 – 3.97 (m, 2), 3.26 – 3.15 (m, 1), 2.77 – 2.64 (m, 2), 1.09 (dd, J = 6.4, 1.3 Hz, 3). 1 H was not accounted for in the spectrum. Also noted 2.1 (s), 1.0 (m).

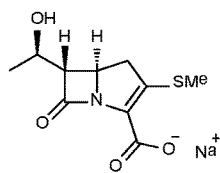

T217 sodium (5R,6S)-6-((R)-1-hydroxyethyl)-3-(methylthio)-7-oxo-1-azabicyclo[3.2.0]hept-2-ene-2-carboxylate was prepared as a white solid according to the general procedure B: $^1$H NMR (600 MHz,

Figure 18 continued

D₂O) δ 4.13 – 3.94 (m, 2), 3.30 – 3.19 (m, 1), 3.19 – 3.09 (m, 1), 3.04 – 2.94 (m, 1), 2.19 (s, 3), 1.14 (d, $J$ = 3.9 Hz, 3). 1 H not accounted for in the spectrum.

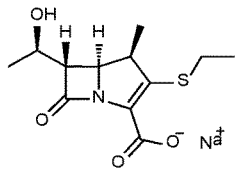

T218 sodium (4R,5S,6S)-3-(ethylthio)-6-((R)-1-hydroxyethyl)-4-methyl-7-oxo-1-azabicyclo[3.2.0]hept-2-ene-2-carboxylate was prepared as a white solid according to the general procedure A: ¹H NMR (500 MHz, D₂O) δ 4.16 (p, $J$ = 6.3 Hz, 1), 4.10 (dd, $J$ = 8.9, 2.4 Hz, 1), 3.37 (dq, $J$ = 14.7, 7.3 Hz, 1), 3.32 (dd, $J$ = 6.3, 2.4 Hz, 1), 2.82 (dq, $J$ = 14.6, 7.3 Hz, 1), 2.73 – 2.62 (m, 1), 1.22 (d, $J$ = 6.4 Hz, 3), 1.19 (t, $J$ = 7.4 Hz, 3), 1.11 (d, $J$ = 7.3 Hz, 3).

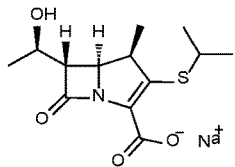

T219 sodium (4R,5S,6S)-6-((R)-1-hydroxyethyl)-3-(isopropylthio)-4-methyl-7-oxo-1-azabicyclo[3.2.0]hept-2-ene-2-carboxylate was prepared as a white solid according to the general procedure A: ¹H NMR (500 MHz, D₂O) δ 4.20 – 4.14 (m, 1), 4.12 (dd, $J$ = 9.1, 2.5 Hz, 1), 3.41 – 3.35 (m, 1), 3.34 (dd, $J$ = 6.2, 2.5 Hz, 1), 3.32 – 3.26 (m, 1), 1.22 (d, $J$ = 6.4 Hz, 6), 1.19 (d, $J$ = 6.9 Hz, 3), 1.12 (d, $J$ = 7.3 Hz, 3). 1 H was not accounted for in the spectrum.

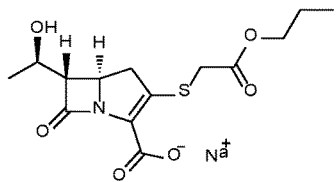

T220 sodium (5R,6S)-6-((R)-1-hydroxyethyl)-7-oxo-3-((2-oxo-2-propoxyethyl)thio)-1-azabicyclo[3.2.0]hept-2-ene-2-carboxylate was prepared as a white solid according to the general procedure B: ¹H NMR (600 MHz, D₂O) δ 4.10 – 4.03 (m, 2), 4.01 (t, $J$ = 6.5 Hz, 2), 3.59 (d, $J$ = 16.3 Hz, 1), 3.50 (d, $J$ = 16.4 Hz, 1), 3.24 (d, $J$ = 5.9 Hz, 1), 3.12 (dd, $J$ = 17.2, 9.7 Hz, 1), 2.96 (dd, $J$ = 16.8, 8.4 Hz, 1), 1.56 – 1.49 (m, 2), 1.13 (d, $J$ = 6.4 Hz, 3), 0.77 (td, $J$ = 7.4, 1.2 Hz, 3).

Figure 18 continued

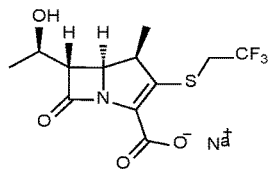

T221 sodium (4R,5S,6S)-6-((R)-1-hydroxyethyl)-4-methyl-7-oxo-3-((2,2,2-trifluoroethyl)thio)-1-azabicyclo[3.2.0]hept-2-ene-2-carboxylate was prepared as a white solid according to the general procedure A: $^1$H NMR (500 MHz, D$_2$O) δ 4.26 – 4.11 (m, 2), 3.73 – 3.56 (m, 1), 3.50 – 3.31 (m, 3), 1.24 (d, $J$ = 5.9 Hz, 3), 1.13 (d, $J$ = 7.1 Hz, 3). The O-H was not observed, possibly due to facile H-D exchange with the solvent.

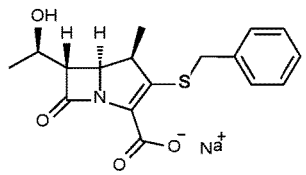

T222 sodium (4R,5S,6S)-3-(benzylthio)-6-((R)-1-hydroxyethyl)-4-methyl-7-oxo-1-azabicyclo[3.2.0]hept-2-ene-2-carboxylate was prepared as a white solid according to the general procedure A: $^1$H NMR (500 MHz, D$_2$O) δ 7.53 – 7.21 (m, 5), 4.25 – 4.03 (m, 2), 4.06 – 3.90 (m, 2), 3.46 – 3.23 (m, 2), 1.39 – 1.18 (m, 3), 1.18 – 1.02 (m, 3). The O-H was not observed, possibly due to facile H-D exchange with the solvent.

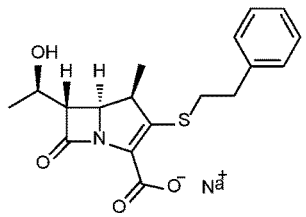

T223 sodium (4R,5S,6S)-6-((R)-1-hydroxyethyl)-4-methyl-7-oxo-3-(phenethylthio)-1-azabicyclo[3.2.0]hept-2-ene-2-carboxylate was prepared as a white solid according to the general procedure A: $^1$H NMR (500 MHz, D$_2$O) δ 7.47 – 7.16 (m, 5), 4.26 – 4.06 (m, 1), 3.81 (d, $J$ = 8.7 Hz, 1), 3.33 – 3.23 (m, 1), 3.21 – 3.05 (m, 2), 3.03 – 2.78 (m, 3), 1.21 (d, $J$ = 6.2 Hz, 3), 1.04 (d, $J$ = 7.1 Hz, 3). The O-H was not observed, possibly due to facile H-D exchange with the solvent.

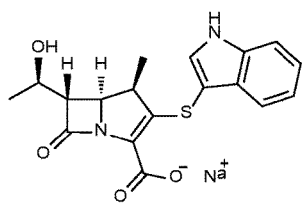

Figure 18 continued

T224 sodium (4R,5S,6S)-3-((1H-indol-3-yl)thio)-6-((R)-1-hydroxyethyl)-4-methyl-7-oxo-1-azabicyclo[3.2.0]hept-2-ene-2-carboxylate was prepared as a white solid according to the general procedure A: $^1$H NMR (500 MHz, D$_2$O) δ 7.68 (d, $J$ = 7.3 Hz, 1), 7.62 (s, 1), 7.54 (d, $J$ = 7.2 Hz, 1), 7.32 – 7.25 (m, 1), 7.26 – 7.18 (m, 1), 4.17 – 4.02 (m, 1), 3.91 (d, $J$ = 9.2 Hz, 1), 3.25 – 3.12 (m, 1), 2.69 – 2.57 (m, 1), 1.13 (d, $J$ = 4.7 Hz, 3), 0.90 (d, $J$ = 6.4 Hz, 3).The N-H and O-H were not observed, possibly due to facile H-D exchange with the solvent.

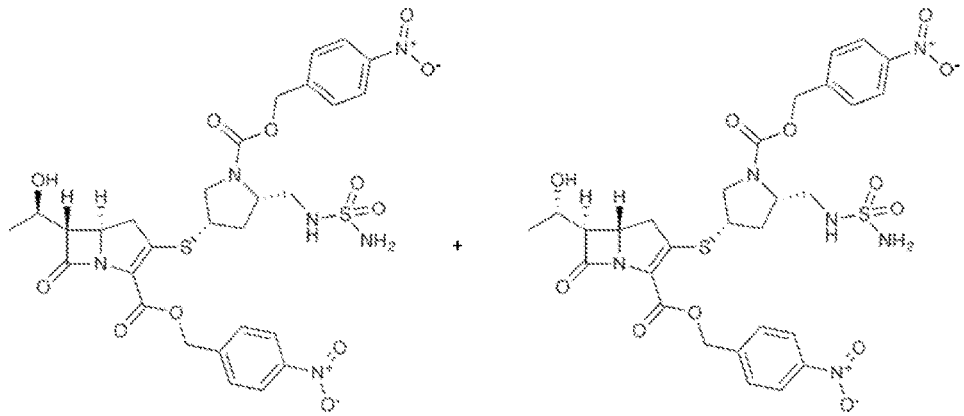

(5R,6S,8R)-Des-1β-methyl-doripenem p-nitrobenzyl ester and (5S,6R,8S)-Des-1β-methyl-doripenem p-nitrobenzyl ester: The title compound was synthesized as by Nishino *et al*. To a solution of (±)-4-nitrobenzyl 6-(1-hydroxyethyl)-3,7-dioxo-1-azabicyclo[3.2.0]heptane-2-carboxylate (159mg, 0.457 mmol) in acetonitrile (11.4 mL) was added diphenylchlorophosphate (105 μL, 0.503 mmol) and diisopropylethylamine (88 μL, 0.503 mmol) and stirred for 1h at 0°C. A solution of 4-nitrobenzyl (2S,4S)-4-thio-2-[[N-sulfamoylamino]methyl]pyrrolidine -1-carboxylate (258 mg, 0.685 mmol) and diisopropylethylamine (127 μL, 0.731 mmol) in acetonitrile (3 mL) was added to the previous mixture and stirred for 2h at 0°C. When complete, the reaction mixture was diluted with ethyl acetate, washed three times with a solution of K$_2$HPO$_4$ in water (100 mM, pH = 7.4), washed with brine, filtered and concentrated *in vacuo*. The resulting oil was purified by silica gel chromatography (5:95 MeOH:CH$_2$Cl$_2$) to provide a white foam (80 mg, 24%). $^1$H NMR (400 MHz, MeOD); δ 8.21 (d, $J$ = 8.6 Hz, 4H), 7.68 (d, $J$ = 9.0 Hz, 2H), 7.61 (d, $J$ = 8.9 Hz, 2H), 5.44, 5.24 (ABq, $J$ = 14.2, 2H), 5.23 (s, 2H), 5.08-5.19 (m, 2H), 4.15-4.25 (m, 1H), 3.99-4.15 (m, 3H), 3.66-3.81 (m, 1H), 3.17-3.35 (m, 5H), 3.12-3.17 (m, 1H), 1.20 (d, $J$ = 6.2, 3H).

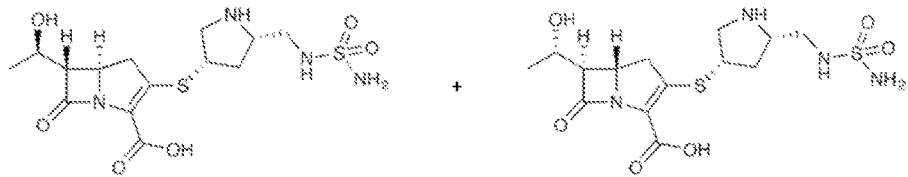

(5R,6S,8R)-Des-1β-methyl-doripenem and (5S,6R,8S)-Des-1β-methyl-doripenem

Hydrogenolysis of a solution of the des-1β-methyl-doripenem p-nitrobenzyl ester in tetrahydrofuran (2 mL) and 0.5 M $K_2HPO_4$ (2 mL, pH = 7.4) was performed at 40 psi for 30 min with 100% w/w Pd/C in a Parr-shaker apparatus. The resulting solution was extracted with $Et_2O$ and the aqueous layer was filtered through a 0.2 μm nylon syringe filter. The product mixture was purified by HPLC (10:90 acetonitrile: 5 mM $NH_4HCO_3$ in water) and lyophilized to provide the title compound as a white powder. $^1$H NMR (400 MHz, $D_2O$); δ 4.17-4.25 (m, 2H), 4.02 (dd, $J$ = 7.4, 5.3 Hz, 1H), 3.83-3.92 (m, 1H), 3.74 (dd, $J$ = 12.3, 8.3 Hz, 1H), 3.48 (d, $J$ = 4.7 Hz, 1H), 3.35-3.43 (m, 3H), 3.17 (qd, $J$ = 17.4, 9.2 Hz, 2H), 2.71 (dt, $J$ = 13.3, 7.1 Hz, 1H), 1.74-1.85 (m, 1H), 1.27 (d, $J$ = 6.5, 3H).

FIGURE 18: Extended Data Figure 9: Chemical structure and spectrometric characterization of evolved compounds.

FIGURE 19: Extended Data Figure 10: Absorbance profile of evolved carbapenems assessed using spectroscopy.

INHIBITORS OF BACTERIAL GROWTH

CROSS-REFERENCE TO RELATED APPLICATIONS

This application is a 35 U.S.C. § 371 U.S. national entry of International Application PCT/US2017/015046, having an international filing date of Jan. 26, 2017, which claims the benefit of U.S. Provisional Application No. 62/288,532, filed Jan. 29, 2016, the content of each of the aforementioned applications is herein incorporated by reference in their entirety.

STATEMENT OF GOVERNMENTAL INTEREST

This invention was made with government support under grant nos. 1DP2OD008459-01 and 1R21AI111739-01 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Nov. 9, 2018, is named P13624-03_SL.txt and is 25,307 bytes in size.

BACKGROUND OF THE INVENTION

Tuberculosis (TB) continues to be a major public health threat around the world. The estimate that more lives were lost in 2009 due to TB than in any year in history and more people died in 2014 from tuberculosis than from HIV/AIDS is alarming. An increasing number of cases reporting infection with multi-(MDR) and extensively drug-resistant (XDR) strains of $M.$ $tuberculosis$ has diminished our capability to respond effectively against this threat. A recent study reporting high mortality rates of patients co-infected with HIV and XDR-TB illustrates the need for new drugs to treat TB. It is speculated that poor patient compliance to treatment regimens, as the current therapy requires a combination of drugs to be taken daily for 6 months or more, is a major reason for emergence of drug resistance in TB. While >99% of $M.$ $tuberculosis$ bacilli are killed within 2 weeks of therapy, it takes the remainder of the therapy to effectively kill the surviving population. These bacilli, broadly termed "persisters", are able to transiently tolerate drugs. The phenomenon of persistence is poorly understood. In vitro models designed to mimic the physiology of persisters are based on exposure to nitric oxide and depletion of oxygen and nutrients as these conditions are thought to prevail in a persisting infection in vivo.

A higher percentage of bacilli are able to survive exposure to drugs at stationary phase compared to exponential phase growth. The bacterial cell wall, as an interface between the pathogen and the host, regulates diffusion, influx and efflux of drugs and metabolites. Integrity and permeability of this interface is highly significant to effective targeting of $M.$ $tuberculosis$ with drugs. Little is known about changes in the cell wall during chronic phase of infection and whether it regulates persistence of $M.$ $tuberculosis$ in the host. Until recently, it was thought that D,D-transpeptidases (commonly known as penicillin binding proteins), which catalyze the synthesis of cross-linked peptide bonds between the $4^{th}$ amino acid of one stem peptide and $3^{rd}$ amino acid of another thereby forming 4→3 linkages, was the only class of enzymes involved in the final step of peptidoglycan (PG) biosynthesis. The mechanism by which $M.$ $tuberculosis$ maintains 3→3 cross-linkages in the peptidoglycan layer has recently been identified by the discovery of an $M.$ $tuberculosis$, $Ldt_{Mt2}$, encoding for an L,D-transpepetidase and identification of its role as a catalyst for the formation of non-classical 3→3 cross-linkages in the peptidoglycan layer. Inactivation of the gene encoding $Ldt_{Mt2}$ protein results in altered colony morphology, attenuation in growth, loss of virulence, and increased susceptibility to β-lactams and β-lactamase inhibitors in vitro and during the chronic phase of tuberculosis infection as demonstrated in the mouse model of the disease. Non-classical 3→3 cross linkages predominate the transpeptide network of the peptidoglycan layer of non-replicating $M.$ $tuberculosis$. The peptidoglycan network is a dynamic structure that is cross-linked by both 4→3 and 3→3 transpeptide linkages. Both L, D and D,D-transpeptidases are involved in the maintenance and remodeling of the peptidoglycan network in $M.$ $tuberculosis$. New inhibitors to the recently identified L,D-transpeptidase must be discovered to develop new antibacterial agents enabling growth inhibition of bacteria strains resistant to conventional drugs. Of broader significance is the emerging fact that 3→3 linkages and l,d-transpeptidases are present in a wide range of bacteria such as $E.$ $coli$, $Pseudomonas$ spp., $K.$ $pneumoniae$, $Streptomyces$ spp., $C.$ $difficile$, $Actinomycetales$ spp., $E.$ $faecium$, $E.$ $faecalis$, $A.$ $baumannii$ and $E.$ $cloacae$.

SUMMARY OF THE INVENTION

This application includes new antimicrobials, and their unique chemical structures, that target the inactivation of L,D-transpeptidases. Carbapenems and penems of the present invention are unique among β-lactams as they acylate and inhibit L,D-transpeptidases, which likely results in their superior antimicrobial potency. These new antimicrobial agents can be used alone, or in combination with other classic antimicrobial agents that target L,D transpeptidases, when treating bacterial infections.

A compound of Formula (I):

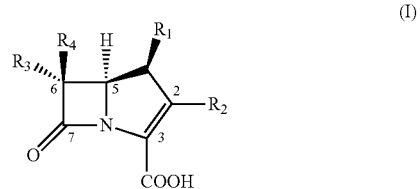

wherein:
R1 is —H or —CH3;
R2 is

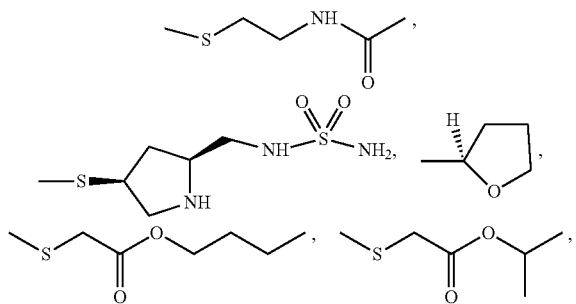

3
-continued
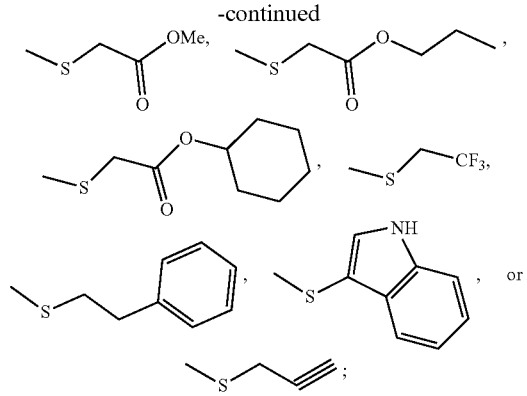
R3 is H or:
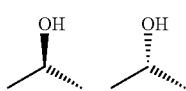
R4 is H or:
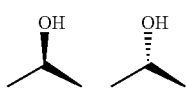
and
R5 is —COOH or a pharmaceutically acceptable salt, solvate, or stereoisomer thereof.
The compound, salt, solvate, or stereoisomer of a compound of Formula (I), wherein the compound is one of the following:
Compound T121
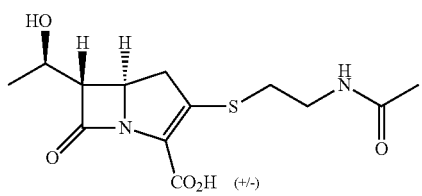
Compound T122
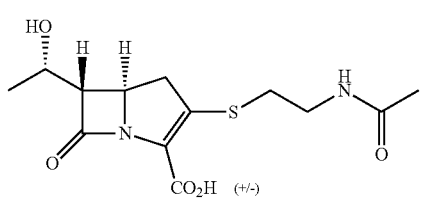
Compound T123
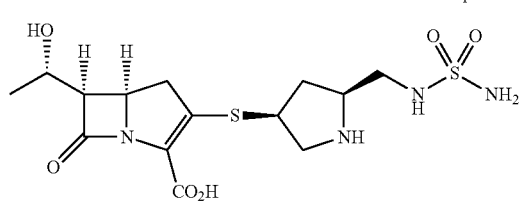
4
-continued
Compound T125
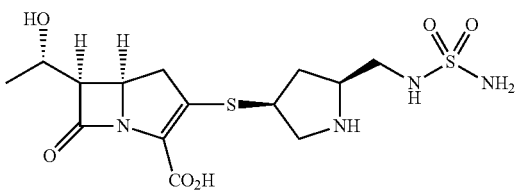
Compound T193
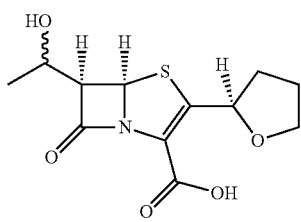
Compound T202
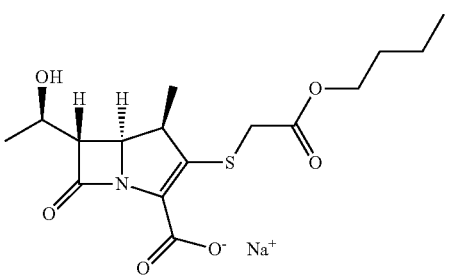
Compound T203
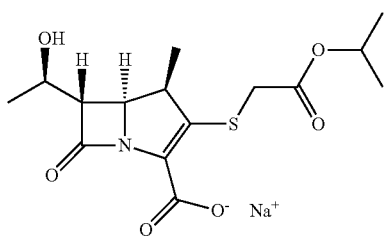
Compound T205
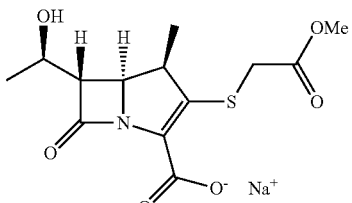
Compound T206
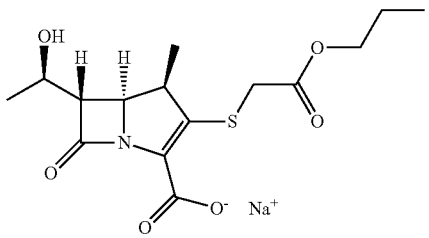

-continued

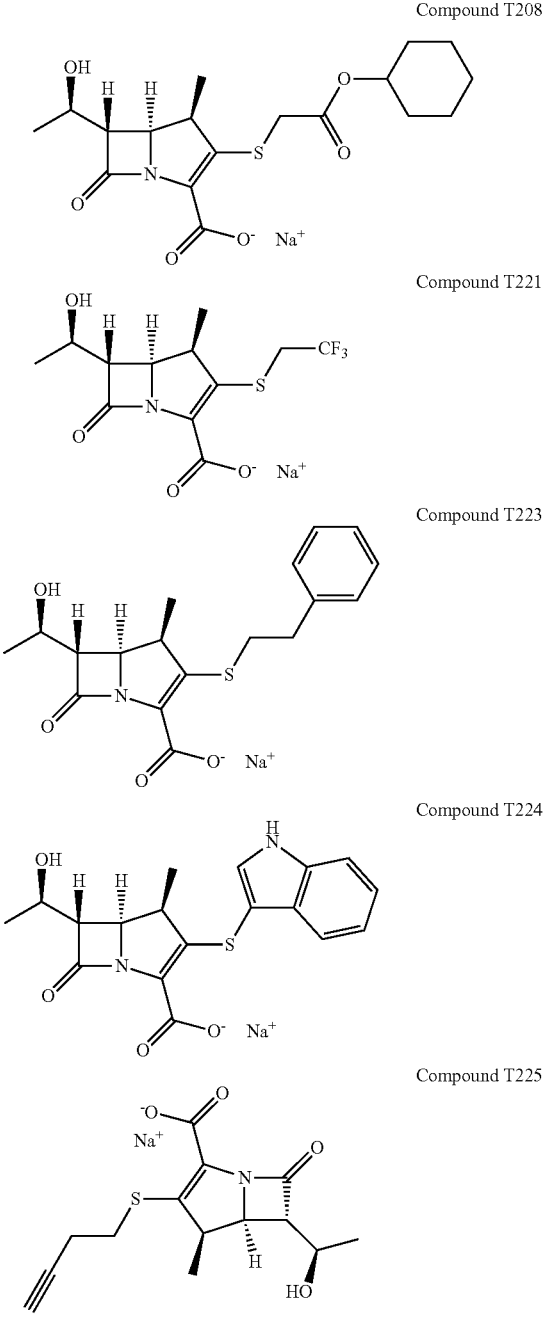

Compound T208

Compound T221

Compound T223

Compound T224

Compound T225

A pharmaceutical composition comprising a compound, salt, solvate, or stereoisomer of any one of the compounds of Formula (I) or the compounds listed above, and a pharmaceutically acceptable carrier.

A pharmaceutical composition comprising a compound, salt, solvate, or stereoisomer of any one of the compounds of Formula (I) or the compounds listed above, and at least one or more other antimicrobial compound(s). The one or more antimicrobial compound maybe selected from the group consisting of penicillin, rifampicin, amoxicillin, cephalothin, aztreonam, doripenem, faropenem, biapenem or a combination thereof.

A method of treating, or preventing, a bacterial infection in a subject comprising administering to the subject an effective amount of a compound, salt, solvate, or stereoisomer of any one of the compounds of Formula (I) or the compounds listed above. This method may treat any bacterial infection (s) including *M. tuberculosis, M. abscessus, A. baumannii, S. aureus, K. pneumoniae, E. cloacae, P. aeruginosa* infections or a combination thereof, for example.

The method wherein the bacterial infection is an infection with any bacteria that results in disease and suffering.

The method wherein the bacterial infection is one or more strains of bacteria that is resistant to antimicrobial agents directed to inactive D,D-transpeptidase.

A method of inhibiting the growth of a bacteria in vitro comprising contacting the bacteria with an effective amount of a compound, salt, solvate, or steroisomer of any one of the compounds of Formula (I) or the compounds listed above wherein the bacteria stops growing.

A method of inhibiting L,D-transpeptidase activity in a subject with a bacterial infection, comprising administering to the subject an effective amount of a compound, salt, solvate, or stereoisomer of any one of the compounds of Formula (I) or the-compounds listed above wherein the L,D-transpeptidase activity is less than when the subject is not administered an effective amount of the compound.

A method of inhibiting L,D-transpeptidase activity in a subject with a bacterial infection, comprising administering to the subject an effective amount of a compound, salt, solvate, or stereoisomer of any one of the compounds selected from the group comprising:

Compound T201

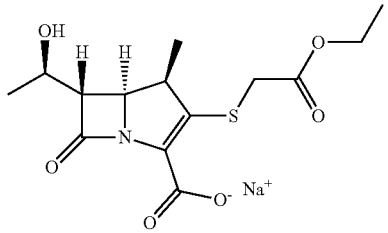

Compound T210

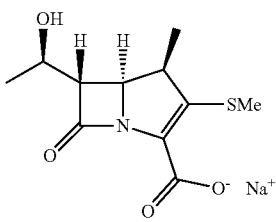

Compound T222

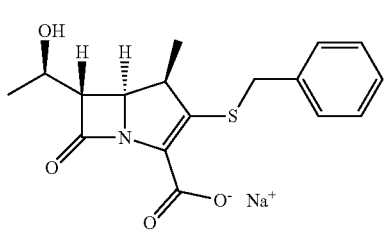

wherein the L,D-transpeptidase activity in the subject with the bacterial infection is less than when the subject is not administered an effective amount of any one of the compounds.

In accordance with an embodiment, the present invention provides pharmaceutical composition comprising a compound, salt, solvate, or stereoisomer of any one of the compounds of Formula I, as set forth above, and at least one or more other antimicrobial compounds, and a pharmaceutically acceptable carrier.

In another embodiment, the present invention provides a method of inhibiting L,D-transpeptidase activity in a subject with a bacterial infection, comprising administering to the subject an effective amount of a compound, salt, solvate, or stereoisomer of any one of the compounds of Formula I, as set forth above.

In accordance with an embodiment, the present invention provides a method of treatment of one or more bacterial infection(s) in a subject comprising administering an effective amount of a compound of Formula I, as set forth above.

BRIEF DESCRIPTION OF THE DRAWINGS

FIG. 1 illustrate Tables 1 & Table 2. Table 1 illustrates the mass-spectrometric analysis of adducts formed between $Ldt_{Mt1}$, $Ldt_{Mt2}$, $Ldt_{Mt}2$, $Ldt_{Mab1}$, $Ldt_{Mab2}$, $Ldt_{Kp}$, $Ldt_{Cl}$, and $Ldt_{Pa}$ and a range of compounds. Molecular weights (MW) of detected adducts are shown (in daltons). A (Amoxicillin), C (Cephalothin), Z (Aztreonam, MW=435.4), D (Doripenem), F (Faropenem), B (Biapenem, MW=350.4) and T (Tebipenem, MW=383.5). Not determined (n.d.). Table 2 illustrates the minimum inhibitory concentrations (MIC) of experimental carbapenems in μg/ml. The data shown in this table was verified with two repeats of MIC determination. MSSA and MRSA refer to Methicillin sensitive and resistant *Staphylococcus aureus*, respectively. Meropenem was used as a control.

FIGS. 3 (*a* and *b*) illustrates gross pathology of lungs of mice infected with *M. tuberculosis*. Mice received the following treatments: (a) no treatment, (b) isoniazid, (c) rifampicin, (d) isoniazid+rifampicin, (e) biapenem, (f) biapenem+ rifampicin, (g) faropenem, (h) faropenem+rifampicin. Each lung shown here is representative of lungs of mice in the corresponding treatment group. FIG. 3 *b*. illustrates *M. tuberculosis* burden in the lungs of mice. Total number of *M. tuberculosis* bacilli that could be recovered from lungs of mice at various stages of infection and treatment. Isoniazid (INH) and rifampicin (RIF).

FIGS. 4 (*a-f*) illustrates the chemical structures of some of the evolved carbapenems. From top to bottom, T123, T206, T208 and T210. FIG. 4*b* illustrates the kinetics of acylation of $Ldt_{Mt2}$ by evolved carbapenems T208 and T210. Kinetic constants $k_{inact}$ and $K_{app}$ were determined spectrophotometrically. FIG. 4*c* illustrates the crystal structure of T206 at the catalytic site of $Ldt_{Mt2}$. Conformation A (top panel) and conformation B (bottom panel) showing interaction of T206 adduct (cyan) with residues at the catalytic site of $Ldt_{Mt2}$ (green) and water (w). The 2Fo-Fc difference fourier map (gray) is contoured at 1.0σ. Distances are in Å. FIG. 4*d* illustrates the Crystal structure of T208 at the catalytic site of $Ldt_{Mt2}$. Interaction of T206 adduct (cyan) with residues at the catalytic site of $Ldt_{Mt2}$ (green) and water (w). The 2Fo-Fc difference fourier map (gray) is contoured at 1.0σ. Distances are in Å. FIG. 4*e* illustrates Crystal structure of T210 at the catalytic site of $Ldt_{Mt2}$. Interaction of T210 adduct (cyan) with resides at the catalytic site of $Ldt_{Mt2}$ (green). The 2Fo-Fc difference fourier map (gray) is contoured at 1.0σ. Distances are in Å. FIG. 4*f* illustrates the proposed mechanism of acylation of $Ldt_{Mt2}$ by T208. This mechanism is based on data on adduct from x-ray crystallography and mass-spectrometry. Carbapenems T206 and T210 react with a similar mechanism.

FIG. 5 illustrates Extended Data Table 1. Extended Data Table I illustrates the summary of materials associated with proteins described in this study. Primers are DNA oligos used for PCR amplification of fragments from genomic DNA of *M. tuberculosis, M. abscessus, K. pneumoniae, E. cloacae* and *P. aeruginosa*. Plasmid refers to the pET28a+ TEV derived vector carrying desired gene. Expression strains are *E. coli* BL21DE3 clones harboring corresponding plasmid used for overexpression of proteins. FIG. 5 discloses SEQ ID NOS 2-35, respectively, in order of appearance.

FIG. 6 illustrates Extended Data Table 2. Extended Data Table 2 illustrates the binding characterization using Isothermal Titration calorimetry. In all assessments the protein and ligand concentrations were 150 μM and 2 mM, respectively.

FIG. 7 illustrated Extended Data Table 3. Extended Data Table 3 illustrates the mass-spectrometric analysis of adducts formed from reaction between L,D-transpeptidase $Ldt_{Mt2}$ (wild-type), mutant $Ldt_{Mt2}$ with single amino acid substitutions and Biapenem, Faropenem and Tebipenem. Molecular weights (MW) of detected adducts are shown (in daltons). Not determined (n.d.).

FIG. 8 illustrates Extended Data Table 4. Extended Data Table 4 illustrates data collection and refinement statistics.

FIG. 9 illustrates Extended Data Table 5. Extended data table 5 illustrates data collection and refinement statistics.

FIG. 10 illustrates Extended Data FIG. 1. Extended Data FIG. 1 illustrates the sequence alignment of putative L,D-transpeptidases of *M. abscessus* $Ldt_{Mab1}$ (Locus tag, MAB_3165c) and $Ldt_{Mab2}$ (Locus tag, MAB_1530), *K. pneumoniae* $Ldt_{Kp}$ (Locus tag, LQ47_09165), *E. cloacae* LdtC1 (Locus tag, ECL_02364) and *P. aeruginosa* $Ldt_{Pa}$ (Locus tag, PA1S_11140) with $Ldt_{Mt2}$ of *Mycobacterium tuberculosis*. Amino acids in red bar represent identical residues and in blue bar represent similar residues. FIG. 10 discloses SEQ ID NOS 36-41, respectively, in order of appearance.

FIG. 2 illustrates the determination of binding affinities of $Ldt_{Mt1}$, $Ldt_{Mt2}$, $Ldt_{Mab1}$ and $Ldt_{Mab2}$ for Amoxicillin, Cephalothin and Aztreonam using isothermal titration calorimetry.

FIG. 2 illustrates the determination of binding affinities of Ldt$_{Mt1}$, Ldt$_{Mt2}$, Ldt$_{Mab1}$ and Ldt$_{Mab2}$ for Amoxicillin, Cephalothin and Aztreonam using isothermal titration calorimetry.

FIG. 4 illustrates the core structure common to carbapenems.

FIG. 4 illustrates the X-ray crystal structures of Apo Ldt$_{Mt2}$ (5a) and Ldt$_{Mt1}$ (5b).

FIG. 6 illustrates the gross pathology of lungs of all mice infected with *M. tuberculosis* that received various treatments: (a) no treatment, (b) isoniazid, (c) rifampicin, (d) isoniazid+rifampicin, (e) biapenem, (f) biapenem+rifampicin, (g) faropenem, (h) faropenem+rifampicin.

FIG. 7 illustrates the structures of evolved carbapenems with significant antibacterial activity T202, T203, T205, T207, T209, T221, T222, T223 and T224.

FIG. 8 illustrates the scheme for synthesis of evolved carbapenems.

FIG. 18 illustrates Extended Data FIG. 9. Extended Data FIG. 9 illustrates the chemical structure and spectrometric characterization of evolved compounds of: a. T201; b. T202; c. T203; d. T204; e. T205; f T206; g. T207; h. T208; i. T209; j. T210; l. T211; m. T212; n. T213; o. T214; p. T215; q. T216; r. T217; s. T218; t. T219; u. T220; v. TT221; x. T222; y T223; z. TT224; and aa. (5R,6S,8R)-Des-1β-methyl-doripenem p-nitrobenzyl ester and (5S,6R,8S)-Des-1β-methyl-doripenem p-nitrobenzyl ester; bb. T123.

FIG. 10 illustrates the Chemical structure and spectrometric characterization of evolved compounds.

DETAILED DESCRIPTION OF THE INVENTION

In accordance with the present invention, the inventors have determined that the compounds of Formula I, may be clinically useful for treating, or preventing, bacterial infections, such as *M. tuberculosis*, *M. abscessus*, *E. cloacae*, *S. aureus*, *A. baumannii*, *K. pneumoniae*, *E. cloacae* and *P. aeruginosa*.

In an embodiment, the present invention provides a compound of Formula I:

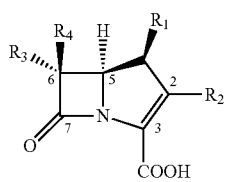

(I)

wherein
R1 is —H or —CH3;
R2 is

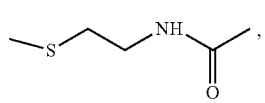

-continued

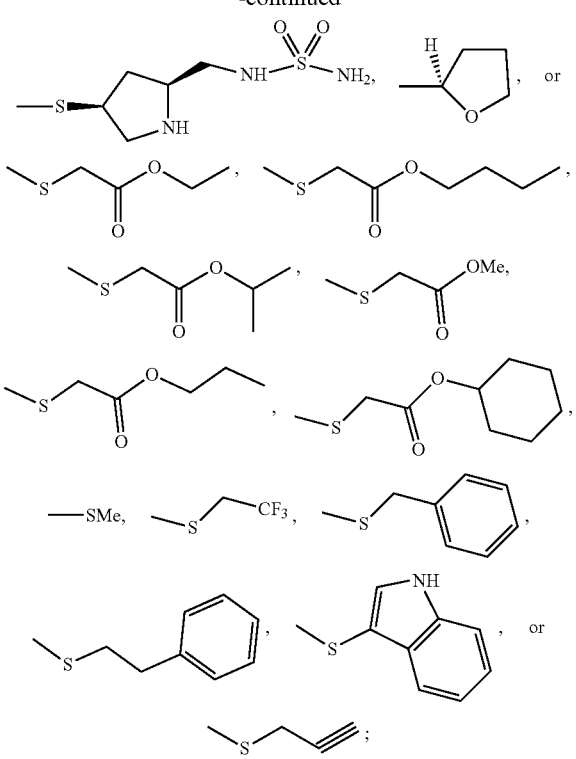

R3 is

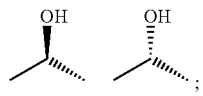

R4 is

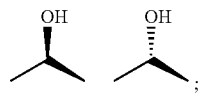

and;

R5 is —COOH or a pharmaceutically acceptable salt, solvate, or stereoisomer thereof.

In another embodiment, the present invention provides the compound, salt, solvate, or stereoisomer of one or more compounds of Formula I, as set forth above, wherein the compound is one of the following:

Compound T121

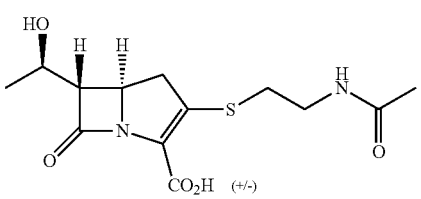

Compound T122
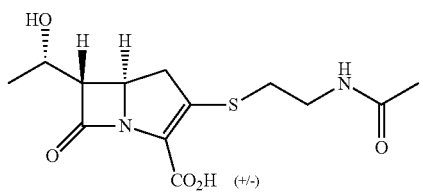
Compound T123
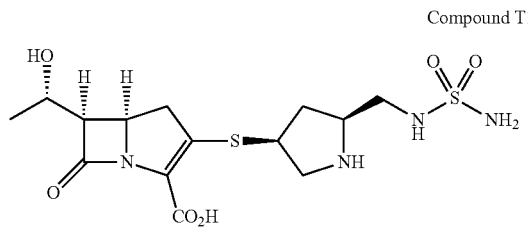
Compound T125
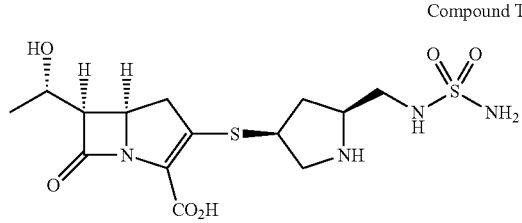
Compound T193
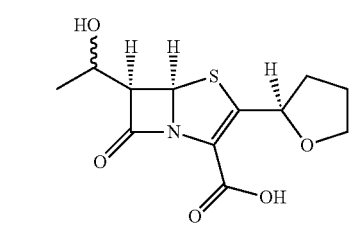
Compound T201
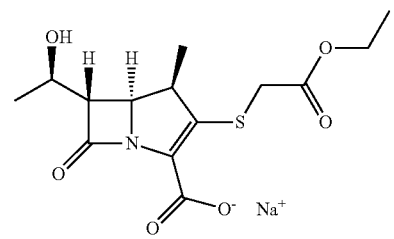
Compound T202
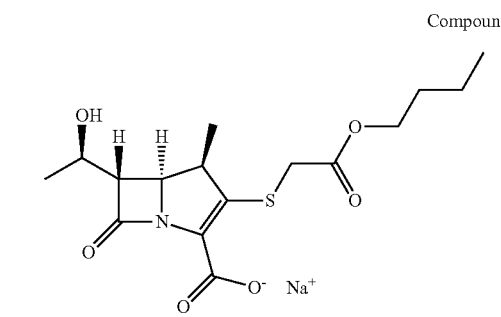
Compound T203
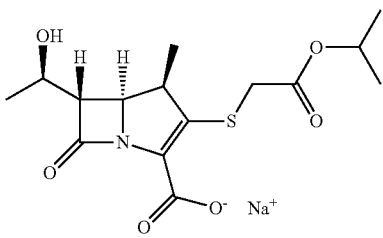
Compound T205
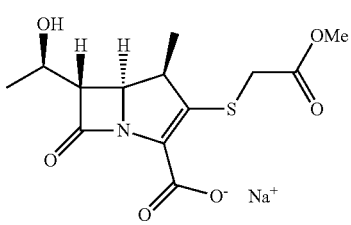
Compound T206
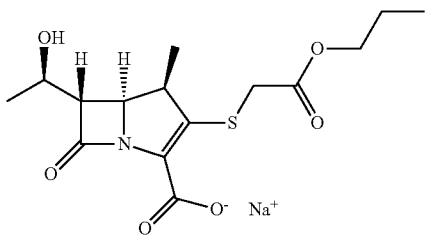
Compound T208
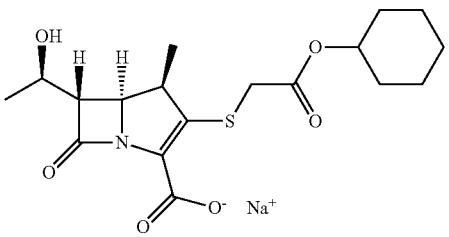
Compound T210
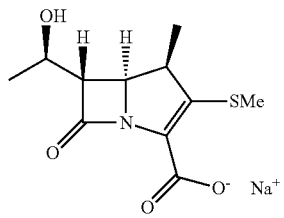
Compound T221
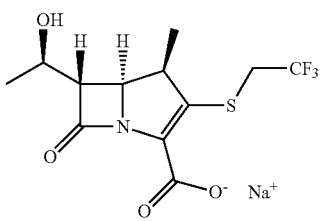

-continued

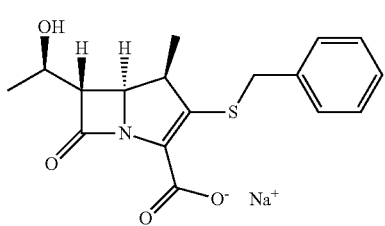

Compound T222

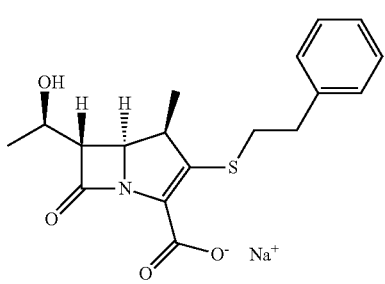

Compound T223

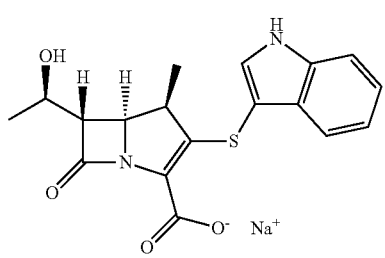

Compound T224

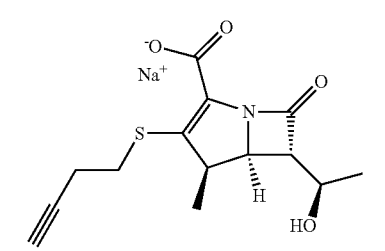

Compound T225

These novel inhibitors of L,D-transpeptidases, the compound of Formula I, were discovered by studying binding affinities of L,D-transpeptidases to all classes of β-lactams, namely penicillins, cephalosporins, monobactams, carbapenems and penems represented by amoxicillin, cephalothin, aztreonam, doripenem and faropenem, respectively. $Ldt_{Mt2}$, the dominant L,D-transpeptidase of *M. tuberculosis*, was used and its paralog $Ldt_{Mt1}$ as representative L,D-transpeptidases of this pathogen as deficiency of these two enzymes results in major cellular aberrations. The existence of or identities of L,D-transpeptidases in *M. abscessus, K. pneumoniae, E. cloacae* and *P. aeruginosa* was determined. Using a basic alignment search with $Ldt_{Mt2}$, $Ldt_{Mt1}$ and *E. coli* L,D-transpeptidase sequences, we identified orthologues in *M. abscessus, K. pneumoniae, E. cloacae* and *P. aeruginosa* (FIG. 10). Orthologues of $Ldt_{Mt2}$ and $Ldt_{Mt1}$ in *M. abscessus* are referred to hereafter as $Ldt_{Mab2}$ and $Ldt_{Mab1}$, respectively. Similarly, putative L,D-transpeptidases in *K. pneumoniae, E. cloacae* and *P. aeruginosa* are referred to hereafter as $Ldt_{Kp}$, $Ldt_{Cl}$ and $Ldt_{Pa}$, respectively. All of these proteins, except $Ldt_{Mab1}$, possess a single putative transmembrane domain at the N-terminus and a C-terminal L,D-transpeptidase domain. Fragments excluding the putative transmembrane domain were cloned, expressed and purified in *E. coli* BL21δε3 strain (FIG. 5).

Figure 2A:
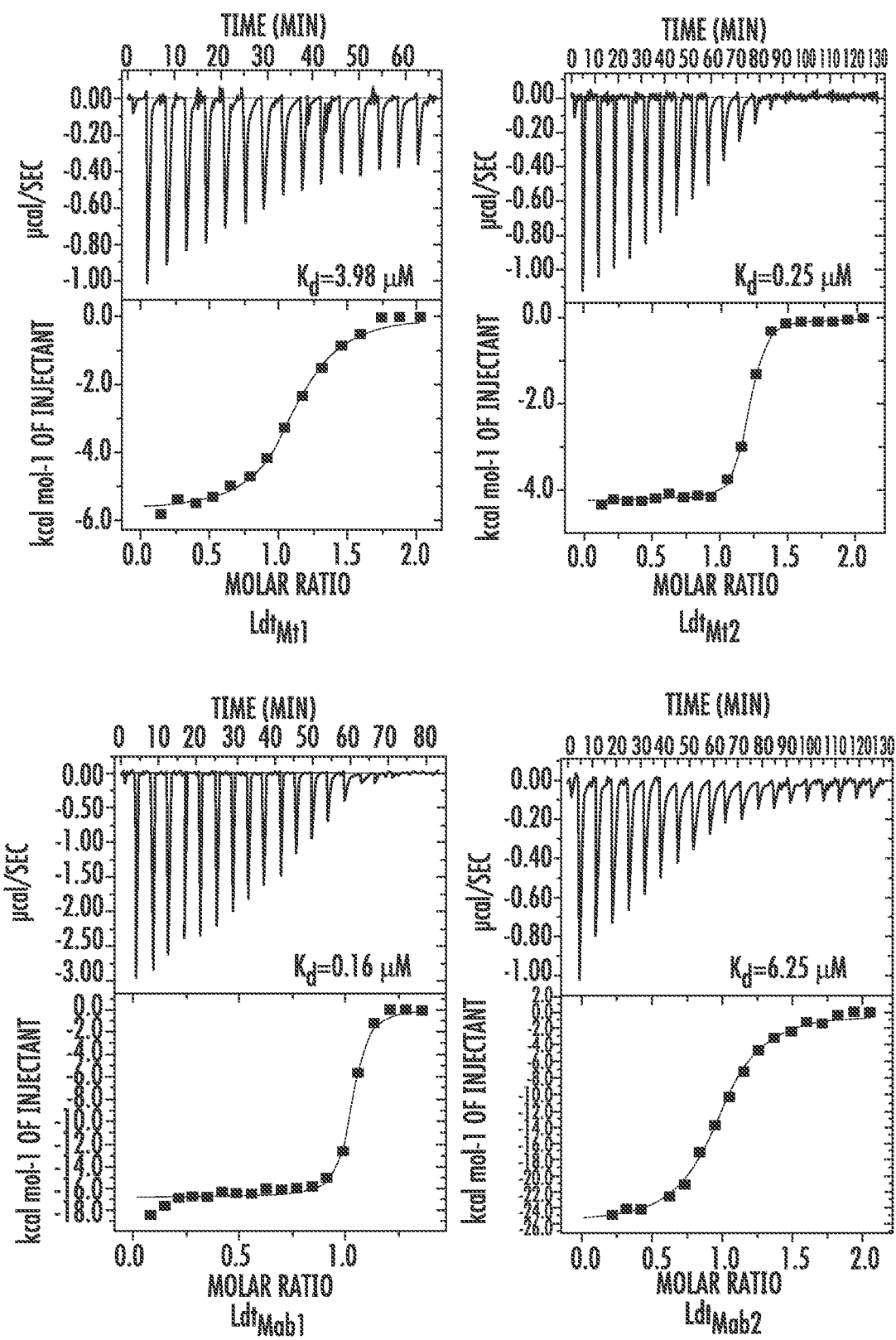
FIGS. 2 (*a-g*) illustrates: a. Assessment of binding affinity of faropenem to $Ldt_{Mt1}$, $Ldt_{Mt2}$, $Ldt_{Mab1}$ and $Ldt_{Mab2}$ using isothermal titration calorimetry. Top plot of each panel displays titration of faropenem to enzyme. The bottom plots display non-linear fit of heat exchange at various molar ratios of ligand: enzyme; b. Kinetics of inhibition of $Ldt_{Mt2}$ by carbapenems and a penem; c. Crystal structure of $Ldt_{Mt2}$ bound by faropenem showing the five residues in the catalytic site of $Ldt_{Mt2}$ (green) with which 86 Da faropenem adduct (cyan) makes significant interactions and the 2Fo-Fc difference fourier map (gray) is contoured at 1.0σ. Distances are in Å; d. Crystal structure of $Ldt_{Mt1}$ bound by faropenem where this structure shows the residues in the catalytic site of $Ldt_{Mt1}$ (green) with which 86 Da faropenem adduct (cyan) and he 2Fo-Fc difference fourier map (gray) is contoured at 1.0σ nd the distances are in Å; e, Crystal structure of $Ldt_{Mt2}$ bound by doripenem where this structure shows a 123 Da doripenem adduct (cyan) covalently bound to C354 in the catalytic site of $Ldt_{Mt2}$ (green) and the 2Fo-Fc difference fourier map (gray) is contoured at 1.0σ and the instances are in Å; f Proposed mechanism of acylation of $Ldt_{Mt2}$ by faropenem; g. Proposed mechanism of acylation of $Ldt_{Mt2}$ by doripenem.
Figure 11A:
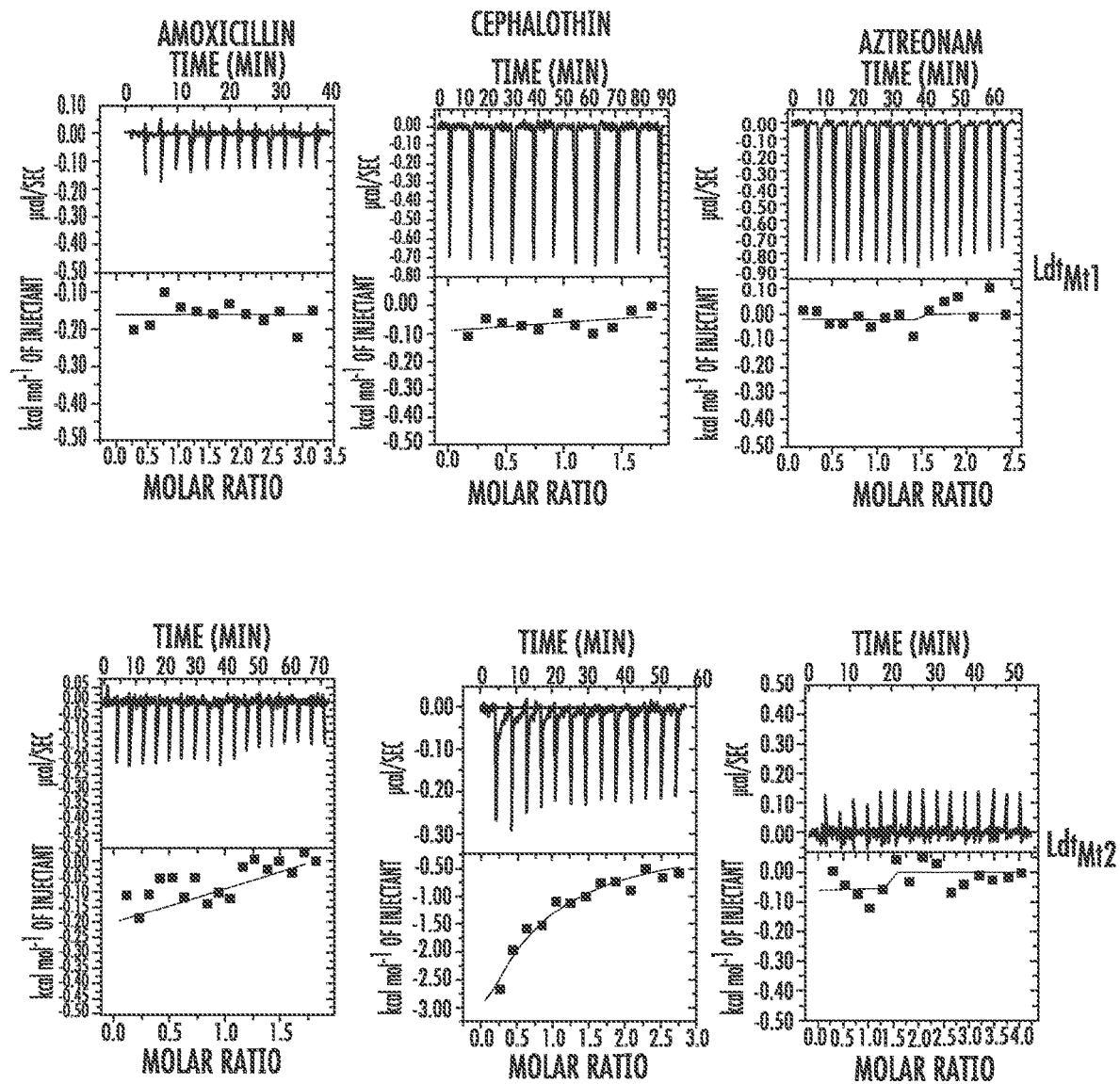
FIG. 11 illustrates Extended Data FIG. 2. Extended Data
Figure 11B:
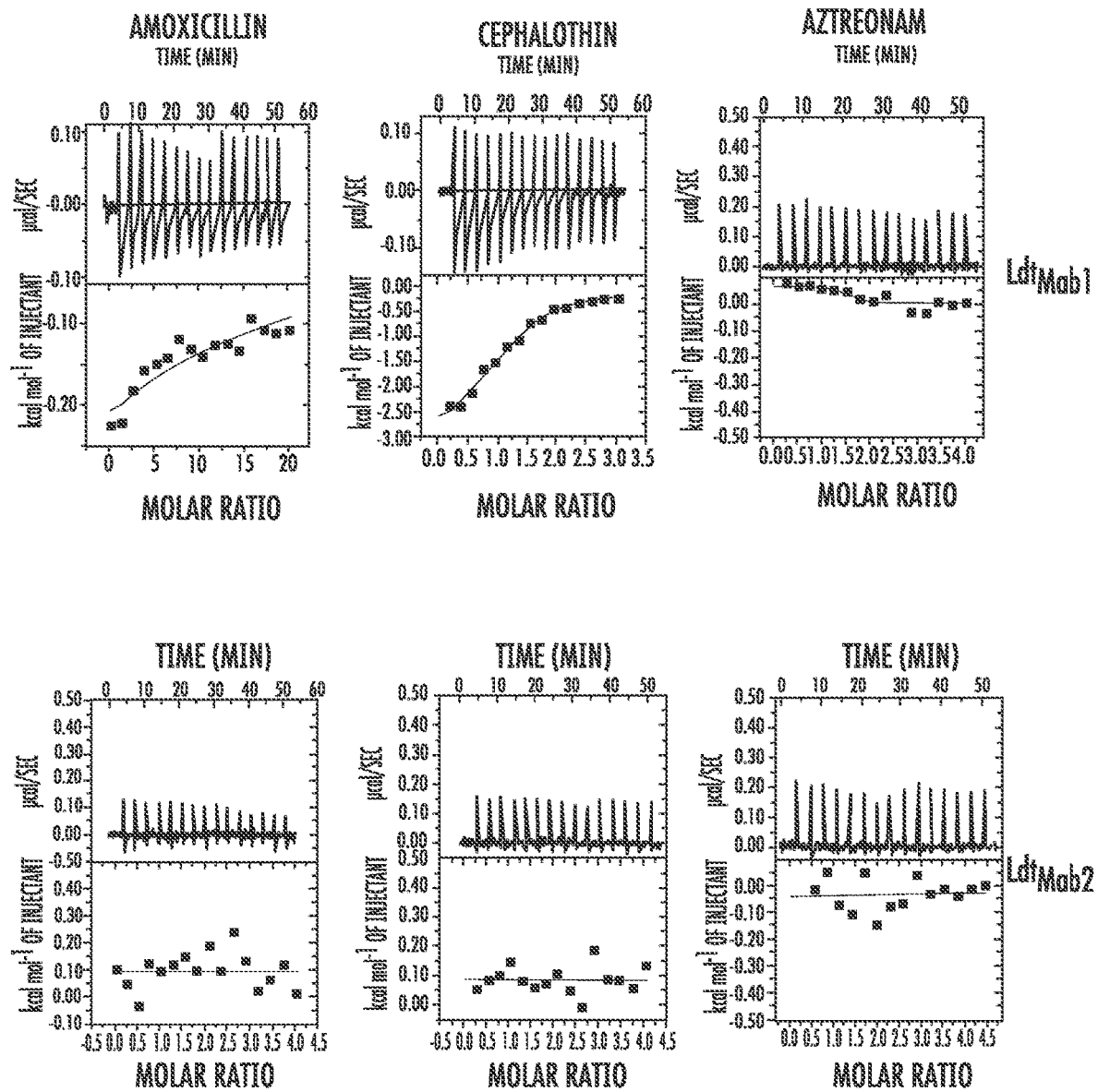
Figure 12A:
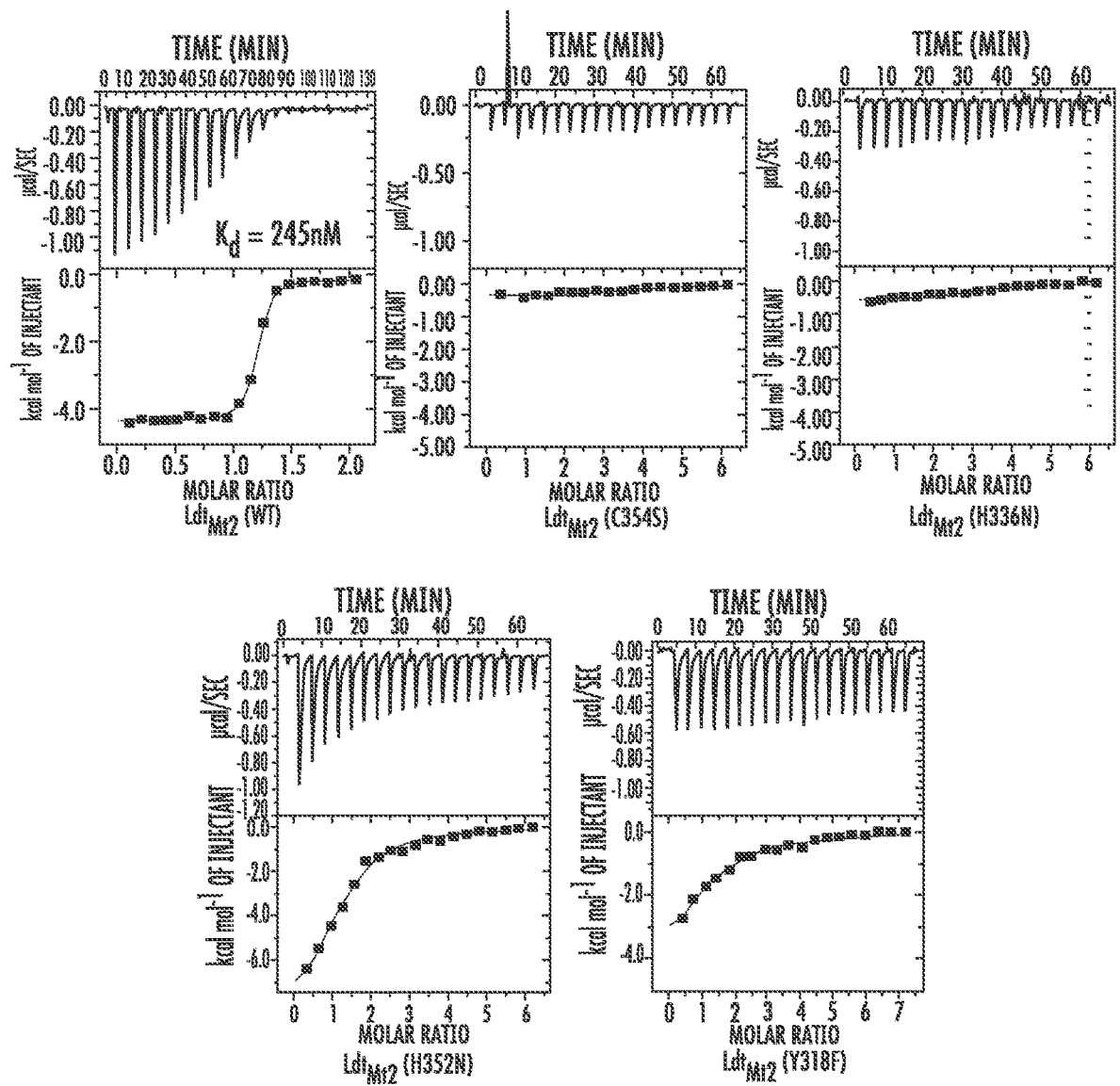
FIG. 12 illustrates Extended Data FIG. 2. Extended Data
Figure 12B:
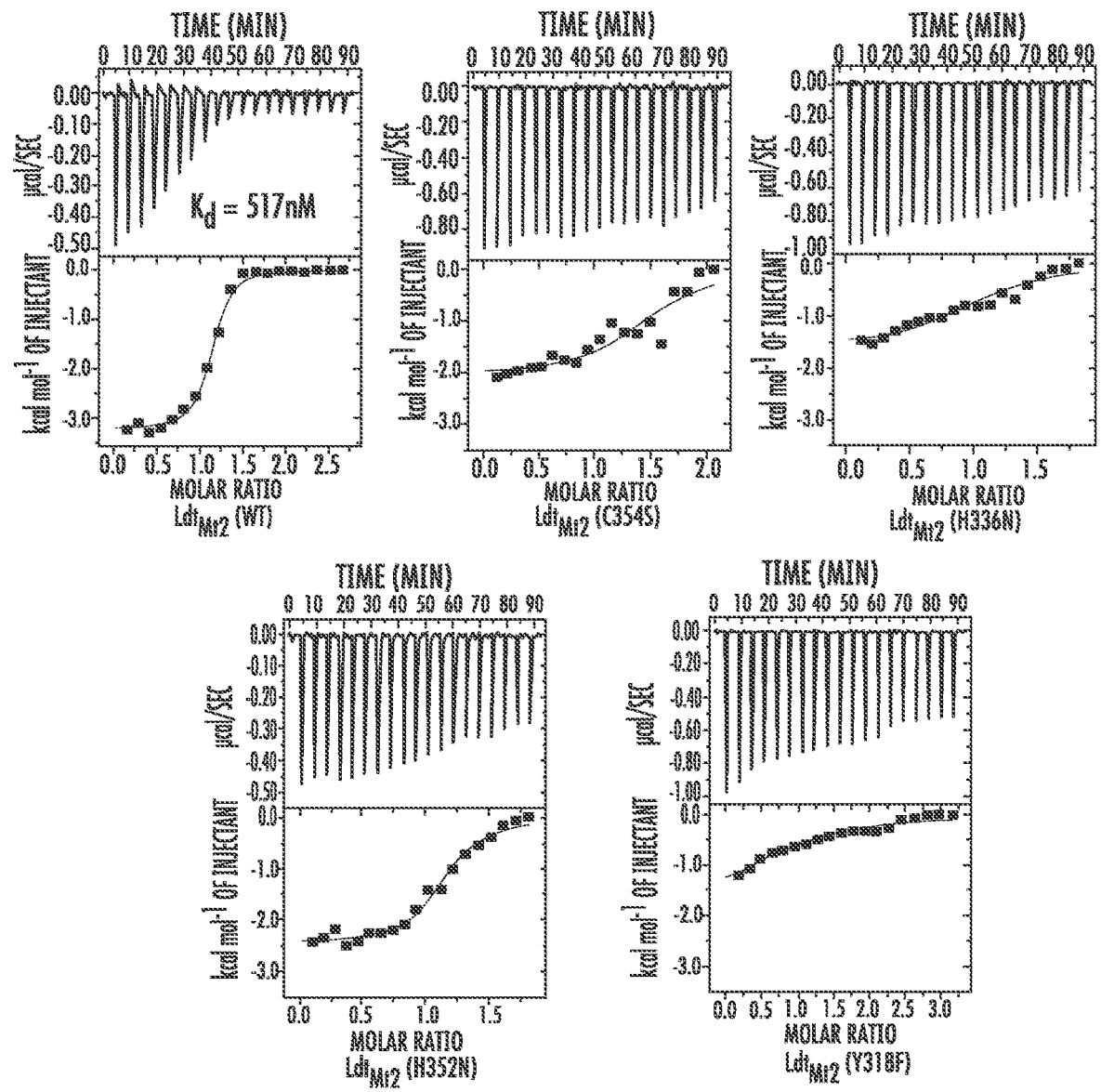

Isothermal titration calorimetry (ITC) was used to measure heat associated with β-lactam-protein complex formation and subsequently to determine corresponding binding affinities. While a heat of association could not be detected for amoxicillin, cephalothin or aztreonam with $Ldt_{Mt1}$ or $Ldt_{Mt2}$ (FIG. 11), the two enzymes exhibited strong affinity for faropenem with a single binding modality and $K_d$ of 3.98 and 0.24 µM, respectively (FIG. 2a). Likewise, L,D-transpeptidases of *M. abscessus*, $Ldt_{Mab1}$ and $Ldt_{Mab2}$, also displayed affinity only for faropenem with a $K_d$ of 0.16 and 6.25 µM, respectively (FIG. 11, FIG. 6).

A hypothesis was tested to determine if a L,D-transpeptidase would be preferentially acylated by the most reactive carbapenem or penem. For this competition assay, $Ldt_{Mt1}$, $Ldt_{Mt2}$, $Ldt_{Mt1}$, $Ldt_{Mab1}$, $Ldt_{Mab2}$, $Ldt_{Cl}$, and $Ldt_{Kp}$ were separately incubated with an equimolar mixture of doripenem, biapenem, faropenem and tebipenem and the identities and abundance of acylated adducts were determined using UPLC-MS. Within one minute of incubation, 100% of proteins reacted exclusively with faropenem although each of the four acylated the protein when used alone (FIG. 1a). Next, we reacted $Ldt_{Mt1}$, $Ldt_{Mt2}$, $Ldt_{Mab1}$, $Ldt_{Mab2}$, $Ldt_{Cl}$ and $Ldt_{Kp}$ separately with an equimolar mixture of amoxicillin, cephalothin, aztreonam and faropenem. Invariably, faropenem adducts gave the only masses we could detect. A 458 Da adduct of unknown structure was detected for $Ldt_{Pa}$. These results suggest that among the β-lactams, penems are most reactive against L,D-transpeptidases, while faropenem is the most reactive among the tested β-lactams.

Next, we determined amino acids in the catalytic core of L,D-transpeptidases were critical for activity. We chose $Ldt_{Mt2}$ to undertake this assessment based on its demonstrated significance to peptidoglycan metabolism in *M. tuberculosis*. Based on sequence conservation among known L,D-transpeptidases, orientation and interaction with peptide substrate within the catalytic site, and the placement of meropenem as observed in co-crystals with $Ldt_{Mt2}$, Y308, Y318, H336 and C354 appear to play direct roles in the activity of this enzyme. Other conserved residues in the catalytic site, and therefore potentially critical to catalysis, include G332 and H352. We generated the following single amino acid mutations in $Ldt_{Mt2}$ and studied the role of each residue in interactions with the carbapenems biapenem and tebipenem and the penem faropenem: Y318A, Y318F, H336N, H352A, H352N, C354A and C354S. While, a stable adduct of +138 Da was detected for biapenem with wild-type $Ldt_{Mt2}$, no adducts could be detected for all mutants of $Ldt_{Mt2}$ (FIG. 7). Faropenem and tebipenem produced stable adducts of +86, and +339, +383 Da, respectively, with $Ldt_{Mt2}$. The same adducts were detected in Y318 and H352 mutants but H336 and C354 mutants failed to produce any covalent adduct with these drugs indicating that while biapenem interacts with all four residues, faropenem and tebipenem do not require Y318 and H352 for a productive covalent binding interaction. In all reactions that formed adducts, 100% of proteins were covalently acylated confirming that inhibition of $Ldt_{Mt2}$ by carbapenems or penems is irreversible. Simultaneously, we used ITC to assess the contributions of Y318, H336, H352 and C354 in binding affinity of $Ldt_{Mt2}$ to carbapenems. Variants Y318F, H336N, H352N and C354S exhibited either a complete loss of or no appreciable binding affinities for faropenem and tebipenem (FIG. 7) supporting the assessment that these four residues are critical for binding and, therefore, efforts to design and develop new carbapenems should incorporate substituents to effectively engage these residues.

Acylation kinetic studies of Ldt$_{Mt2}$ with different carbapenems and penems were carried out in the presence of increasing concentrations of drug and at a fixed enzyme concentration. The k$_{inact}$ (maximum rate at which an irreversible transformation to enzyme-inhibitor complex occurs), and K$_{app}$ (inhibitor concentration required to achieve half maximum velocity) were determined by non-linear regression to be: doripenem (7.3±0.9 min$^{-1}$ and 32.6±11.3 µM with r$^2$=0.92), biapenem (3.6 min$^{-1}$±0.2 and 15.3±2.5 µM with r$^2$=0.98), faropenem (5.0±0.5 min$^{-1}$ and 49.2±11.9 µM with r$^2$=0.94) and tebipenem (4.7±0.4 min$^{-1}$ and 38.4±9.7 µM with r$^2$=0.95) (FIG. 1b). These parameters demonstrate variations in the acylation kinetics among the carbapenems/penem. The efficiency of these reactions was determined by the k$_{inact}$/K$_{app}$ ratios of doripenem (0.22 µM$^{-1}$ min$^{-1}$), biapenem (0.23 µM$^{-1}$ min$^{-1}$), faropenem (0.10 µM$^{-1}$ min$^{-1}$) and tebipenem (0.12 µM$^{-1}$ min$^{-1}$). Interestingly, although all of these β-lactams inactivated Ldt$_{Mt2}$ by acylation, there are differences in k$_{inact}$ and K$_{app}$ values, which may be attributable to variations in the sulfide side chain of these carbapenems. The variations may cause changes in the rates of both drug binding and subsequent acylation.

Structures with Doripenem and Faropenem

Figure 13:
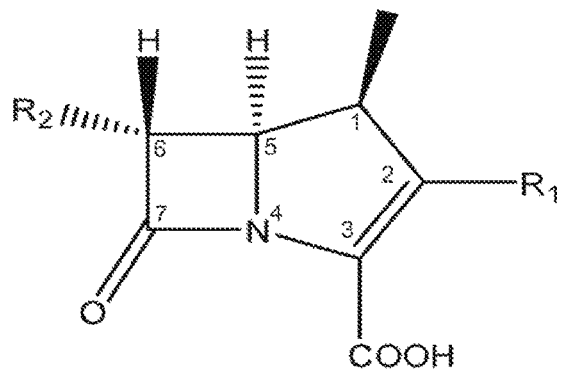
FIG. 13 illustrates Extended Data FIG. 4. Extended Data
Figure 14:
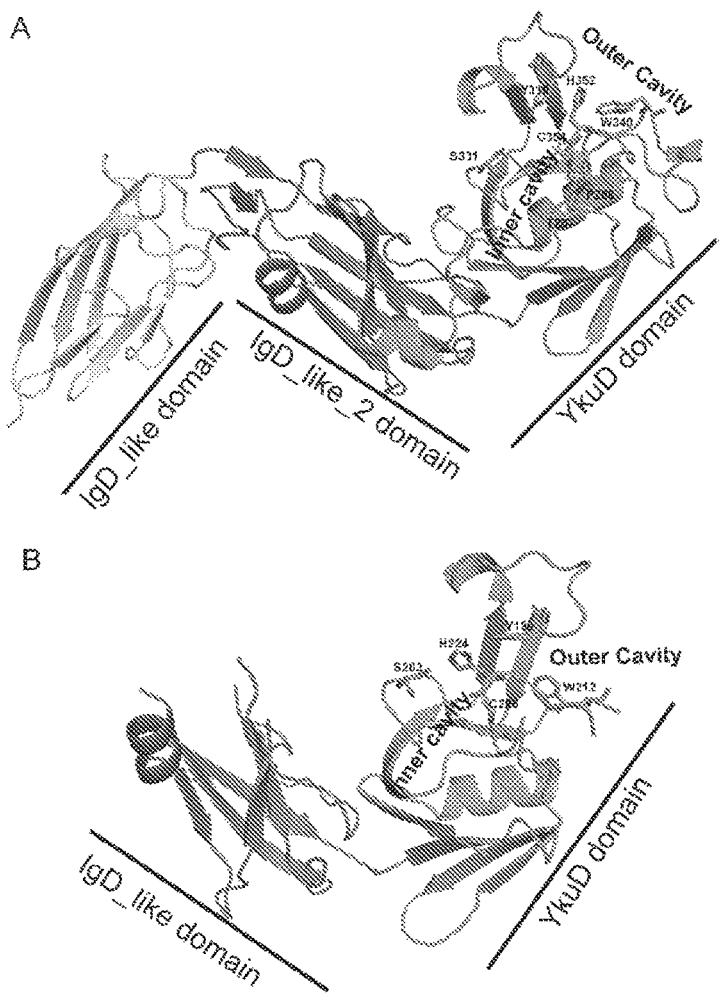
FIG. 14 illustrates Extended Data FIG. 5. Extended Data
Figure 15:
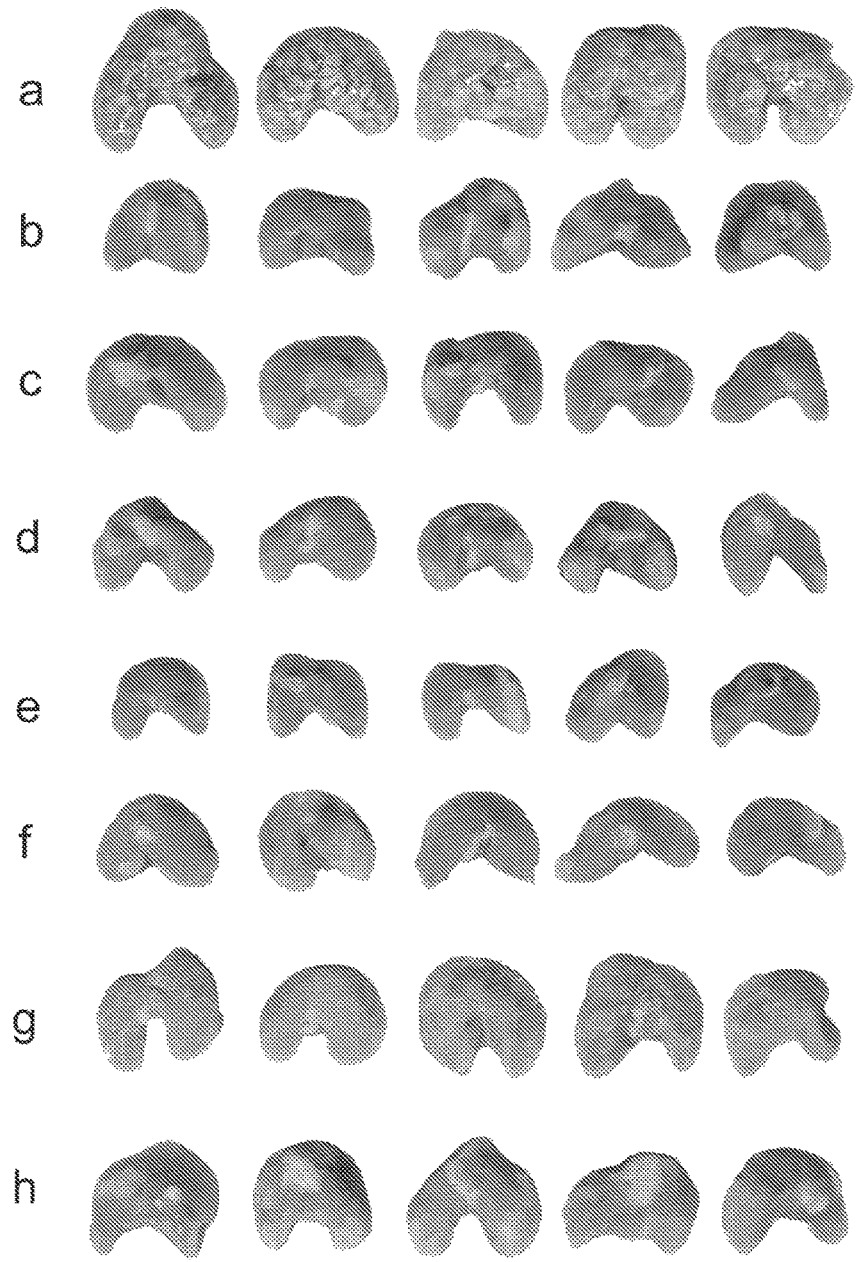
FIG. 15 illustrates Extended Data FIG. 6. Extended Data

Unlike other classes of β-lactams, carbapenems possess a 5 membered unsaturated ring with a carbon at position 1 with penem faropenem bearing a sulfur at this position (FIG. 13). An invariable hydroxyethyl group (R3/4) is attached to C6 and a variable group (R1), which distinguishes each carbapenem, is attached to C2. We generated apo and co-crystals of Ldt$_{Mt2}$ (fragment ΔN55) with doripenem and faropenem and that of Ldt$_{Mt1}$ (fragment ΔN31) with faropenem and solved their molecular structures, which have previously not been described. The apo Ldt$_{Mt2}$ and co-crystallized with faropenem and doripenem, and apo Ldt$_{Mt1}$ and with faropenem were solved at 1.79, 2.17, 2.18, 1.89 and 2.25 Å, respectively (FIG. 8, FIG. 9).

Figure 2C:
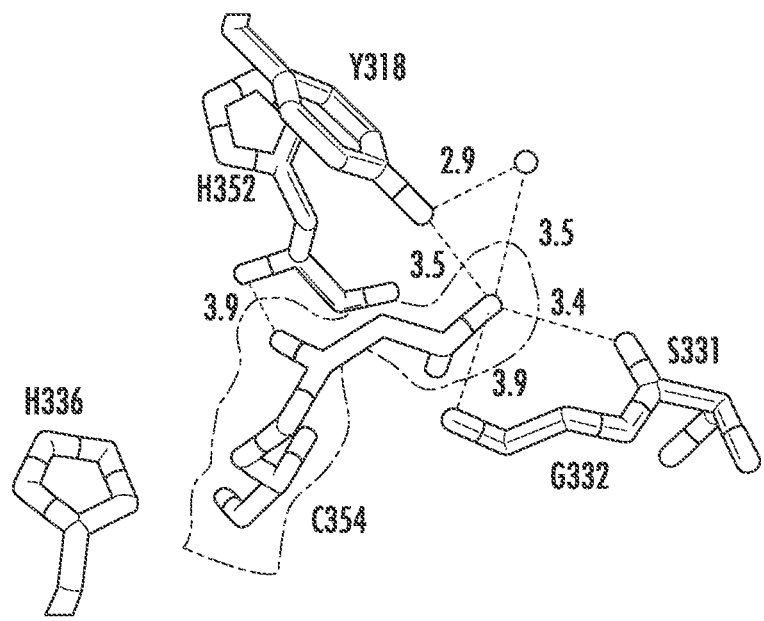
Figure 2D:
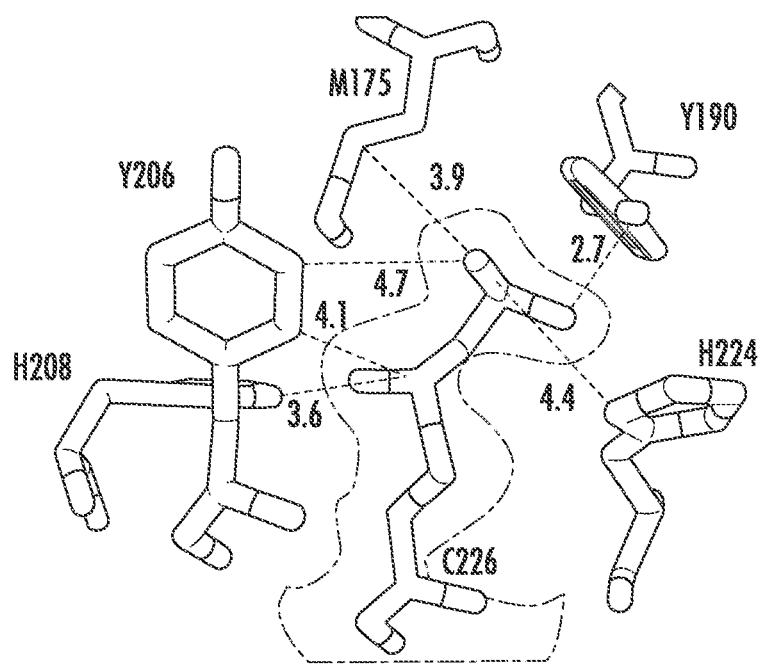

The 2Fo-Fc omit map (contoured at 1.0σ) shows the faropenem adduct bound in the inner cavity of active site of Ldt$_{Mt2}$ (FIG. 2c). The adduct lacks the β-lactam ring, the adjoining 5 membered ring and the R1 group present in the drug initially. Based on these data and the 86 Da adduct detected in ultra-performance liquid chromatography-high resolution mass spectrometry (UPLC-MS), we built a 4-carbon derivative fragment of faropenem into the electron density. The carbonyl carbon C7 is covalently bound to the sulfur of C354, and the carbonyl oxygen has electrostatic interactions with the backbone amide nitrogen of H352. Its hydroxyethyl substituent (R3/4) establishes H-bonding interactions with the side-chain of Y318 (both direct and water mediated) and the backbone carbonyl of S331. The carbon adjacent to the hydroxyethyl substituent also displays hydrophobic packing with the beta carbon of H352. In the crystal structure of Ldt$_{Mt1}$ with faropenem, electron density exists at a covalent distance to the active site C226 (2FoFc omit map contoured at 1.0σ) (FIG. 2d). An 86 Da adduct covalently attached to the catalytic C226 (equivalent to C354 of Ldt$_{Mt2}$) at an angle of 120° could be modeled into the density. Unlike with Ldt$_{Mt2}$, the same adduct makes different interactions in the active site of Ldt$_{Mt1}$. H208 (equivalent to H336 of Ldt$_{Mt2}$) does not interact with the sulfur of C226 but engages the carbonyl C7 oxygen in the faropenem adduct via electrostatic interactions. The hydroxyethyl side chain and the adjacent carbon of the adduct are stabilized by hydrophobic packing with two methylenes of the M175 side chain and with the β-carbon of H224 (equivalent to H352 of Ldt$_{Mt2}$). In addition, the hydroxyl group of the adduct forms a hydrogen bond with the side chain of Y190 (equivalent to Y318 of Ldt$_{Mt2}$).

Figure 2E:
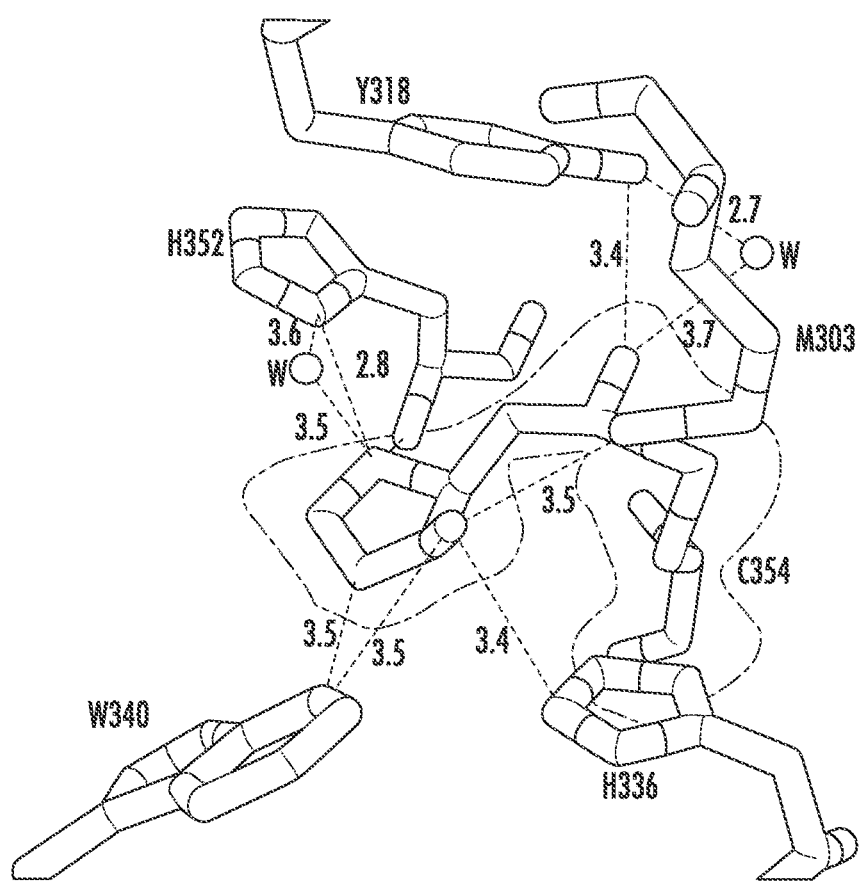

The orientation of doripenem bound to Ldt$_{Mt2}$ differs from that of faropenem. The 2Fo-Fc omit map (contoured at 1.0σ) also shows the doripenem adduct bound covalently to C354, but it extends into the outer cavity as bound by W340 (FIG. 2e). UPLC-MS analysis revealed this adduct to have a mass of 123 Da (FIG. 1a). Doripenem highly rearranged (by a proposed mechanism discussed below and shown in FIG. 2g), lacking its R1 and R2 substituents and its β-lactam ring opened (C7 bound to C354), could be modeled into the electron density. In the outer cavity, the C2 methyl on the pyrrolidine ring and the adjacent carbon in that ring of the adduct demonstrates van der Waals interactions with W340. The side-chain of Y318 and the backbone amide nitrogen of C354 form hydrogen bonds with the carbonyl C7 oxygen. The amino N4 of the pyrrolidine ring forms a hydrogen bond with the side-chain of H352.

Mechanism of L,D-Transpeptidase Inhibition

Figure 2F:
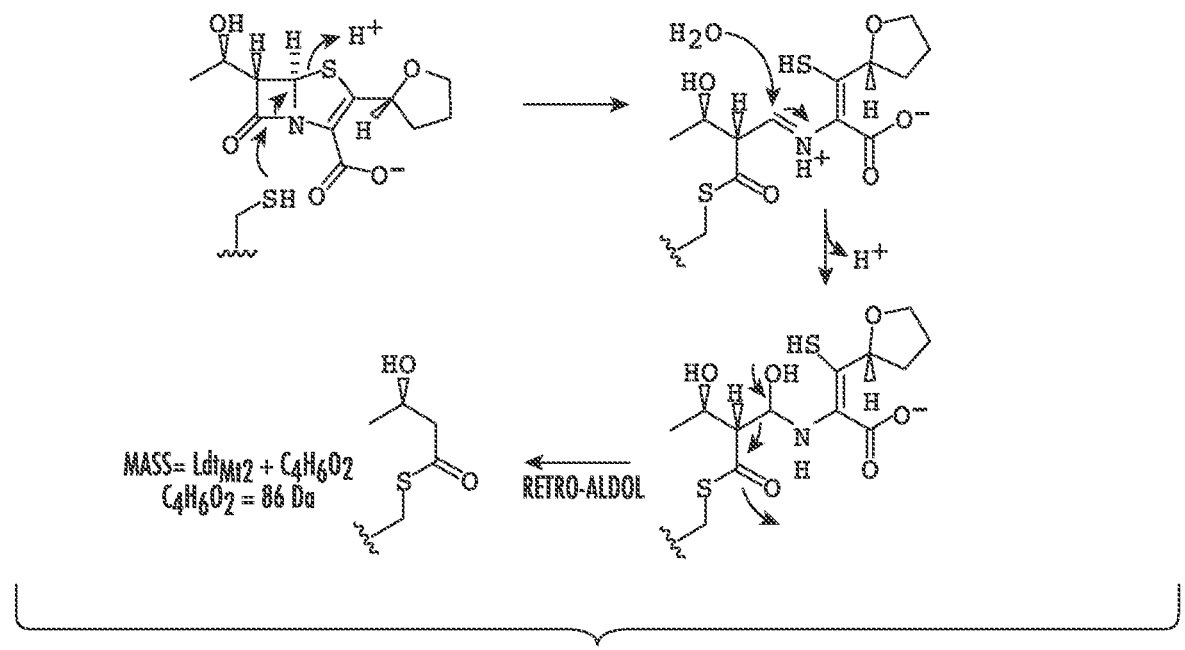

The reaction of faropenem (285 Da) with Ldt$_{Mt2}$ and Ldt$_{Mt1}$ was rapid and yielded the inactivated enzymes bearing only (R)-3-hydroxybutyryl covalently linked to the active site cysteine (C354 in Ldt$_{Mt2}$ and C226 in Ldt$_{Mt1}$) as depicted (FIG. 2f). Nucleophilic attack by this cysteine on the reactive β-lactam is proposed to open the 4-membered ring with further loss of the thioenol as shown. Such a cleavage process is well-precedented in the analogous masked enol opening of clavulanic acid by seryl β-lactamases. The resulting imine/iminium species, again paralleling clavulanate cleavage, is proposed to hydrate to an animal, whose facile retro-aldol scission affords the observed inactivated enzyme adduct.

Figure 2G:
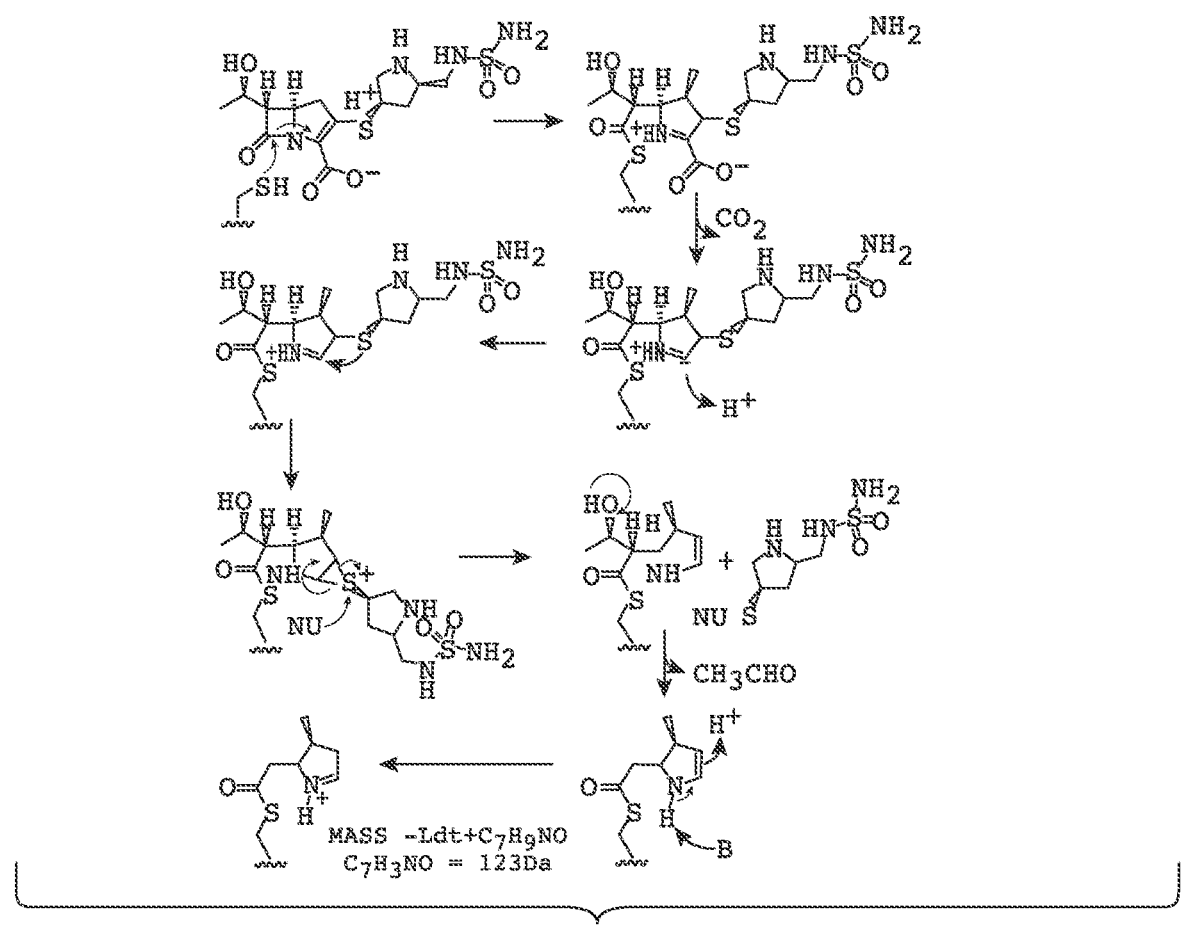

In contrast, reaction of the carbapenem doripenem (420 Da) at the Ldt$_{Mt2}$ catalytic center takes a different course, but not one driven by the formation of a stable (aromatic) pyrrole ring of unchanged oxidation state as expected. Instead, formation of the net two-electron reduced pyrrolinium adduct occurs H-bonded to the nearby H352. Specifically, attack of the active site cysteine on the carbapenem carbonyl is proposed to form an imine/iminium species shown, which may decarboxylate to a stabilized ylid, analogous to the active form of the cofactor thiamin. After protonation, the resulting pyrrolinium may be captured by the adjacent thioether and the resulting bridged sulfonium species, either by attack of a nucleophile or by reversible release of the enamine and scavenge of the sulfonium ion, achieves both the required two-electron reduction and preservation of the C1 and C5 stereocenters evident in the crystal structure. Subsequent to these events, or earlier, precedented retro-aldol reaction can ensue to expel the hydroxyethyl side chain as acetaldehyde (FIG. 2g).

Biapenem is Active Against *M. Tuberculosis* In Vivo

The main reason cited for lack of activity of β-lactams against *M. tuberculosis* is their hydrolysis by native β-lactamase, BlaC and poor permeability. Unlike other classes of (β-lactams, carbapenems are known to be slow substrates and thus effectively inhibitors of BlaC and exhibit robust in vitro activity against *M. tuberculosis* growth that is only slightly enhanced by the BlaC inhibitor clavulanic acid. Additionally, the bioavailability of carbapenems is suboptimal due to metabolism by dehydropepetidase-1 (DHP-1) in the renal proximal tubules. DHP-1 inhibitors such as cilastatin and probenecid have been used to protect and prolong the bioavailability of carbapenems. Early carbapenems meropenem and imipenem are known to exhibit limited activity when assessed in macrophages and mice infected with *M. tuberculosis*. A recent report described activity of faropenem in a mouse model of tuberculosis. In the study, faropenem medoxomil, a prodrug of faropenem, was provided by oral gavage. While faropenem medoxomil alone was ineffective, a modest reduction in M. tuberculosis burden in the lungs was observed in mice treated with a combination of faropenem medoxomil, clavulanate and probenecid. Here, we assessed antitubercular activity of faropenem and biapenem in the mouse model of tuberculosis by providing them subcutaneously. Initially known as LJC10627, biapenem has broad spectrum activity and is generally more potent than imipenem and other β-lactams. Unlike other existing carbapenems, biapenem is not readily metabolized by human DHP-1 and is well tolerated. As expected, all untreated mice succumbed to tuberculosis prior to the final time point. Gross pathological observations of the lungs of mice treated with biapenem alone or in combination with rifampicin for three weeks showed no tuberculous lesions that are hallmark of pathology in untreated mice (FIG. 3a-h, FIG. 15). In terms of M. tuberculosis burden in the lungs, biapenem alone was no less effective than rifampicin, a backbone drug of modern tuberculosis therapy. Notably, the combination of biapenem and rifampicin was at least as potent as isoniazid, a drug with the highest early bactericidal potency against M. tuberculosis among drugs used to treat tuberculosis, or a combination of isoniazid and rifampicin. While biapenem or rifampicin alone lacked bactericidal activity, the potent early bactericidal activity displayed by the combination suggests a potential in vivo synergy in activity between the two drugs similar to in vitro synergy that was recently described. Mice treated with faropenem developed tuberculous lesions in the lungs but their pathology and the bacterial burden were lower compared to untreated mice. Overall assessment of their health, which included total body weight during the course of the study, showed that faropenem, even when used alone, prolonged the life of mice infected with M. tuberculosis, although it did not cure the disease. Tuberculosis is treated with a regimen that involves multiple drugs. Therefore, biapenem (and faropenem to a limited extent) have the potential to lead to much needed new regimens to treat TB.

Evolved Carbapenems and Their Activities

Figure 16:
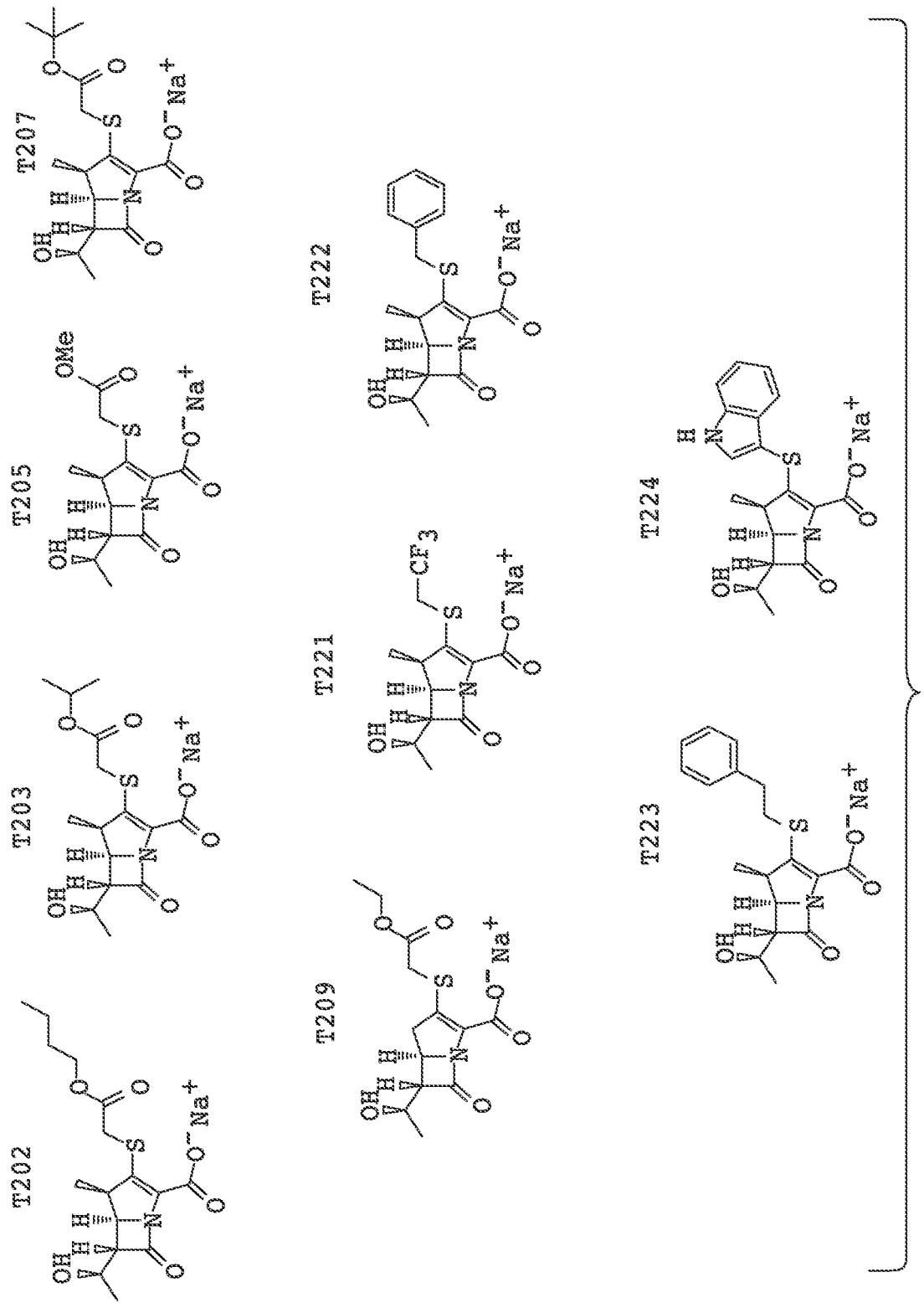
FIG. 16 illustrates Extended Data FIG. 7. Extended Data
Figure 17:
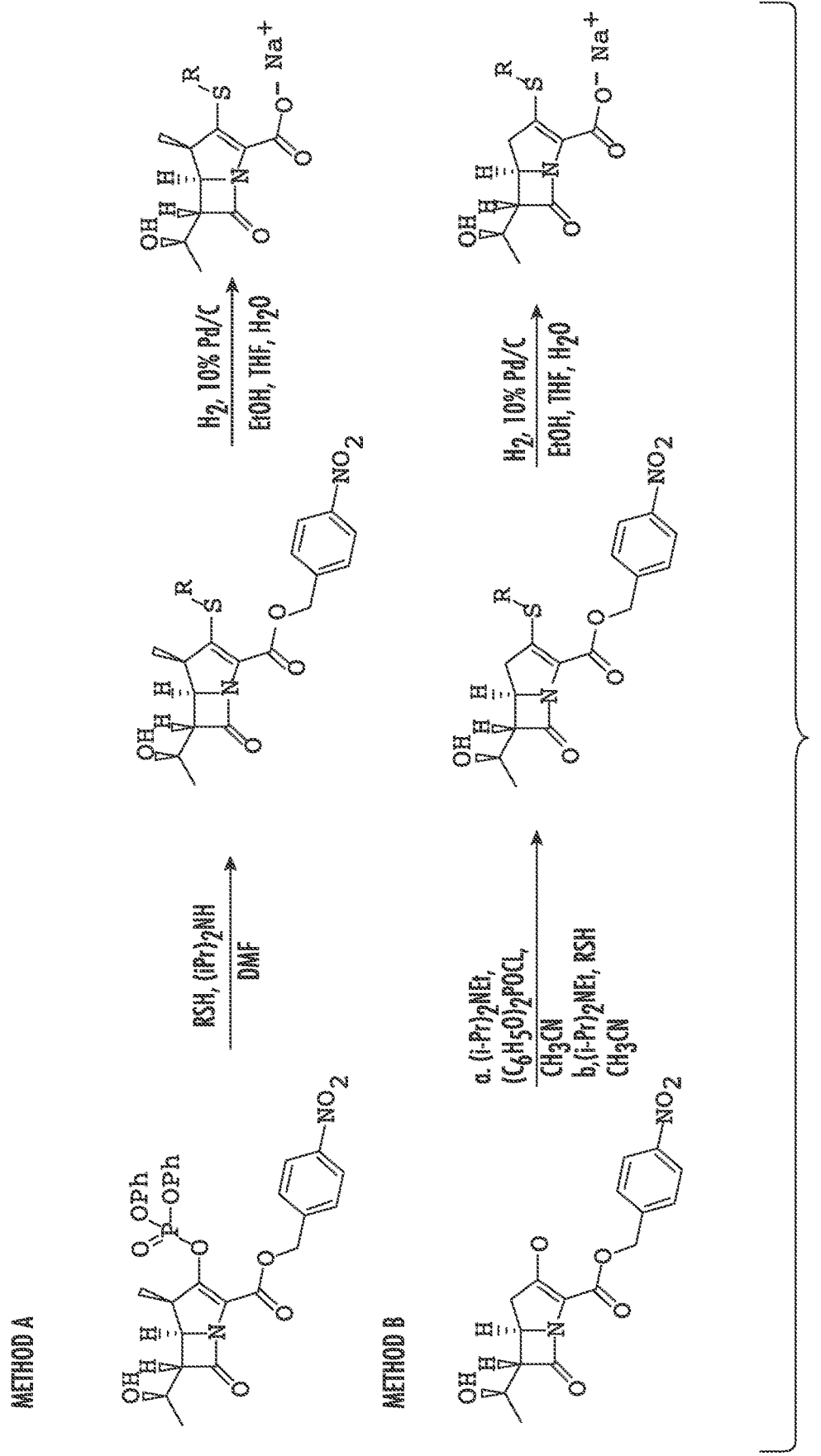
FIG. 17 illustrates Extended Data FIG. 8. Extended Data
Figure 19:
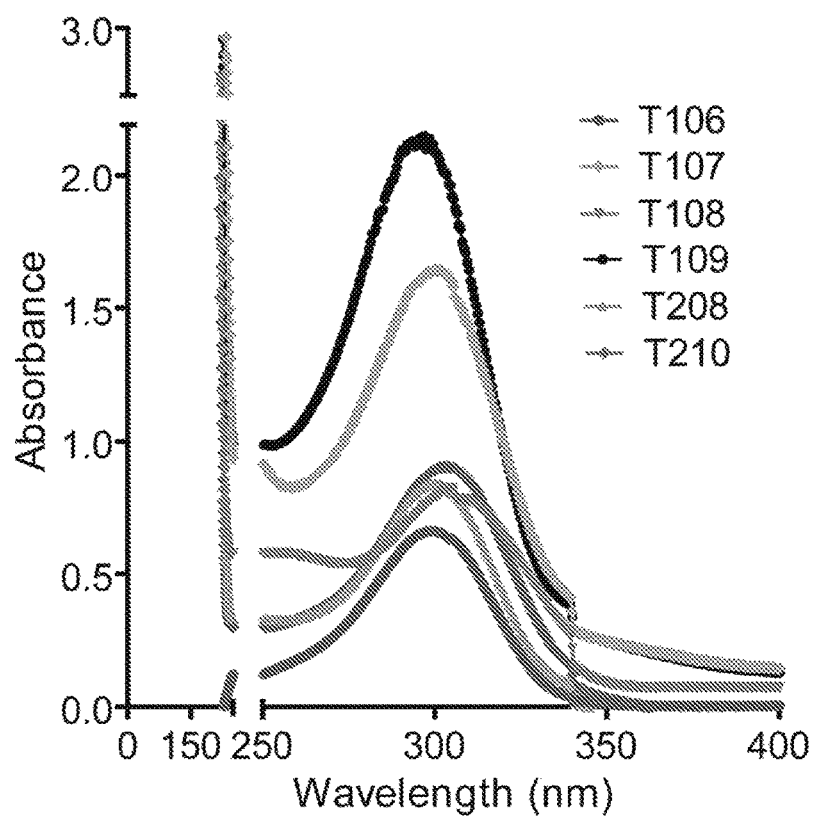
FIG. 19 illustrates Extended Data FIG. 10. Extended Data

The structure-activity data gathered on known carbapenems was used against L,D-transpeptidases to design new carbapenems. A key insight from the X-ray crystal structure of meropenem bound to $Ldt_{Mt2}$ is the absence of extensive contacts between the protein and the pyrrolidine-2-carboxamide thioether at C2. Not being held on any particular conclusion, it is possible that the pyrrolidine interacts mainly with solvent and, therefore, could be used to modify the physiochemical properties of the candidate inhibitors to enhance attributes such as Mtb permeability (and hence antitubercular whole-cell efficacy) and pharmacokinetic profile. Next the pyrrolidine of meropenem was replaced with various substituents demonstrated by our naïve Bayesian machine-learning models, to be highly correlated with antitubercular whole-cell efficacy (FIG. 16). We also noted observations of energetically favorable interactions made by the thioether substituents of doripenem, faropenem and tebipenem with L,D-transpeptidases through crystallography and ITC. These Bayesian models were constructed with commercially available software (Accelrys Discovery Studio 4.0) and trained with publicly available Mtb growth inhibition high-throughput screening data to distinguish actives from inactives given a specified efficacy cutoff. In the case of whole-cell active sulfides, there was a prevalence of active molecules with an —$SCH_2CO_2R$ (R=$CH_3$, $CH_2CH_3$, $(CH_2)_2CH_3$, $CH(CH_3)_2$, $C(CH_3)_3$, $(CH_2)_3CH_3$, c-$C_6H_{12}$) moiety as well as —S(2-pyridyl). Additionally, we examined a "minimalist"—$SCH_3$ moiety as well as thioether substituents. Follow-up compounds to this initial series included —SR (R=$CH_2CH_3$, $CH_2CF_3$, $CH(CH_3)_2$, $C(CH_3)_3$, $CH_2C_6H_5$, $(CH_2)_2C_6H_5$, 3-indole). Initial effort focused on the 2-substituted analogs of existing carbapenems with an emphasis on R1 substituent to disrupt critical residues in the catalytic site of L,D-transpeptidases. Synthesis of the final carbapenems followed a two-stage process (FIG. 17) where the commercially available enol phosphate and thiol (or immediate precursor) were reacted to afford the desired thioether. The 4-nitrobenzyl ester protecting group was then cleaved to yield the desired carbapenem as the sodium salt post-purification by HPLC. It should be noted that while T210, T218, T201, T204, and T222 have been synthesized previously by other groups, we are not aware of any reports of their antitubercular efficacy.

We began by assessing in vitro growth inhibitory activities of these evolved carbapenems by determining minimum inhibitory concentration ($MIC_{90}$) against M. tuberculosis, M. abscessus, Gram negatives A. baumannii, K. pneumoniae, E. cloacae and P. aeruginosa, and Gram positives E. faecalis and S. aureus. Of the 42 experimental carbapenems we prepared (Extended Data FIG. 9 and data not shown), 14 exhibit $MIC_{90}$ values in the low to sub μg/mL, concentrations that are potentially therapeutically valuable (FIG. 1b). While none of the compounds inhibited growth of M. abscessus, some displayed relatively broad-spectrum activities and many were active against only select pathogens. For instance, T221, T222, T223 and T224 inhibit growth of all tested pathogens except P. aeruginosa. On the other hand, T123 displayed activity against P. aeruginosa. Apparent selectivity or lack thereof in activity of the experimental carbapenems among the panel of pathogens assessed is not clear from the structures and known chemical properties alone. Further investigations of targets inhibited by the compounds in each organism would be necessary to unveil the underlying mechanisms of action.

Next it was determined if the evolved carbapenems could bind and react with L,D-transpeptidases. For this task, we studied T205, T206, T208 and T210 against $Ldt_{Mt1}$, $Ldt_{Mt2}$, $Ldt_{Mab1}$, $Ldt_{Mab2}$, $Ldt_{Kp}$, $Ldt_{Cl}$, and $Ldt_{Pa}$. All evolved carbapenems reacted and formed covalent adducts whose masses showed acylation of the enzymes with retention of the complete inactivator with the exception of $Ldt_{Mab2}$ (and $Ldt_{Pa}$ against T206), which did not react with the compounds (FIG. 1a). It was consistently observed that the entire drug molecule (with a loss of a sodium atom) bound to the L,D-transpeptidases from five different organisms suggesting a similar mechanism of action for each carbapenem.

$Ldt_{Mt2}$ was used as a representative target to assess kinetics of acylation by the evolved carbapenems. $k_{inact}$ and $K_{app}$ for T208 and T210 are (2.7±0.2 $min^{-1}$ and 4.8±2.9 μM with $r^2$=0.85) and (1.5±0.1 $min^{-1}$ and 20.8±3.3 μM with $r^2$=0.95), respectively (FIG. 3b). The $k_{inact}/K_{app}$ ratio of 0.56 and 0.07 $min^{-}μM^{-1}$ demonstrate that these experimental carbapenems are effective acylators of $Ldt_{Mt2}$ and at least as efficient as meropenem, doripenem, biapenem, faropenem and tebipenem in inactivating the enzyme. Assessment of binding affinities of T206, T208 and T210 with $Ldt_{Mt2}$ and $Ldt_{Mab2}$ revealed $K_d$ in the low to sub μM range demonstrating strong binding of these carbapenems by the enzymes (FIG. 6). Unlike faropenem, the evolved carbapenems show positive enthalpy change and their bindings are entropically driven. $Ldt_{Mt2}$ mutants Y381F, H336N, H352N and C354S all displayed poor binding affinities to T210 (FIG. 6) demonstrating that alterations in the catalytic site disrupt interaction of the enzyme with the carbapenem. These data suggest that T210 requires Y318, H336, H352 and C354 for favorable binding.

Structure with Evolved Carbapenems

The crystal structures of $Ldt_{Mt2}$ in complex with T206, T208 and T210. T206 binds in two different orientations in the active site of the enzyme, via the outer cavity (conformation A) or via the inner cavity (conformation B), in two different crystal structures (FIG. 4c). The 2Fo-Fc omit map (contoured at 1.0σ) of T206 in conformation A, shows this carbapenem interacting with the outer cavity and covalently attached to the catalytic C354. The carbonyl oxygen hydrogen bonds with the backbone amide nitrogen of C354. The electron density of carbapenem T206 is contiguous to the $S^\gamma$ atom of C354, but it is missing for much of the R1 group beyond the thioether sulfur. This sulfur exhibits electrostatic interactions with the hydroxyl in the side chain of T320. The hydroxyl of the R2 group hydrogen bonds with the side chain of Y318 and displays both a direct and a water-mediated hydrogen bond with the backbone carbonyl of G332. The carboxyl group at C3 of the pyrrolidine ring forms hydrogen bonds with the side chains of N356 and W340 and with the backbone amide of H352. W340 also has hydrophobic interactions with the alkyl tail of the R1 group of T206. In conformation B, the carbonyl C7 (of what was the β-lactam ring) is covalently bound to C354, with the rest of the molecule extending into the inner cavity of the active site, similar to previous crystal structures of the meropenem: $Ldt_{Mt2}$ complexes. The carbonyl oxygen is hydrogen bonded to the backbone N—H of C354. The pyrrolidine ring and its carboxylate substituent have a conformation similar to the corresponding substructure of meropenem in chain A of PDB ID: 4GSU and in conformation A of chain A of PDB ID: 3VYP, but this ring is rotated with respect to the orientation observed in the other chains of 4GSU and 3VYP. Interestingly, T206 is fully ordered in conformation B, with its R1 group tail being stabilized by hydrophobic interactions with residues P286 and T285 and by a network of water-mediated hydrogen bonds between the carboxylate of T206 and the side-chain S331, the backbone amide nitrogen of A288, and the backbone carbonyl oxygen of P286. The hydroxyl of the R2 group also displays electrostatic interactions with the sulfur in the side chain of M303, and the thioether linker has a weak electrostatic interaction with the hydroxyl of Y318.

In the crystal structure of $Ldt_{Mt2}$ with T208 and T210, their 2Fo-Fc maps contoured at 1.0σ show electron density for the respective inhibitors (and specifically the carbonyl carbon of what was the β-lactam moiety) within a covalent distance from C354 (FIGS. 4d,e). Both T208 and T210 extend into the outer cavity, in a manner similar to conformation A of T206 and that of imipenem with $Ldt_{Mt1}$ (PDB ID: 4JMX). The conserved region of T206, T208, and T210 forms the same quaternary interactions with the outer cavity of $Ldt_{Mt2}$. In all of the evolved carbapenems bound in the outer cavity, electron densities for the methyl group of the pyrrolidine ring at C1 position and the R1 group tail after the thioether sulfur are missing. T206, T208 and T210 acylate $Ldt_{Mt2}$ with the same mechanism: sulfur of C354 resulting initiates a nucleophilic attack on C7 and opens the β-lactam ring (FIG. 4f).

EXAMPLES/METHODS

Bacterial Strains, Growth Media and Drugs

The following bacterial strains were used in this study: *M. tuberculosis* H37Rv, *M. abscessus* (ATCC 19977), *A. baumannii* (strain GM-1b, Clinical Microbiology, Johns Hopkins University), *K. pneumoniae* (ATCC 35657), *E. cloacae* (ATCC 13047), *P. aeruginosa* (PA14), *E. faecalis* (ATCC 19433), Methicillin sensitive *S. aureus* (ATCC 29213) and Methicillin resistant *S. aureus* (ATCC 43300). *M. tuberculosis* was grown and assessed in Middlebrook 7H9 broth (Difco) supplemented with 0.5% glycerol, 10% oleic acid-albumin-dextrose-catalase and 0.05% Tween 80. *M. abscessus* was grown in Middlebrook 7H9 broth with albumin-dextrose-catalase enrichment with constant shaking at 37° C. Cation-adjusted Mueller-Hinton broth (Becton-Dickinson) was used to grow *A. baumannii*, *K. pneumoniae*, *E. cloacae*, *P. aeruginosa*, *E. faecalis* and *S. aureus* at 35° C. as per Clinical and Laboratory Standard Institute (CLSI) guidelines.[51] Rifampicin, isoniazid, meropenem, imipenem, doripenem, biapenem, faropenem and tebipenem were obtained from commercial vendors (Sigma-Aldrich, Toronto Research Chemicals). Compounds were 95%-99% pure when random samples were analyzed using liquid chromatography-mass spectrometry.

Cloning, Site Directed Mutagenesis, Expression and Purification of Proteins

L,D- and D,D-transpeptidases in general possess an N-terminal transmembrane anchoring domain. This domain was excluded during cloning to facilitate soluble proteins overexpression and purification. For most proteins, multiple fragments were cloned, expressed and purified to enhance chances of obtaining apo and co-crystals with drugs (FIG. 5). Desired gene fragments were cloned into the multiple cloning site in pET28a+ to afford a N-terminal His6 (SEQ ID NO: tagged protein cleavable by TEV, Single amino acid substitutions of $Ldt_{Mt2}$ (fragment ΔN55) were constructed as follows. Primers were designed such that mutations resulting in amino acid substitution were placed at the center of the oligo (FIG. 5). For each mutagenesis, two separate PCR reactions, each with forward or reverse primer, using NEB high-fidelity buffer was used to amplify pET28a+vector carrying wild-type sequence for $Ldt_{Mt2}$ (fragment ΔN55). DNA from the two reactions were combined, denatured at 95° C., slowly renatured to 37° C. and digested with Dpn I as described. *E. coli* DH5α (C2987H, NEB Labs) was used for cloning and manipulation of plasmids. *E. coli* BL21δε3 (C2527H, NEB Labs) was used to overexpress proteins as described.

Mass Spectrometry

Ultra-performance liquid chromatography-high resolution mass spectrometry (UPLC-MS) with a Waters Acquity H-Class system utilizing a Waters Acquity BEH-300 UPLC column packed with a $C_4$ stationary phase (2.1×50 mm, 1.7 µm) in conjunction with HRMS analysis by a Waters Xero-G2 quadropole-TOF electrospray mass spectrometer was used to detect and analyze protein-drug adducts. Each enzyme (2 µM) in 25 mM Tris buffer, pH 8, was incubated in the absence or presence of drugs (50 µM) at room temperature for 5 hours. Trifluoroacetic acid (0.1% final) was used to quench the reactions, samples were filtered through a 0.22 um filter and analyzed using UPLC-MS as follows: Mobile phase: 0-1 min 90% water+10% ACN+0.1% formic acid, 1-7.5 min gradient up to 20% water+80% ACN+0.1% formic acid, 7.5-8.4 min 20% water+80% ACN+0.1% formic acid, 8.4-8.5 min gradient up to 90% water+10% ACN+0.1% formic acid, 8.5-10 min 90% water+10% ACN+0.1% formic acid. Flow rate=0.3 mL min$^{-1}$. T=60° C.

Isothermal Titration Calorimetry

Ligands and proteins were solubilized in buffer 50 mM tris pH 8.0, 150 mM NaCl, 0.5 mM TCEP. calorimetry experiments were performed using a microcalorimeter (iTC$_{200}$, MicroCal, MA, USA) at 24° C., by titration of the ligand (1×0.5 μL+16×2.5 μL injections at 280 s intervals; stirring speed of 1000 rpm). Titrations of ligands into buffer were performed as a control, and the resulting heats of ligand dilution were subtracted from the experimental data prior to curve fitting. MicroCal Data Analysis software, Auto-iTC200 was used to determine the thermodynamic properties of ligand binding using non-linear least-squares fitting assuming a single-site model. For interactions between Ldt$_{Mab2}$ and new carbapenems, thermodynamic properties of binding were calculated using non-linear least-squares fitting assuming sequential two site binding model.

Determination of Catalytic Constants

The acylation kinetics of Ldt$_{Mt2}$ were determined by measuring the reduction in absorbance of the carbapenems following β-lactam ring opening using a UV/Vis spectrophotometry (Shimadzu UV1800). The kinetics of acyl-enzyme complex formation were determined by incubating 10 μM Ldt$_{Mt2}$ with increasing concentrations of drugs in a buffer containing MES (100 mM; pH 6.5), 150 mM NaCl and 0.05 mM TCEP. The assays were performed at 10° C. to reduce the rate of reactions, similar to previous investigations via stopped-flow/fluorescence approach. The reduction in carbapenem absorbance was used to compute the rate of acyl-enzyme complex formation, which was then plotted as a function of the concentration of various carbapenems assayed at their $\lambda_{max}$ (FIG. 10). The absorption coefficients (molar absorptivities) in buffer containing 100 mM MES, pH 6.5 were determined to be 7500 M$^{-1}$ cm$^{-1}$ for doripenem, 6980 M$^{-1}$ cm$^{-1}$ for faropenem, 9845.7 M$^{-1}$ cm$^{-1}$ for biapenem, 6652 M$^{-1}$ cm$^{-1}$ for tebipenem, 9900 M$^{-1}$ cm$^{-1}$ for T208 and 9880 M$^{-1}$ cm$^{-1}$ for T210. The $k_{inact}$ (maximum rate at which an irreversible enzyme-inhibitor complex occurs), and $K_{app}$ (inhibitor concentration required to achieve half of $k_{inact}$). The $K_{inact}$ and $K_{app}$ values were calculated using non-linear regression analysis.

Protein Crystallization

Purified Ldt$_{Mt2}$ (fragment ΔN55) was dialyzed against the buffer 50 mM tris pH 8.0, 150 mM NaCl, 0.5 mM TCEP and concentrated to 21 mg/ml. The crystallization screens Hampton Crystal Screen HT, JBScreen JCSG++HTS and JBScreen PEG/Salt HTS were used to identify crystallization conditions using the sitting drop vapor diffusion method. Plate-like crystals were appeared in 20% 5000MME and 200 mM ammonium sulfate condition within a week and these crystals were used as seeds to produce better quality crystals by the hanging drop vapor diffusion method. For co-crystallization of Ldt$_{Mt2}$ with faropenem and doripenem, enzyme was incubated with 5 mM of each drug for 2 hours at room temperature and crystallization trays were set up with the vapor diffusion method. For crystallization of Ldt$_{Mt2}$ with evolved drugs T206, T208 and T210, Ldt$_{Mt2}$ crystals were soaked overnight with 1-2 mM of each drug.

Purified Ldt$_{Mt1}$ (fragment ΔN31) at a concentration of 16 mg/ml was crystallized using the sitting drop vapor diffusion method with 10% PEG6000 and 100 mM Bicine pH 9.0. Crystals from a preliminary screen were used as seeds for further production of good quality crystals by the hanging drop vapor diffusion method. For co-crystallization of Ldt$_{Mt1}$ with faropenem, 10 mM of drug was mixed with enzyme and incubated for 2 hours at room temperature before setting up crystallization condition using the hanging drop vapor diffusion method.

Crystal Diffraction and Data Collection

Ldt$_{Mt2}$-apo, co-crystals as well as crystals soaked with carbapenem drugs were cryo-protected in 30% glycerol, 20% 5000 MME and 120 mM ammonium sulfate buffer and flash cooled in liquid nitrogen. For Ldt$_{Mt2}$-apo and co-crystals with faropenem and doripenem, X-ray diffraction data were collected at a wavelength of 1.54 Å using an in-house CuKα X-ray source (Rigaku FR-E+SuperBright generator with a Saturn 944+ CCD Detector; Rigaku, The Woodlands, Tex., USA). For Ldt$_{Mt2}$ apo and crystals soaked with evolved the carbapenems T206, T208 and T210, diffraction data were collected at 100K at a wavelength of 0.98 Å on beamline 19-ID at the Advanced Photon Source (Argonne National Laboratory) and the diffraction data were recorded on an ADSC Quantum 315r CCD detector, and processed with HKL3000.

Ldt$_{Mt1}$-apo and co-crystal with faropenem were cryoprotected with 30% PEG8000, 10% PEG6000 and 100 mM Bicine pH 9.0 buffer and flash cooled in liquid nitrogen. The X-ray diffraction data were collected and analyzed as described above.

Structure Determination

The Ldt$_{Mt2}$-apo crystals belong to the primitive triclinic space group P1 with four molecules in the asymmetric cell. The crystal structure of Ldt$_{Mt2}$ was solved by molecular replacement method using the program, PHASER-MR from the CCP4 suite of programs using the coordinates of Ldt$_{Mt2}$ (PDB ID: 3VYN) as a search model. The initial solution was subjected to multiple rounds of crystallographic refinement with REFMAC 5.8.0103 from the CCP4 suite of programs and rebuilt to fit the electron density with COOT. The R values of refined structure (FIG. 8) are well within the range of typical resolution. Ramachandran analysis with MolProbity indicated that 96.46% residues are under favorable region and 3.54% in additional allowed region. The Ldt$_{Mt2}$ crystals with different carbapenem drugs (faropenem, doripenem, T206, T208 and T210) belong to the primitive monoclinic space group P2$_1$ with two molecules in the asymmetric unit. The crystal structures of Ldt$_{Mt2}$ with carbapenem drugs were solved by the molecular replacement method using the program, PHASER-MR, either in Phenix or the CCP4 suite of programs. The initial solutions of Ldt$_{Mt2}$ with different carbapenem drugs were subjected to multiple rounds of crystallographic refinement with program, REFMAC 5.8.0103 from the CCP4 suite of programs or with program phenix.refine from the Phenix suite of programs, and rebuilt to fit the electron density with COOT. The R values of refined structures (extended Data Table 4 and 5) are well within the range that is typical at corresponding resolution. Ramachandran analysis with MolProbity indicated that, in the structure of Ldt$_{Mt2}$-faropenem, 96.69% residues are under favorable region and 3.02% in additional allowed region. In the structure of Ldt$_{Mt2}$-doripenem, 97.56% residues are under favorable region and 2.44% in additional allowed region. In the structure of Ldt$_{Mt2}$-T206_A, 96.12% residues are under favourable region and 3.74% in additional allowed region. In the structure of Ldt$_{Mt2}$-T206_B, 96.12% residues are under favorable region and 3.59% in additional allowed region. In the structure of Ldt$_{Mt2}$-T208, 96.55% residues are under favourable region and 3.16% in additional allowed region. In the structure of Ldt$_{Mt2}$-T210, 96.56% residues are under favorable region and 3.16% in additional allowed region. The crystallographic parameters and final refinement statistics are summarized in FIGS. 8 and 9. 2Fo-Fc difference Fourier maps were calculated for all different carbapenems bound to the active site of Ldt$_{Mt2}$ using calculate maps in Phenix Suite and figures were prepared using PyMOL Molecular Graphics System, Version 1.5.0.4 Schrödinger, LLC.

The Ldt$_{Mt1}$-apo and co-crystal structures with faropenem belong to the primitive trigonal space group P3$_1$ with four molecules in the asymmetric unit. Since the two axis a and b are equal in the space group, analysis of data quality with Xtriage from the Phenix suite of programs suggested three 2-fold merohedral twin operators (−h,−k,l; h,−h−k,−l; and −k,−h,−l). The crystal structure of Ldt$_{Mt1}$ was solved by molecular replacement using PHASER-MR from the Phenix suite of programs. The coordinates of Ldt$_{Mt1}$ (PDB ID: 4JMN) were used as search models. The initial solution was further built using Autobuild (Automated model building and refinement) from the Phenix suite of programs. The output model from Autobuild was further subjected to multiple rounds of NCS-based (non-crystallographic symmetry) crystallographic refinement using the program phenix.refine from the Phenix suite of programs and the twin law (−h,−k,l) was applied during the refinement cycles. The structure was rebuilt to fit the electron density with COOT. The R values of refined structures (FIG. 8) are well within the range that is typical at corresponding resolution. Ramachandran analysis with MolProbity indicated that, in the structure of Ldt$_{Mt1}$-apo, 94.69% residues are under favorable region and 4.77% in additional allowed region and in the structure of Ldt$_{Mt1}$-faropenem, 94.01% residues are under favorable region and 5.45% in additional allowed region. The crystallographic parameters and final refinement statistics are summarized in Extended Data Table 4. Coordinates and structure factors have been deposited in the PDB with the following accession numbers: 5DU7, 5DUJ, 5DVP, 5E5L, 5E51, 5DZJ, 5DZP, 5E1G and 5E1I.

Design and Synthesis of Evolved Carbapenems

All reagents were purchased from commercial suppliers and used without further purification unless otherwise noted. All chemical reactions occurring solely in an organic solvent were carried out under an inert atmosphere of argon or nitrogen. Analytical TLC was performed with Merck silica gel 60 F254 plates. Silica gel column chromatography was conducted with Teledyne Isco CombiFlash Companion or Rf+ systems. $^1$H NMR spectra were acquired on Varian Inova 400, 500 and 600 MHz instruments and are listed in parts per million downfield from TMS. LC-MS was performed on an Agilent 1260 HPLC coupled to an Agilent 6120 MS. All synthesized compounds were at least 95% pure as judged by their HPLC trace at 250 nm and were characterized by the expected parent ion(s) in the MS trace. General Procedure A (Meropenem type): T205: sodium (4R,5S,6S)-6-((R)-1-hydroxyethyl)-3-((2-methoxy-2-oxoethyl)thio)-4-methyl-7-oxo-1-azabicyclo[3.2.0]hept-2-ene-2 carboxylate To a solution of 4-nitrobenzyl (4R,5S,6S)-3-Rdiphenylphosphono)oxyl-6-[(R)-1-hydroxyethyl]-4-methyl-7-oxo-1-azabicyclo[3.2.0]hept-2-ene-2-carboxylate (250 mg, 0.42 mmol) in 2.5 mL DMF was added methyl thioglycolate (0.046 mL, 0.51 mmol) and diisopropylamine (0.071 mL, 0.51 mmol) at 0° C. The reaction mixture was stirred for 70 min at 0° C. The reaction mixture was diluted with 40 mL of ethyl acetate. The organic solution was washed with 3×5 mL of water and 5 mL of saturated brine solution. The organic solution was dried over anhydrous magnesium sulfate, filtered, and dried in vacuo. The product was purified by flash column chromatography on silica gel, eluting with a mixture of CH$_2$Cl$_2$ and MeOH to afford (4R,5S,6S)-4-nitrobenzyl 6-((R)-1-hydroxyethyl)-3-((2-methoxy-2-oxoethyl)thio)-4-methyl-7-oxo-1-azabicyclo[3.2.0]hept-2-ene-2-carboxylate as a white solid in 95% yield (179 mg).

A 10 mL pear shaped flask was charged with 10% Pd/C (31 mg) and 1.0 mL of H$_2$O. Hydrogen was bubbled through the mixture for 50 min. NaHCO$_3$ (6.0 mg, 0.071 mmol), 1.0 mL EtOH and 6-((R)-1-hydroxyethyl)-3-((2-methoxy-2-oxoethyl)thio)-4-methyl-7-oxo-1-azabicyclo[3.2.0]hept-2-ene-2-carboxylate (30 mg in 1.0 mL THF, 0.067 mmol) were added. Hydrogen was bubbled through the reaction mixture for 1 h at room temperature. Pd/C was removed by filtration through a pad of Celite that was washed with 6 mL of water. The filtrate was extracted with CH$_2$Cl$_2$ (2×2 mL) and Et$_2$O (2 mL). The aqueous phase was purified by HPLC on a C18 column, eluting with water and acetonitrile to give the desired product as a white fluffy powder in 62% yield (14 mg): $^1$H NMR (600 MHz, D$_2$O) 4.13-4.07 (m, 1), 4.05 (dd, J=9.1, 2.5 Hz, 1), 3.66-3.59 (m, 4), 3.43 (d, J=15.7 Hz, 1), 3.32-3.25 (m, 2), 1.15 (d, J=6.4 Hz, 3), 1.02 (d, J=7.3 Hz, 3). General Procedure B (Imipenem type): T209: sodium (5R,6S)-3-((2-ethoxy-2-oxoethyl)thio)-6-((R)-1-hydroxyethyl)-7-oxo-1-azabicyclo[3.2.0]hept-2-ene-2-carboxylate:

To a solution of (5R,6S)-4-nitrobenzyl6-((R)-1-hydroxyethyl)-3,7-dioxo-1-azabicyclo[3.2.0]heptanecarboxylate (150 mg, 0.43 mmol) in 5 mL acetonitrile was added N,N-diisopropylethylamine (0.097 mL, 0.56 mmol) and diphenyl chlorophosphate (0.116 mL, 0.56 mmol) at 0° C. The reaction mixture was stirred for 45 min at 0° C. Then N,N-diisopropylethylamine (0.097 mL, 0.56 mmol) and ethyl thioglycolate (0.061 mL, 0.56 mmol) were added. The reaction mixture was stirred for 1 h at 0° C. and then diluted with 50 mL of ethyl acetate. The organic solution was washed with 3×5 mL of water and then 5 mL of saturated brine solution. The organic solution was dried over anhydrous magnesium sulfate, filtered, and dried in vacuo. The product was purified by flash column chromatography on silica gel, eluting with a mixture of dichloromethane and ethyl acetate to give (5R,6S)-4-nitrobenzyl 3-((2-ethoxy-2-oxoethyl)thio)-6-((R)-1-hydroxyethyl)-7-oxo-1-azabicyclo[3.2.0]hept-2-ene-2-carboxylate as a white solid in 74% yield (144 mg).

A 10 mL pear shaped flask was charged with 10% Pd/C (25 mg) and 1.0 mL of H$_2$O. Hydrogen was bubbled through the mixture for 50 min. NaHCO$_3$ (6.4 mg, 0.076 mmol), 1.0 mL EtOH, and 3-((2-ethoxy-2-oxoethyl)thio)-6-((R)-1-hydroxyethyl)-7-oxo-1-azabicyclo[3.2.0] hept-2-ene-2-carboxylate (30 mg in 1.0 mL THF, 0.067 mmol) were added. Hydrogen was bubbled through the reaction mixture for 1 h at room temperature. Pd/C was removed by filtration through a pad of Celite that was washed with 6 mL of water. The filtrate was extracted with CH$_2$Cl$_2$ (2×2 mL) and Et$_2$O (2 mL). The aqueous phase was purified by HPLC on a C18 column, eluting with water and acetonitrile to give the desired product as a white fluffy powder in 38% yield (8.5 mg). $^1$H NMR (600 MHz, D$_2$O) δ4.13-4.01 (m, 4), 3.59 (d, J=16.3 Hz, 1), 3.50 (d, J=16.4 Hz, 1), 3.25 (dd, J=6.0, 2.6 Hz, 1), 3.10 (dd, J=17.3, 9.7 Hz, 1), 2.95 (dd, J=17.3, 8.6 Hz, 1), 1.17-1.05 (m, 6).

Minimum Inhibitory Concentration

The standard broth dilution method was used to determine Minimum Inhibitory Concentration (MIC$_{90}$) of drugs and experimental carbapenems. Briefly, each bacterial strain was grown in appropriate media under aforementioned conditions to exponential phase and the cultures were used to inoculate 10$^5$ colony forming units (CFU) into microtiter wells containing a drug at two fold dilutions ranging from 64

μg/ml to 0.06 μg/ml. Medium inoculated with bacteria but without drug was used as a positive control for growth. The negative control was medium alone. As per CLSI guidelines cultures were incubated at 37° C. and evaluated for growth by visual inspection at 14 days for *M. tuberculosis* and at 3 days for *M. abscessus* at 30° C. Similarly, MIC assessments for *A. baumannii, K. pneumoniae, E. cloacae, P. aeruginosa, E. faecalis* and *S. aureus* were performed as per CLSI guidelines. Experiments were repeated to verify $MIC_{90}$ results.

Evaluation of Carbapenems in Mice

Female BALB/c mice, 4-5 weeks old (Charles River Labs), were used according to the protocol approved by the Johns Hopkins University Animal Care & Use Committee (MO15M25). We used an acute model of active *M. tuberculosis* infection in mice to assess the activities of faropenem and biapenem. Mice were infected via the aerosol route using a Glas-Col chamber and a dose to deliver approximately ~1000 CFU in the lungs. Mice were treated three days after infection, a time when *M. tuberculosis* bacilli are rapidly proliferating. While isoniazid (10 mg/kg) and rifampicin (10 mg/kg) were administered by oral gavage once daily, 7 days per week, biapenem (200 mg/kg) and faropenem (200 mg/kg) were administered twice daily by subcutaneous injection. Five mice were sacrificed one day after infection, lungs homogenized and plated on Middlebrook 7H11 selective medium to determine the actual infection burden. Next, five mice were sacrificed on the day of treatment initiation and at three weeks following initiation of treatment, the final time point, to determine bacterial burden in the lungs. Gross pathology of lungs and mouse body weights were recorded at each time point.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Embodiments of the disclosure concern methods and/or compositions for treating and/or preventing bacterial infections in which the inactivation of L,D-transpeptidases is directly or indirectly related. In certain embodiments, individuals with a bacterial infection are treated with an inhibitor of L,D-transpeptidases.

In certain embodiments, the level to which inactivation of L,D-transpeptidases may be any level so long as it provides amelioration of at least one symptom of the bacterial infection. The level of inactivation may be at least 2, 3, 4, 5, 10, 25, 50, 100, 1000, or more fold expression compared to the level of expression in a standard, in at least some cases.

An individual known to have a bacterial infection, suspected of having a bacterial infection, or at risk for having bacterial infection may be provided an effective amount of an inducer of an inactivator of L,D-transpeptidase, including one or more compounds of the present invention.

In particular embodiments of the disclosure, an individual is given an agent for a bacterial infection in addition to the one or more compounds of the present invention. When combination therapy is employed, the additional therapy may be given prior to, at the same time as, and/or subsequent to the one or more compounds of the present invention.

Pharmaceutical Preparations

Pharmaceutical compositions of the present invention comprise an effective amount of one or more inactivators of L,D-transpeptidases such as the compounds of the present invention, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one compound of the present invention or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compounds of the present invention comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof).

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more compound of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the one or compound of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In one embodiment of the present disclosure, the one or more compounds of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the one or more compounds of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the one or more compounds of the present invention may be formulated for administration via various miscellaneous routes, for example, topical (i.e., transdermal) administration, mucosal administration (intranasal, vaginal, etc.) and/or inhalation.

Pharmaceutical compositions for topical administration may include the one or more compounds of the present invention formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an inactivator of L,D-transpeptidase (for example, one or more compound of the present invention) may be comprised in a kit.

The kits may comprise a suitably aliquoted of the one or more compounds of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or compounds of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more compounds of the present invention and/or composition(s) thereof may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The invention claimed is:

1. A compound of Formula (I):

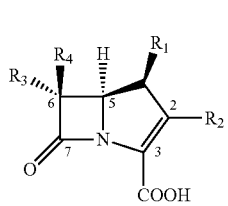

(I)

wherein:
R1 is —H or —CH3;
R2 is

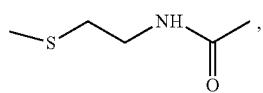

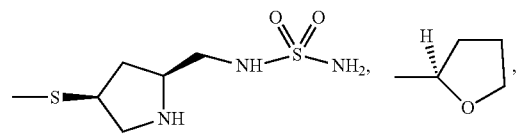

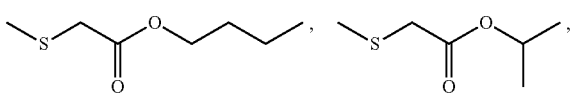

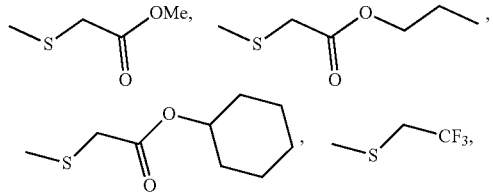

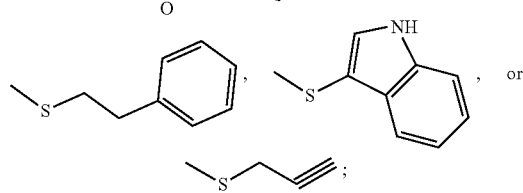

R3 is H,

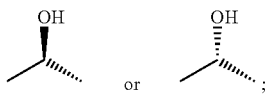 or 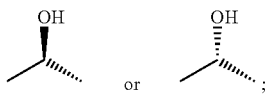;

and
R4 is H,

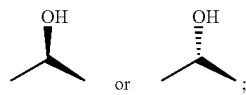 or 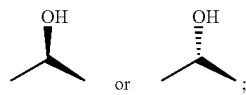;

or a pharmaceutically acceptable salt, solvate, or stereoisomer thereof.

2. The compound, salt, solvate, or stereoisomer of claim 1, wherein the compound is one of the following:

Compound T121

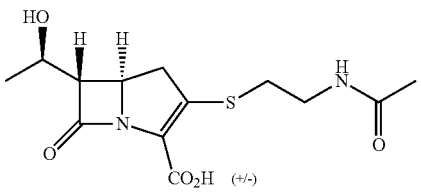

Compound T122

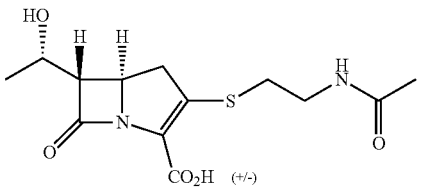

Compound T123

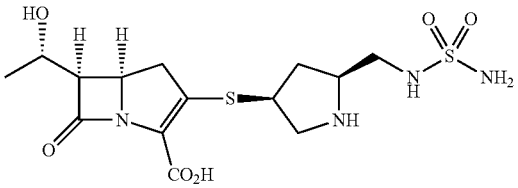

Compound T125
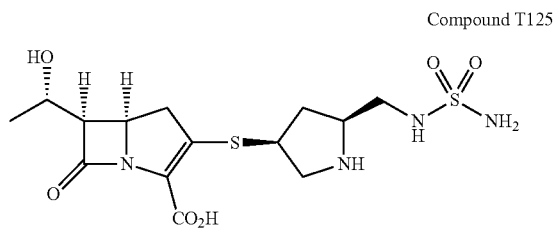

Compound T193
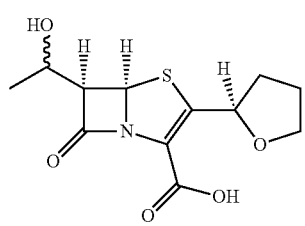

Compound T202
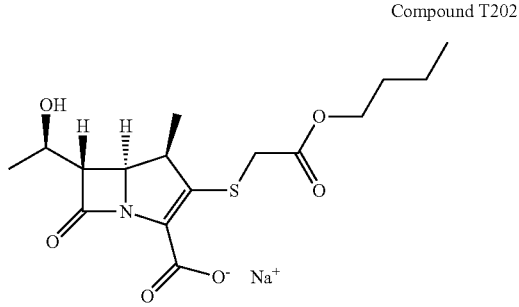

Compound T203
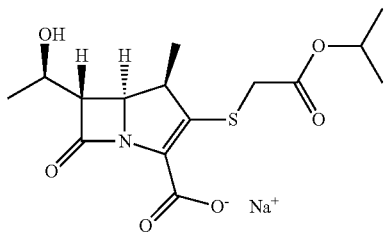

Compound T205
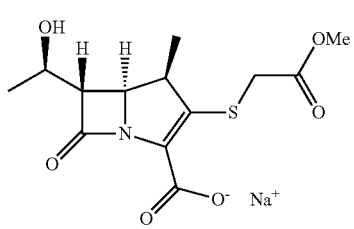

Compound T206
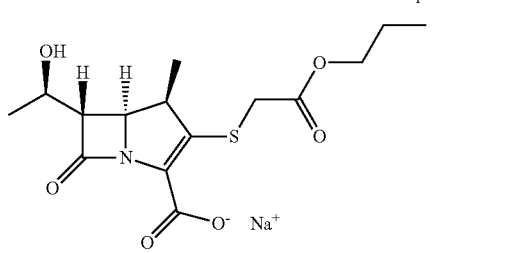

Compound T208
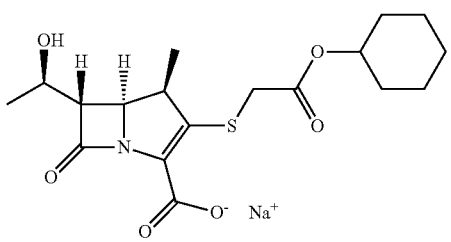

Compound T221
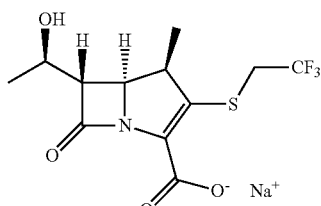

Compound T223
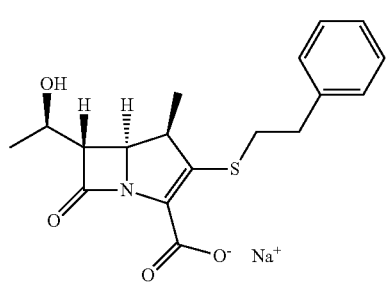

Compound T224
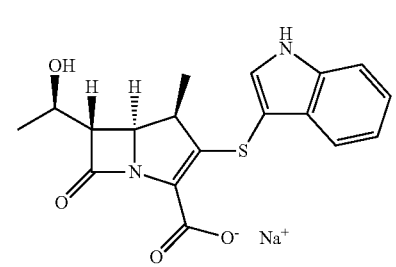

and

Compound T225
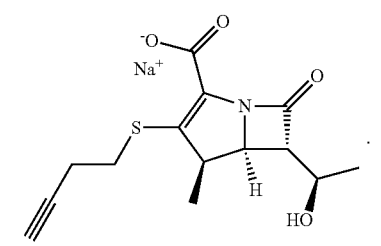

3. A pharmaceutical composition comprising a compound, salt, solvate, or stereoisomer of claim 1, and a pharmaceutically acceptable carrier.

4. A pharmaceutical composition comprising a compound, salt, solvate, or stereoisomer of claim 1, and at least one or more other antimicrobial compounds.

5. A method of use of a compound, salt, solvate, or stereoisomer of claim 1 comprising administering to a subject having a bacterial infection an effective amount of a compound, salt, solvate, or stereoisomer of claim 1 and treating the bacterial infection in the subject.

6. The method of claim 5 wherein the bacterial infection is selected from the group consisting of *M. tuberculosis*, *M.*

*abscessus, A. baumannii, S. aureus, K. pneumoniae, E. cloacae, P. aeruginosa* and *E. faecalis* or a combination thereof.

7. The method of claim 5 wherein the bacterial infection is one or more strains of bacteria that is resistant to antimicrobial agents directed to inactive D, D-transpeptidase.

8. A method of inhibiting the growth of a bacteria in vitro comprising contacting the bacteria with an effective amount of a compound, salt, solvate, or steroisomer of claim 1 wherein the bacteria stops growing than when the subject is not administered an effective amount of the compound.

9. A method of inhibiting L,D-transpeptidase activity in a subject with a bacterial infection, comprising administering to the subject an effective amount of a compound, salt, solvate, or stereoisomer of claim 1 wherein the L,D-transpeptidase activity is less than when the subject is not administered an effective amount of the compound.

10. A method of inhibiting L,D-transpeptidase activity in a subject with a bacterial infection, comprising administering to the subject comprising a bacteria with L,D-transpeptidase, an effective amount of a compound, salt, solvate, or stereoisomer of any one of the compounds selected from the group consisting of:

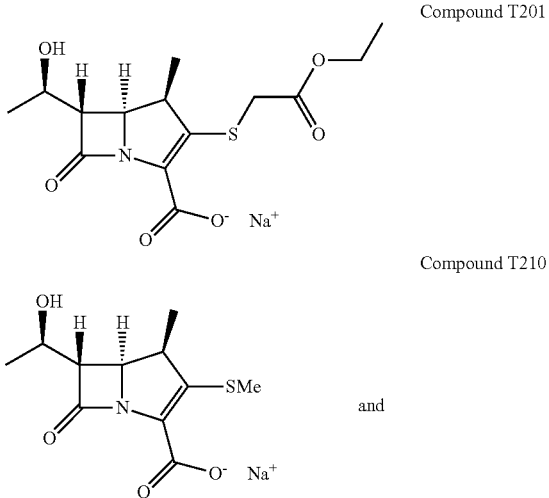

Compound T201

Compound T210 and

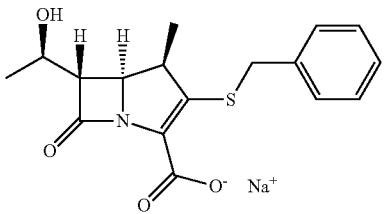

Compound T222 wherein the L,D-transpeptidase activity in the subject with the bacterial is less than when the subject is not administered an effective amount of any one of the compounds.

11. A pharmaceutical composition comprising a compound, salt, solvate, or stereoisomer of claim 2, and a pharmaceutically acceptable carrier.

12. A pharmaceutical composition comprising a compound, salt, solvate, or stereoisomer of claim 2, and at least one or more other antimicrobial compounds.

13. A method of use of a compound, salt, solvate, or stereoisomer of claim 2 comprising administering to a subject having a bacterial infection an effective amount of a compound, salt, solvate, or stereoisomer of claim 2 and treating the bacterial infection in the subject.

14. A method of inhibiting the growth of a bacteria in vitro comprising contacting the bacteria with an effective amount of a compound, salt, solvate, or steroisomer of claim 2 wherein the bacteria stops growing than when the subject is not administered an effective amount of the compound.

15. A method of inhibiting L,D-transpeptidase activity in a subject with a bacterial infection, comprising administering to the subject an effective amount of a compound, salt, solvate, or stereoisomer of the claim 2 wherein the L,D-transpeptidase activity is less than when the subject is not administered an effective amount of the compound.

* * * * *

```
                        SEQUENCE LISTING

<160> NUMBER OF SEQ ID NOS: 41

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
attgccatat ggatctgctg gtgcccaagc                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatactcga gttacgcctt ggcgttaccg                                    30

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caactcgccc aacggagcac gcaccgatgt cgac                               34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtcgacatcg gtgcgtgctc cgttgggcga gttg                               34

<210> SEQ ID NO 6
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 6
caactcgccc aacggatttc gcaccgatgt cgac                              34

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcgacatcg gtgcgaaatc cgttgggcga gttg                              34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcggtgtc ttcgtggcct cagcgccgtg gtcg                              34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgaccacggc gctgaggcca cgaagacacc gctg                              34

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggtgtcttc gtgcgttcag cgccgtggtc g                                 31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgaccacggc gctgaacgca cgaagacacc g                                 31

<210> SEQ ID NO 12
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
cagcggtgtc ttcgtgaact cagcgccgtg gtc                                    33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaccacggcg ctgagttcac gaagacaccg ctg                                    33

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccacaccaac accagcgctg gctgcctgaa cgtc                                   34

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacgttcagg cagccagcgc tgtgtgttggt gtgg                                  34

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacaccaaca ccagccgtgg ctgcctgaac gtc                                    33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacgttcagg cagccacggc tggtgttggt gtg                                    33

<210> SEQ ID NO 18
<211> LENGTH: 32
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 18
ccacaccaac accagcaatg gctgcctgaa cg                                    32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgttcaggca gccattgctg gtgttggtgt gg                                    32

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caacaccagc catggcgcgc tgaacgtcag cccgag                                36

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctcgggctga cgttcagcgc gccatggctg gtgttg                                36

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caacaccagc catggcagcc tgaacgtcag ccc                                   33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggctgacgt tcaggctgcc atggctggtg ttg                                   33

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 24
attgccatat gccactccaa ccgatccca                                    29

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caatactcga gctagccgac cacctcaatg gg                                32

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
attgccatat gggccacgca ttggccgcaa gtcc                              34

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caatactcga gttacgcgtt gatgatgatc gg                                32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
attgccatat gtcggttaag gatggagccg ta                                32

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caatactcga gttattgctg gcgggcgttt c                                 31

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
attgccatat gtgggccgtt gattatccgc ttcc                                34

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caatactcga gctattgggt aagcagaccg ttg                                 33

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
attgccatat ggattatccg ttaccgcccg                                     30

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caatactcga gctactgcgt caccttctcg ccatc                               35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
attgccatat gtcggccctg gaactgcagc tcccg                               35

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caatactcga gtcagggcgt aagctgggta ggatcg                              36

<210> SEQ ID NO 36
<211> LENGTH: 408
<212> TYPE: PRT
<213> ORGANISM: Mycobacterium tuberculosis

<400> SEQUENCE: 36

Met Pro Lys Val Gly Ile Ala Ala Gln Ala Gly Arg Thr Arg Val Arg

```
  1               5                   10                  15
Arg Ala Trp Leu Thr Ala Leu Met Met Thr Ala Val Met Ile Gly Ala
                20                  25                  30

Val Ala Cys Gly Ser Gly Arg Gly Pro Ala Pro Ile Lys Val Ile Ala
                35                  40                  45

Asp Lys Gly Thr Pro Phe Ala Asp Leu Leu Val Pro Lys Leu Thr Ala
                50                  55                  60

Ser Val Thr Asp Gly Ala Val Gly Val Thr Val Asp Ala Pro Val Ser
 65                 70                  75                  80

Val Thr Ala Ala Asp Gly Val Leu Ala Ala Val Thr Met Val Asn Asp
                    85                  90                  95

Asn Gly Arg Pro Val Ala Gly Arg Leu Ser Pro Asp Gly Leu Arg Trp
                100                 105                 110

Ser Thr Thr Glu Gln Leu Gly Tyr Asn Arg Arg Tyr Thr Leu Asn Ala
                115                 120                 125

Thr Ala Leu Gly Leu Gly Gly Ala Ala Thr Arg Gln Leu Thr Phe Gln
            130                 135                 140

Thr Ser Ser Pro Ala His Leu Thr Met Pro Tyr Val Met Pro Gly Asp
145                 150                 155                 160

Gly Glu Val Val Gly Val Gly Glu Pro Val Ala Ile Arg Phe Asp Glu
                165                 170                 175

Asn Ile Ala Asp Arg Gly Ala Ala Glu Lys Ala Ile Lys Ile Thr Thr
                180                 185                 190

Asn Pro Pro Val Glu Gly Ala Phe Tyr Trp Leu Asn Asn Arg Glu Val
                195                 200                 205

Arg Trp Arg Pro Glu His Phe Trp Lys Pro Gly Thr Ala Val Asp Val
                210                 215                 220

Ala Val Asn Thr Tyr Gly Val Asp Leu Gly Glu Gly Met Phe Gly Glu
225                 230                 235                 240

Asp Asn Val Gln Thr His Phe Thr Ile Gly Asp Glu Val Ile Ala Thr
                245                 250                 255

Ala Asp Asp Asn Thr Lys Ile Leu Thr Val Arg Val Asn Gly Glu Val
                260                 265                 270

Val Lys Ser Met Pro Thr Ser Met Gly Lys Asp Ser Thr Pro Thr Ala
                275                 280                 285

Asn Gly Ile Tyr Ile Val Gly Ser Arg Tyr Lys His Ile Ile Met Asp
                290                 295                 300

Ser Ser Thr Tyr Gly Val Pro Val Asn Ser Pro Asn Gly Tyr Arg Thr
305                 310                 315                 320

Asp Val Asp Trp Ala Thr Gln Ile Ser Tyr Ser Gly Val Phe Val His
                325                 330                 335

Ser Ala Pro Trp Ser Val Gly Ala Gln Gly His Thr Asn Thr Ser His
                340                 345                 350

Gly Cys Leu Asn Val Ser Pro Ser Asn Ala Gln Trp Phe Tyr Asp His
                355                 360                 365

Val Lys Arg Gly Asp Ile Val Glu Val Val Asn Thr Val Gly Gly Thr
                370                 375                 380

Leu Pro Gly Ile Asp Gly Leu Gly Asp Trp Asn Ile Pro Trp Asp Gln
385                 390                 395                 400

Trp Arg Ala Gly Asn Ala Lys Ala
                405

<210> SEQ ID NO 37
```

```
<211> LENGTH: 248
<212> TYPE: PRT
<213> ORGANISM: Mycobacteroides abscessus

<400> SEQUENCE: 37

Met Leu Val Val Thr Gly Leu Val Ser Leu Met Asn Ala Ala Val
1               5                   10                  15

Thr Ala Pro Ala Thr Leu Gly His Ala Leu Ala Ala Ser Pro Ser Gly
            20                  25                  30

Val Ala Ser Val Ser Pro Thr Pro Gly Gln Thr Val Gly Val Ala Met
        35                  40                  45

Pro Val Thr Ile Arg Phe Ala Ala Pro Val Ala Asp Arg Ile Ala Ala
50                  55                  60

Glu Arg Ser Ile Glu Phe Ser Ala Pro Lys Val Pro Ala Gly Ala Phe
65                  70                  75                  80

Ser Trp Val Asp Asn Ala Thr Val Arg Phe Thr Pro Arg Glu Tyr Trp
                85                  90                  95

Pro Ala His Ser Ser Ile Thr Val Ser Val Asn Gly Val Ser Gly Met
            100                 105                 110

Lys Tyr Lys Phe Gln Thr Gly Ser Glu Val Leu Gly Ile Gly Ser Ile
        115                 120                 125

Ser Gly His Thr Phe Thr Val Lys Ile Asp Gly Thr Val Met Arg Thr
130                 135                 140

Met Pro Ala Ser Met Gly Lys Pro Lys His Pro Thr Pro Val Gly Ser
145                 150                 155                 160

Phe Thr Ala Leu Glu Lys Gln Ser Pro Val Val Met Asp Ser Arg Thr
                165                 170                 175

Ile Gly Ile Pro Leu Asn Asp Pro Glu Gly Tyr Lys Leu Thr Val Tyr
            180                 185                 190

Tyr Ala Val Arg Val Thr Trp Gly Gly Val Tyr Val His Ser Ala Pro
        195                 200                 205

Trp Ser Thr Gly Ala Gln Gly Asn Ser Asn Val Ser His Gly Cys Ile
210                 215                 220

Asn Leu Ser Pro Asp Asn Ala Ser Trp Tyr Tyr Asn Thr Val Ser Ile
225                 230                 235                 240

Gly Asp Pro Ile Ile Ile Asn Ala
                245

<210> SEQ ID NO 38
<211> LENGTH: 406
<212> TYPE: PRT
<213> ORGANISM: Mycobacteroides abscessus

<400> SEQUENCE: 38

Met Thr Gln Gly Arg Pro Arg Leu His Ala Gly Ala Arg Arg Arg Trp
1               5                   10                  15

Val Ala Thr Leu Ala Leu Pro Val Ala Met Ala Val Leu Ala Gly
            20                  25                  30

Cys Ala Gly Ala Thr Thr Gln Glu Pro Pro Lys Val Ile Asp Lys Ala
        35                  40                  45

Thr Pro Tyr Ala Asp Leu Leu Val Pro Lys Leu Ala Met Ser Val Lys
    50                  55                  60

Asp Gly Ala Val Gly Val Ala Val Asp Ala Pro Val Thr Val Thr Ala
65                  70                  75                  80

Gly Glu Gly Val Leu Gly Ser Val Thr Met Val Asn Ser Asp Gly Lys
                85                  90                  95
```

Glu Ile Ala Gly Glu Ile Gly Pro Asp Gly Val Thr Trp Thr Thr Thr
            100                 105                 110

Glu Pro Leu Gly Tyr Asp Lys Gln Tyr Thr Ile Asn Ala Asp Ala Arg
            115                 120                 125

Gly Leu Gly Gly Val Ala Arg Ala Asn Ala Thr Phe Arg Thr Gln Ser
        130                 135                 140

Pro Asp Asn Met Thr Met Pro Tyr Val Met Pro Gly Asp Gly Glu Val
145                 150                 155                 160

Val Gly Val Gly Gln Thr Val Ala Ile Arg Phe Asp Glu Asn Ile Pro
                165                 170                 175

Asn Arg Ala Ala Ala Glu Lys Ala Ile Lys Ile Thr Thr Asn Pro Pro
                180                 185                 190

Val Glu Gly Ala Phe Tyr Trp Leu Asn Asn Arg Glu Val Arg Trp Arg
                195                 200                 205

Pro Glu Ser Phe Trp Asp Ser Gly Thr Ser Val Asp Val Lys Val Asn
            210                 215                 220

Thr Tyr Gly Val Asn Leu Gly Asp Gly Val Phe Gly Gln Asp Asn Val
225                 230                 235                 240

Ala Ser His Phe Thr Ile Gly Asp Ala Val Ile Ser Arg Val Asp Asp
                245                 250                 255

Thr Asn Lys Ile Leu Asn Ile Glu Arg Asn Gly Glu Ile Ile Lys Thr
                260                 265                 270

Met Pro Thr Ser Met Gly Lys Asp Lys Ala Pro Thr Asn Asn Gly Thr
            275                 280                 285

Tyr Ile Ile Gly Glu Arg Phe Lys Asp Leu Ile Met Asp Ser Ser Thr
            290                 295                 300

Tyr Gly Val Ala Val Asn Ser Pro Asp Gly Tyr Arg Thr Lys Val Gln
305                 310                 315                 320

Tyr Ala Thr Gln Met Ser Tyr Ser Gly Ile Tyr Val His Ala Ala Pro
                325                 330                 335

Trp Ser Val Gly Ala Gln Gly Arg Thr Asn Thr Ser His Gly Cys Leu
                340                 345                 350

Asn Val Ser Thr Ala Asn Ala Lys Trp Phe Tyr Glu Asn Thr Lys Arg
            355                 360                 365

Gly Asp Val Val Ile Val Ser Asn Thr Val Gly Pro Val Leu Pro Gly
370                 375                 380

Thr Glu Gly Leu Gly Asp Trp Asn Ile Pro Trp Ala Gln Trp Lys Ala
385                 390                 395                 400

Gly Asn Ala Arg Gln Gln
                405

<210> SEQ ID NO 39
<211> LENGTH: 299
<212> TYPE: PRT
<213> ORGANISM: Klebsiella pneumoniae

<400> SEQUENCE: 39

Met Lys Arg Lys Thr Met Ile Thr Leu Ala Leu Leu Ser Ala Leu Gly
1               5                   10                  15

Ala Ser Thr Ala Ala Trp Ala Val Asp Tyr Pro Leu Pro Pro Ala Asn
            20                  25                  30

Ser Arg Leu Ile Gly Gln Asn Gln Tyr Trp Thr Val Gln Glu Gly Asp
        35                  40                  45

Arg Asn Leu Gln Ala Ile Ala Arg His Phe Asp Thr Ala Ala Met Leu

```
        50                  55                  60
Ile Leu Glu Ala Asn Asp Thr Ile Ala Pro Val Gln Pro Lys Pro Gly
 65                  70                  75                  80

Thr Gln Val Leu Ile Pro Ser Gln Met Leu Leu Pro Asp Val Pro Arg
                     85                  90                  95

Glu Gly Ile Val Val Asn Leu Ala Glu Leu Arg Leu Tyr Tyr Phe Pro
                100                 105                 110

Pro Gly Glu Asn Gln Val Gln Val Tyr Pro Leu Gly Ile Gly Gln Leu
                115                 120                 125

Gly Leu Glu Thr Pro Glu Met Thr Thr Arg Val Gly Gln Lys Ile Pro
            130                 135                 140

Asn Pro Thr Trp Thr Pro Thr Ala Gly Ile Arg Ala Arg Ser Leu Glu
145                 150                 155                 160

Lys Gly Val Thr Leu Pro Ala Val Val Pro Ala Gly Pro Asn Asn Pro
                    165                 170                 175

Leu Gly Arg Tyr Ala Leu Arg Leu Ala Tyr Gly Asn Gly Glu Tyr Leu
                180                 185                 190

Ile His Gly Thr Asn Ala Pro Asp Ser Val Gly Leu Arg Val Ser Ser
            195                 200                 205

Gly Cys Met Arg Met Asn Ala Asp Asp Ile Lys Ala Leu Phe Ser Gln
210                 215                 220

Val Lys Thr Gly Thr Pro Val Arg Ile Ile Asn Gln Pro Val Lys Phe
225                 230                 235                 240

Ala Val Glu Pro Asp Gly Lys Arg Tyr Val Glu Val His Arg Pro Leu
                245                 250                 255

Ser Gln Thr Glu Gly Glu Asn Thr Arg Thr Ile Ala Tyr Thr Leu Pro
                260                 265                 270

Ala Ala Phe His Ala Phe Ala Glu Asp Lys Ala Val Asp Asp Leu Gln
            275                 280                 285

Leu Lys Lys Ala Met Ser Arg Arg Ala Gly Tyr
            290                 295

<210> SEQ ID NO 40
<211> LENGTH: 299
<212> TYPE: PRT
<213> ORGANISM: Enterobacter cloacae

<400> SEQUENCE: 40

Met Lys Arg Ala Ser Leu Ile Thr Leu Leu Leu Gly Ser Leu Gly
 1               5                  10                  15

Ala Leu Asn Ser Ala Ser Ala Met Asp Tyr Pro Leu Pro Ala Gly
                 20                  25                  30

Ser Arg Leu Ile Gly Gln Asn Gln Thr Tyr Ile Ile Gln Glu Gly Asp
                 35                  40                  45

Thr Lys Leu Gln Thr Ile Ala Arg Arg Phe Asn Thr Ala Ala Gln Leu
 50                  55                  60

Ile Leu Glu Thr Asn Asn Thr Ile Ala Pro Val Asn Pro Ala Pro Gly
 65                  70                  75                  80

Thr Val Ile Thr Ile Pro Ser Gln Met Leu Leu Pro Asp Thr Pro Arg
                     85                  90                  95

Glu Gly Ile Val Val Asn Leu Ala Glu Leu Arg Leu Tyr Tyr Tyr Pro
                100                 105                 110

Pro Gly Gly Asn Ile Val Gln Val Phe Pro Leu Gly Ile Gly Gln Leu
                115                 120                 125
```

```
Gly Leu Glu Thr Pro Val Thr Thr Arg Val Ser Gln Lys Ile Pro
130                 135                 140

Asn Pro Thr Trp Thr Pro Thr Pro Gly Ile Arg Ala Arg Ser Leu Glu
145                 150                 155                 160

Gln Gly Ile Lys Leu Pro Pro Val Val Pro Ala Gly Pro Asn Asn Pro
                165                 170                 175

Leu Gly Arg Phe Ala Leu Arg Leu Gly Val Gly Asn Gly Glu Tyr Leu
            180                 185                 190

Ile His Gly Thr Ser Ala Pro Asp Ser Val Gly Leu Arg Val Ser Ser
        195                 200                 205

Gly Cys Met Arg Met Asn Ala Pro Asp Ile Lys Ala Leu Phe Glu Gln
210                 215                 220

Val Arg Val Gly Thr Arg Val Gln Ile Ile Asn Glu Pro Val Lys Phe
225                 230                 235                 240

Ser Val Glu Pro Asp Gly Lys Arg Tyr Ile Glu Val His Arg Pro Leu
                245                 250                 255

Ala Gln Val Glu Gly Glu Asn Pro Gln Ile Thr Pro Ile Thr His Ser
            260                 265                 270

Ala Asp Phe Ala Ser Phe Val Ser Gln Ala Gly Ser Asp Lys Ala Leu
        275                 280                 285

Ile Asp Lys Ala Leu Ser Arg Arg Ala Gly Ile
290                 295

<210> SEQ ID NO 41
<211> LENGTH: 298
<212> TYPE: PRT
<213> ORGANISM: Pseudomonas aeruginosa

<400> SEQUENCE: 41

Met Leu Ser Arg Val Pro Val Val Ser Leu Ser Phe Ala Ala Leu Leu
1               5                   10                  15

Ser Ala Gly Ser Ala Ser Ala Leu Glu Leu Gln Leu Pro Pro Pro Gly
            20                  25                  30

Glu Asp Val Val Gly Gln Val Gln Val Ile Lys Ala Lys Tyr Glu Asp
        35                  40                  45

Thr Phe Ala Asp Leu Gly Glu Gln Tyr Asn Leu Gly Tyr Ser Glu Met
    50                  55                  60

Val Ala Ala Asn Pro Gly Val Asp Pro Trp Leu Pro Gly Val Gly Thr
65                  70                  75                  80

Glu Val Ile Ile Pro Thr Arg Phe Val Leu Pro Pro Gly Pro Arg Glu
                85                  90                  95

Gly Val Val Ile Asn Leu Ala Glu Tyr Arg Leu Tyr Tyr Tyr Pro Lys
            100                 105                 110

Gly Gln Asn Val Val His Thr Tyr Pro Leu Gly Ile Gly Arg Glu Gly
        115                 120                 125

Trp Gly Ser Pro Ile Ala Asn Thr Arg Ile Thr Ala Lys Thr Lys Asp
    130                 135                 140

Pro Ala Trp Tyr Pro Pro Ala Ser Ile Arg Ala Glu His Ala Ala Asp
145                 150                 155                 160

Gly Asp Pro Leu Pro Thr Val Val Pro Gly Pro Asp Asn Pro Leu
                165                 170                 175

Gly Pro Tyr Lys Leu Thr Leu Gly Val Pro Gly Tyr Leu Ile His Gly
            180                 185                 190

Ser Asn Lys Lys Phe Gly Ile Gly Thr Arg Thr Ser His Gly Cys Phe
        195                 200                 205
```

```
Arg Met Tyr Asn Ala Asp Val Thr His Leu Phe Ser Met Ile Ser Val
    210             215             220
Gly Thr Ser Val Arg Ile Ile Asn Glu Pro Tyr Lys Phe Gly Val Ser
225             230             235             240
Asn Gly Lys Val Tyr Leu Glu Ala His Thr Pro Leu Asn Asp His Gly
                245             250             255
Asp Pro Ser Val Val Asp Lys His Thr Ala Val Ile Asn Thr Leu Leu
            260             265             270
Lys Arg Asp Asp Leu Ala Lys Arg Ile Gln Leu Asn Trp Asp Val Val
        275             280             285
Arg Glu Val Val Ala Ser Glu Asp Gly Val
    290             295
```